US012023207B2

United States Patent
Hollopeter et al.

(10) Patent No.: US 12,023,207 B2
(45) Date of Patent: Jul. 2, 2024

(54) ARTICULATABLE SURGICAL LIGHTING SYSTEM HAVING HIGH BANDWIDTH TRANSMISSION FROM LIGHT HEAD

(71) Applicant: American Sterilizer Company, Mentor, OH (US)

(72) Inventors: Michael Evan Hollopeter, Kirtland, OH (US); Ian Hugh Cook, Pawtucket, RI (US); Purushottam Parajuli, Solon, OH (US); Lance Clark Bellows, Painesville, OH (US)

(73) Assignee: American Sterilizer Company, Mentor, OH (US)

(*) Notice: Subject to any disclaimer, the term of this patent is extended or adjusted under 35 U.S.C. 154(b) by 589 days.

(21) Appl. No.: 17/212,243

(22) Filed: Mar. 25, 2021

(65) Prior Publication Data
US 2021/0298865 A1   Sep. 30, 2021

Related U.S. Application Data

(60) Provisional application No. 63/000,719, filed on Mar. 27, 2020, provisional application No. 63/000,672, (Continued)

(51) Int. Cl.
*A61B 90/30* (2016.01)
*A61B 90/00* (2016.01)
(Continued)

(52) U.S. Cl.
CPC ............ *A61B 90/30* (2016.02); *A61B 90/361* (2016.02); *A61B 90/37* (2016.02);
(Continued)

(58) Field of Classification Search
CPC ...... G03B 30/00; G03B 17/561; G03B 15/14; G03B 7/15; A61B 90/30; A61B 90/361;
(Continued)

(56) References Cited

U.S. PATENT DOCUMENTS 5,633,963 A    5/1997  Rickenbach et al.
6,633,328 B1 * 10/2003  Byrd ...................... A61B 90/30
                                                         348/E7.087

(Continued)

FOREIGN PATENT DOCUMENTS

DE       19653507 A1   6/1998
EP        0488205 B1   7/1997
(Continued)

OTHER PUBLICATIONS

International Search Report and Written Opinion of the International Searching Authority in corresponding Internation Application No. PCT/US2021/024104, dated Jul. 22, 2021.
(Continued)

*Primary Examiner* — Christopher E Mahoney
(74) *Attorney, Agent, or Firm* — Renner, Otto, Boisselle & Sklar, LLP

(57) ABSTRACT

A surgical lighting system includes a central shaft, a surgical light head, an extension arm, a load balancing arm, and a yoke assembly. The extension arm is pivotably mounted to the central shaft. The load balancing arm is pivotably mounted to the extension arm. The yoke assembly supports the light head for multi-axis movement relative to the load balancing arm. The surgical light head includes a plurality of light emitting elements that are arranged to emit light downward to a region of interest and an optical signal generating component configured to capture data associated with the region of interest and generate an optical signal based on the captured data. Optical fiber cables and rotatable joints transmit the optical signal associated with the captured data from the surgical light head to one or more of the yoke assembly, the load balancing arm, the extension arm, and the central shaft.

22 Claims, 35 Drawing Sheets

Related U.S. Application Data filed on Mar. 27, 2020, provisional application No. 63/000,655, filed on Mar. 27, 2020.

(51) Int. Cl.
*F21V 33/00* (2006.01)
*F21W 131/205* (2006.01)
*G02B 6/38* (2006.01)
*G03B 15/14* (2021.01)
*G03B 17/56* (2021.01)
*G03B 30/00* (2021.01)
*A61B 90/35* (2016.01)
*A61B 90/50* (2016.01)

(52) U.S. Cl.
CPC ........ *F21V 33/0052* (2013.01); *G02B 6/3885* (2013.01); *G03B 15/14* (2013.01); *G03B 17/561* (2013.01); *G03B 30/00* (2021.01); *A61B 2090/306* (2016.02); *A61B 2090/308* (2016.02); *A61B 90/35* (2016.02); *A61B 2090/5025* (2016.02); *F21W 2131/205* (2013.01)

(58) Field of Classification Search
CPC ... A61B 90/37; A61B 90/35; A61B 2090/306; A61B 2090/3614
See application file for complete search history.

(56) References Cited

U.S. PATENT DOCUMENTS

| | | |
|---|---|---|
| 6,758,599 B2 | 7/2004 | Keselman et al. |
| 6,899,442 B2 * | 5/2005 | Howell .................. F21V 21/14 362/147 |
| 7,352,929 B2 | 4/2008 | Hagen et al. |
| 7,526,155 B2 | 4/2009 | Hirohashi et al. |
| 7,726,823 B2 | 6/2010 | Rus et al. |
| 8,721,195 B2 | 5/2014 | Doric |
| 8,786,385 B1 | 7/2014 | Lorenc |
| 8,909,008 B1 | 12/2014 | Tzeng et al. |
| 9,207,406 B2 | 12/2015 | Bowman |
| 9,213,144 B2 | 12/2015 | Jones et al. |
| 9,360,630 B2 | 6/2016 | Jenner et al. |
| 9,673,892 B2 | 6/2017 | Angerpointner et al. |
| 10,054,746 B2 | 8/2018 | Rollinger et al. |
| 2002/0191389 A1 | 12/2002 | Hill |
| 2003/0161158 A1 | 8/2003 | Jesurun et al. |
| 2008/0002934 A1 | 1/2008 | Hagen et al. |
| 2013/0223798 A1 | 8/2013 | Jenner et al. |
| 2014/0142436 A1 | 5/2014 | Hutchins et al. |
| 2014/0193149 A1* | 7/2014 | Jones .................... H04B 10/80 398/43 |
| 2015/0184779 A1 | 7/2015 | Timoszyk et al. |
| 2016/0091117 A1 | 3/2016 | Boccoleri et al. |
| 2018/0017736 A1 | 1/2018 | Boccoleri et al. |
| 2018/0120510 A1 | 5/2018 | Sullivan |
| 2019/0196112 A1 | 6/2019 | Sipple |
| 2019/0391338 A1 | 12/2019 | Tearney et al. |

FOREIGN PATENT DOCUMENTS

| | | |
|---|---|---|
| EP | 1251722 A2 | 10/2002 |
| EP | 3461409 A1 | 4/2019 |
| WO | 03/072995 A1 | 9/2003 |

OTHER PUBLICATIONS

Written Opinion of the International Searching Authority in corresponding International Application No. PCT/US2021/024104, dated Feb. 8, 2022.

* cited by examiner

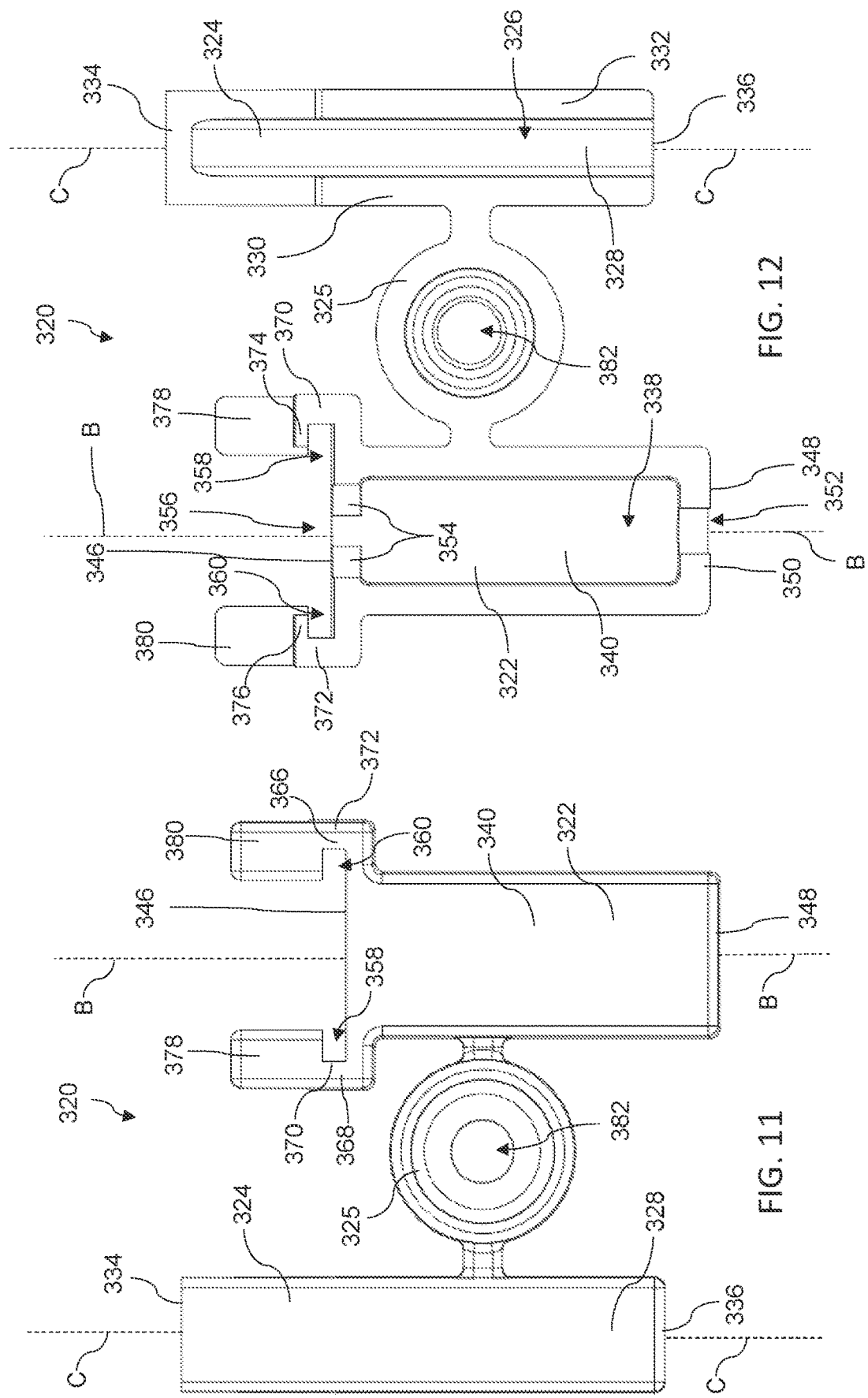

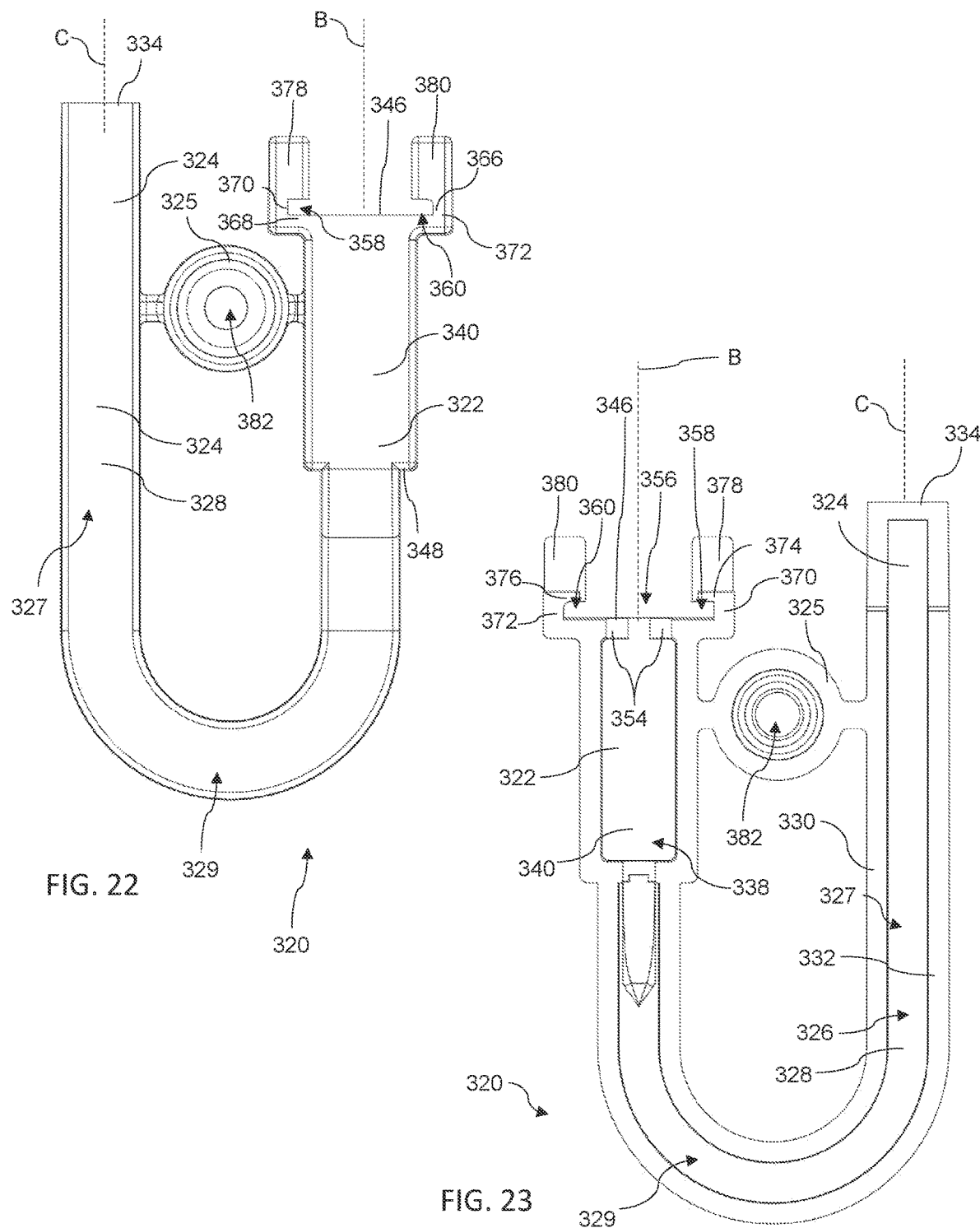

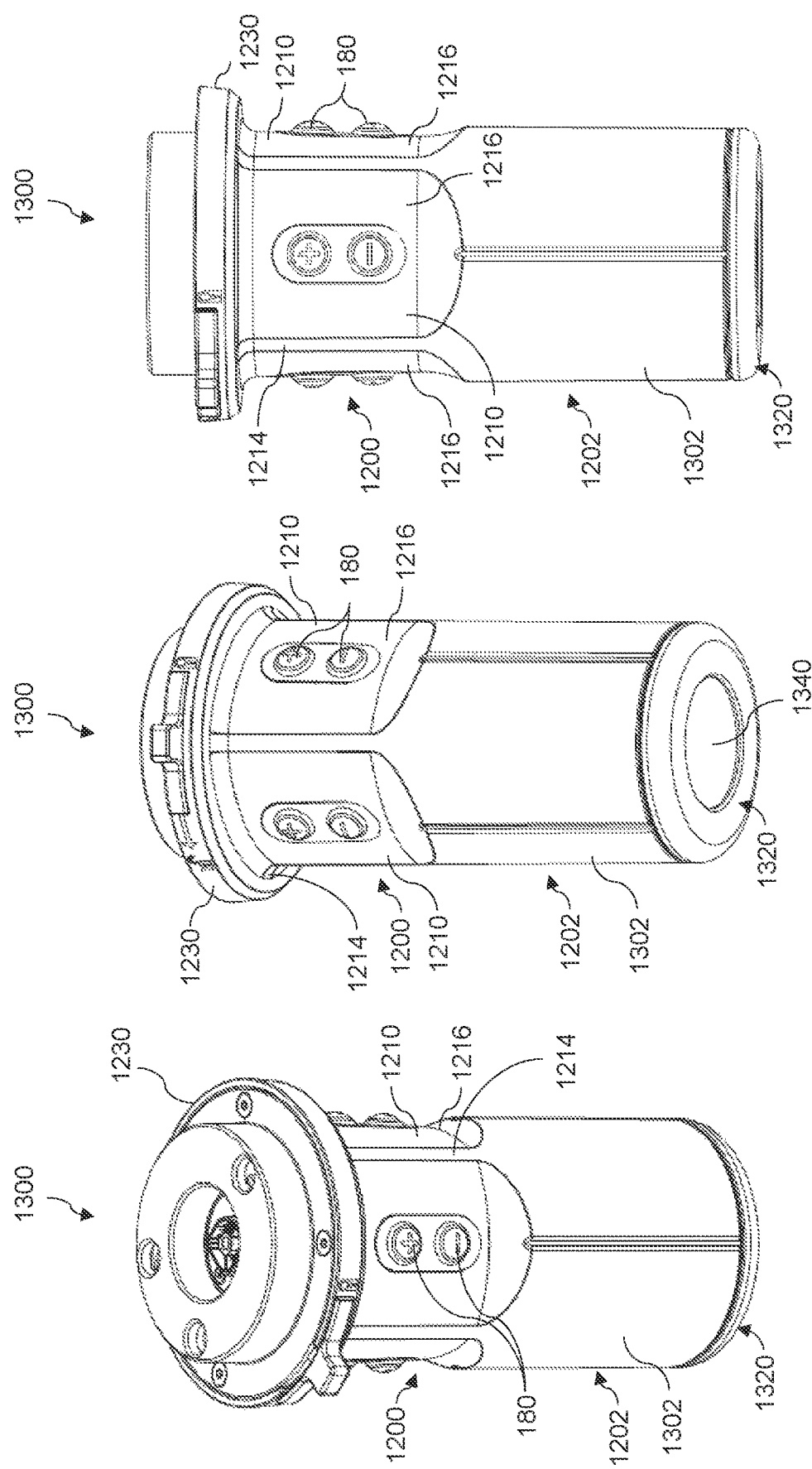

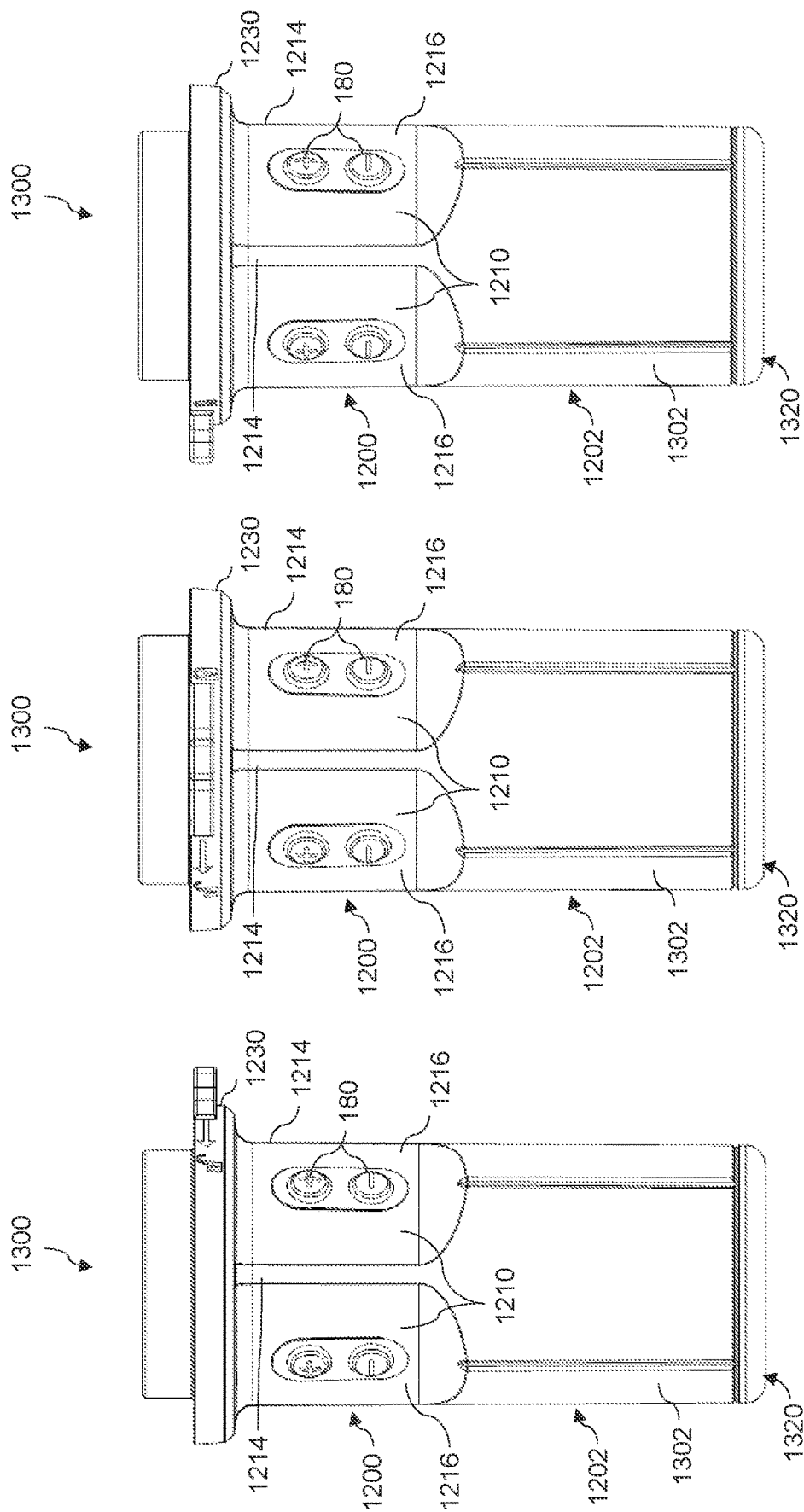

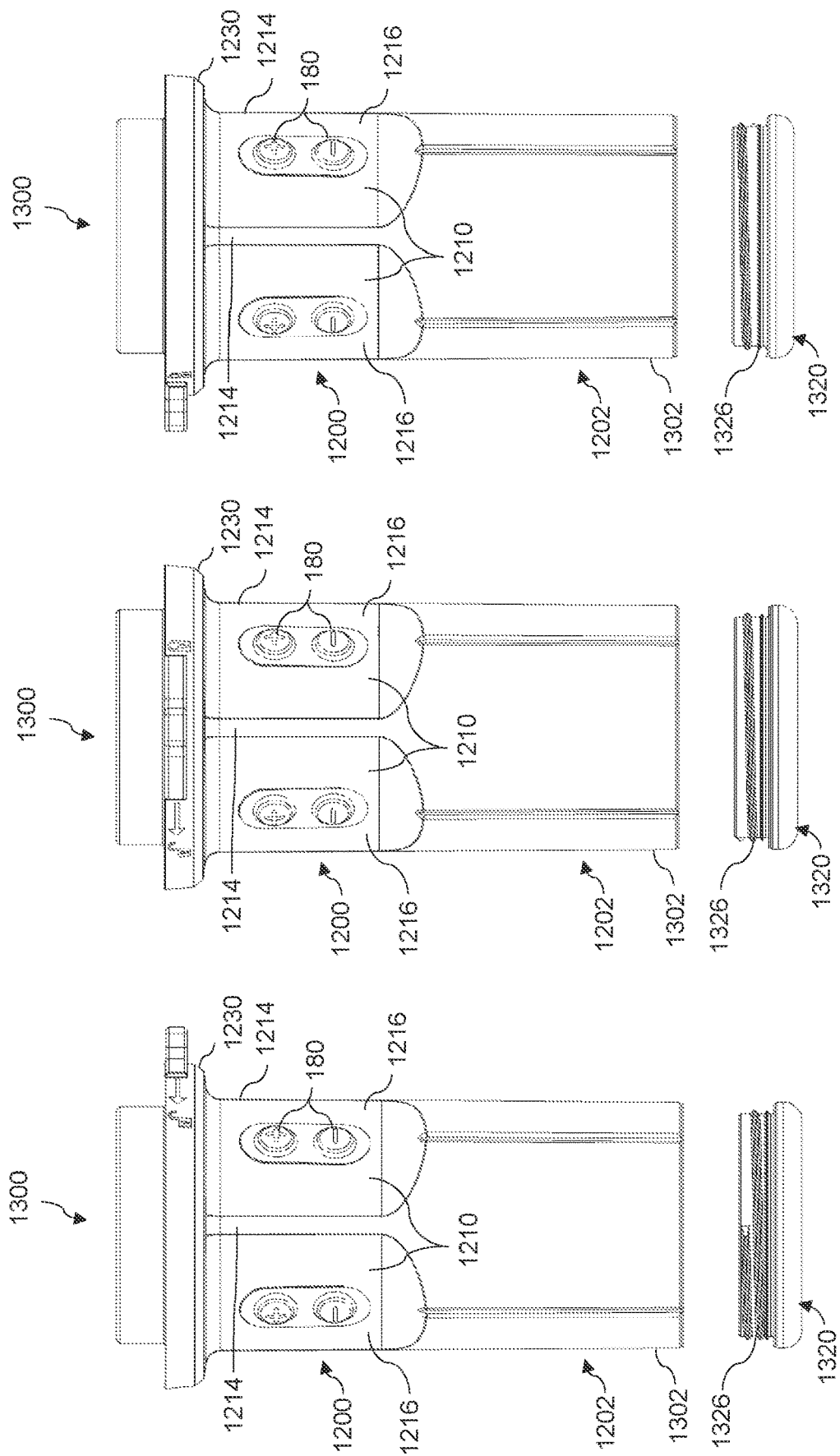

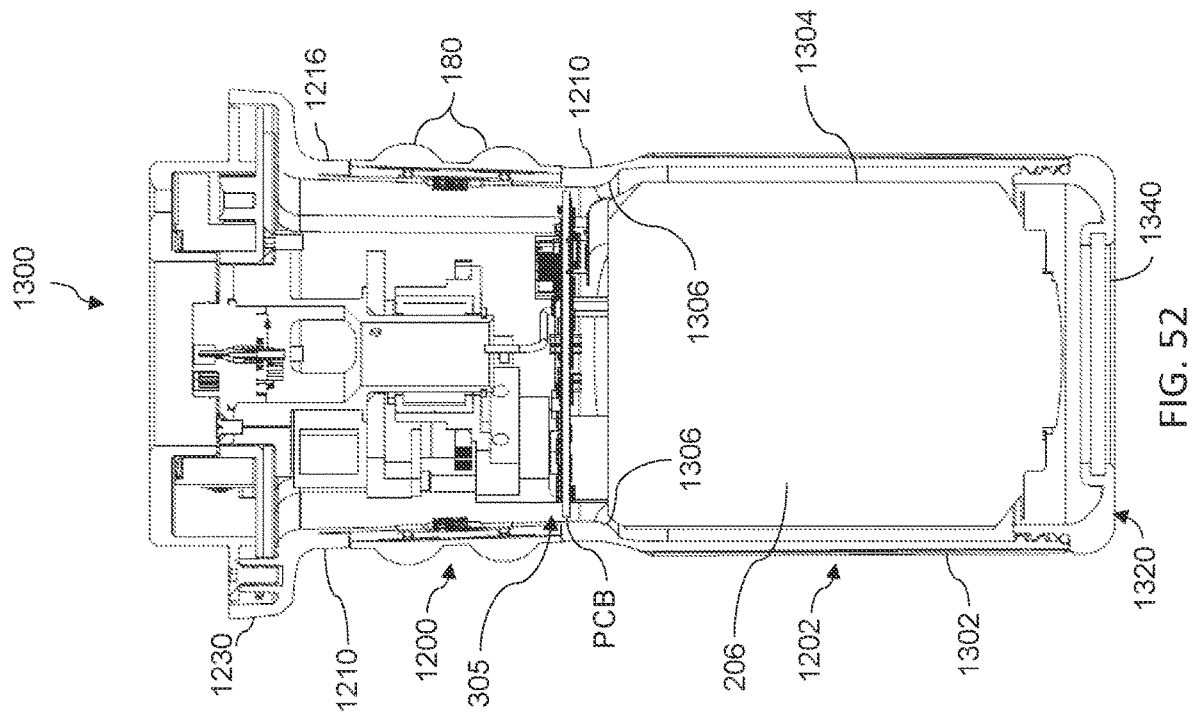
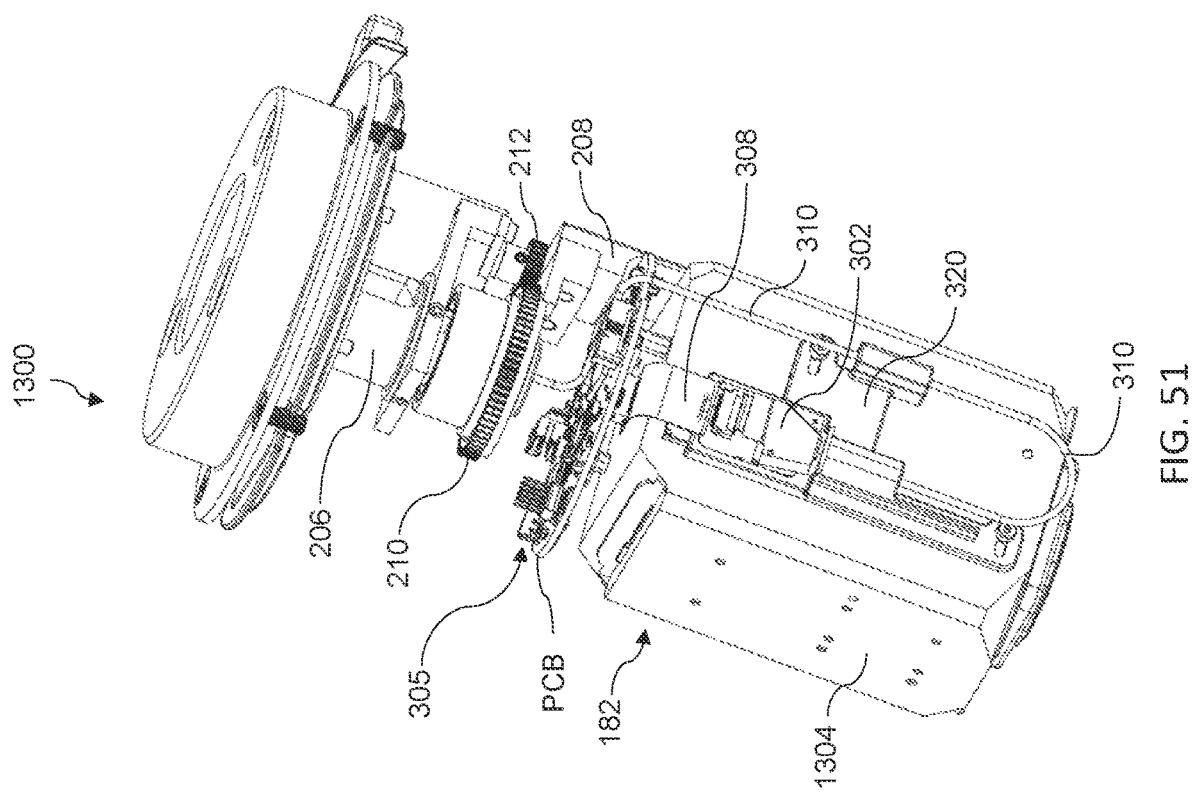

ARTICULATABLE SURGICAL LIGHTING SYSTEM HAVING HIGH BANDWIDTH TRANSMISSION FROM LIGHT HEAD

This application claims priority to U.S. Patent Application No. 63/000,719 filed Mar. 27, 2020; U.S. Patent Application No. 63/000,655 filed Mar. 27, 2020; and U.S. Patent Application No. 63/000,672 filed Mar. 27, 2020. These prior applications are incorporated herein by reference.

FIELD OF THE INVENTION

The technology of the present disclosure relates generally to a surgical lighting system, and more specifically to an articulatable surgical lighting system that provides for high bandwidth transmission from a surgical light head to other components of the surgical lighting system.

BACKGROUND

Light heads for medical device support systems, suspension systems and/or other carry systems, are used in health treatment settings such as hospital examination rooms, clinics, surgery rooms and emergency rooms to illuminate a region of interest (e.g., surgical treatment site or other medical site) below or proximate the light head. The light heads typically include a housing, one or more light emitting elements mounted inside the housing, and a handle mounted to the housing to enable a healthcare professional or other individual to adjust the position of the light head according to the needs of a specific medical procedure. The handle is typically formed to have an ergonomic structure that enables a user to wrap a hand around the handle such that the internal space within the handle is limited.

In these health treatment settings, there is often a need to capture and/or record images or video of the region of interest. The images or video may be used for various purposes, such as a visual aid in performing a given procedure. One or more cameras may be included as a part of the medical device support system, suspension system and/or other carry system. For example, a camera may be mounted in the handle of the light head and arranged to capture images of the region of interest that is illuminated by the one or more light emitting elements of the light head. However, the type of camera used in the handle of the light head has been limited due to issues of adjustability and/or reliability of the camera, particularly in view of the limited space within the handle.

Further, a sterile handle in a surgical environment has ergonomic needs whereby a too large handle may be undesirable and, in some cases, unacceptable.

The afore described technological complications at the light head and light head handle also introduce complications in propagating a signal from the camera to elsewhere in the surgical lighting system or to a location separate from the surgical lighting system, for example, in a conference room separate from the operating room in which the surgical lighting system may be located.

Accordingly, there remains a need for further contributions in this area of technology.

SUMMARY OF INVENTION

The present disclosure relates to an articulatable surgical lighting system having high bandwidth transmission from a surgical light head to elsewhere in the surgical lighting system or to a location separate from the surgical lighting system. An exemplary application of the surgical lighting system includes propagation of an optical signal originating from the surgical light head to one or more components of the articulating assembly and one or more rotatable joints of the surgical lighting system to for example a display monitor.

According to one aspect of the invention, a surgical lighting system includes a central shaft; a surgical light head; an extension arm having a hub at a proximal end thereof mounted to the central shaft for pivotable movement about the central shaft; a load balancing arm coupled to a distal end of the extension arm for pivotable movement relative to the extension arm; a yoke assembly coupled to a distal end of the load balancing arm for pivotable movement relative to the load balancing arm, wherein the yoke assembly supports the surgical light head for multi-axis movement relative to the load balancing arm; wherein the surgical light head includes a plurality of light emitting elements that are arranged to emit light downward to a region of interest and an optical signal generating component configured to capture data associated with the region of interest and generate an optical signal based on the captured data; and one or more optical fiber cables and one or more rotatable joints configured to transmit the optical signal associated with the captured data from the surgical light head to one or more of the yoke assembly, the load balancing arm, the extension arm, and the central shaft.

Embodiments of the invention may include one or more of the following additional features separately or in combination.

The optical signal generating component may include a camera having a field of view that encompasses at least a portion of the region of interest, and the optical signal may include optical video signals associated with video data captured by the camera.

The optical signal may include a bidirectional control signal.

The surgical light head may include a light head housing and a handle mounted to the light head housing and protruding downward from the light head housing, and the optical signal generating component may be mounted within the handle.

The optical signal generating component may be rotatable within the handle.

The handle may include a first mating connector and the light head housing may include a hub having a second mating connector, and the handle may be selectively attachable to and detachable from the hub wherein, in the attached state, the mated first and second mating connectors connect to transmit the optical signal from a first optical fiber cable inside the handle to a second optical fiber cable inside the light head housing.

The one or more optical fiber cables may be configured to transmit the optical signal associated with the captured data from the surgical light head through the yoke assembly and the load balancing arm to the extension arm.

The yoke assembly may be pivotably rotatable about the distal end of the load balancing arm via a first continuously rotatable joint and the first continuously rotatable joint may be configured to transmit the optical signal from a first optical fiber cable in the yoke assembly to a second optical fiber cable in the load balancing arm.

The load balancing arm may be pivotably rotatable about the distal end of the extension arm via a second continuously rotatable joint and the second continuously rotatable joint may be configured to transmit the optical signal from a second optical fiber cable in the load balancing arm to a third optical fiber cable in the extension arm.

The extension arm may be pivotably rotatable about the central shaft via a third continuously rotatable joint and the third continuously rotatable joint may be configured to transmit the optical signal from a third optical fiber cable in the extension arm to a fourth optical fiber cable in the central shaft.

The one or more rotatable joints may include at least one fiber optic rotary joint.

The fiber optic rotary joint may include a physical contact fiber optic rotary joint.

The fiber optic rotary joint may include an expanded beam fiber optic rotary joint.

The surgical lighting system may further include a second extension arm having a second hub at a proximal end thereof mounted to the central shaft for pivotable movement about the central shaft, a second load balancing arm pivotably mounted to a distal end of the second extension arm, and a display monitor coupled to a distal end of the second load balancing arm, wherein the one or more optical fiber cables includes a continuous cable run configured to transmit the optical signal from the central shaft to the second extension arm, the second load balancing arm, and the display monitor.

The yoke assembly may be pivotably rotatable about the distal end of the load balancing arm via a first rotatable joint, wherein the first rotatable joint includes a rotational component in the yoke assembly structured as a first mating connector and a stationary component in the load balancing arm structured as a second mating connector, and the yoke assembly is selectively attachable to and detachable from the load balancing arm wherein, in the attached state, the mated first and second mating connectors connect to transmit the optical signal from a first optical fiber cable inside the yoke assembly to a second optical fiber cable inside the load balancing arm.

The load balancing arm may be pivotably rotatable about the distal end of the extension arm via a second rotatable joint, wherein the second rotatable joint includes a rotational component in the load balancing arm structured as a first mating connector and a stationary component in the extension arm structured as a second mating connector, and the load balancing arm is selectively attachable to and detachable from the extension arm wherein, in the attached state, the mated first and second mating connectors connect to transmit the optical signal from a second optical fiber cable inside the load balancing arm to a third optical fiber cable inside the extension arm.

According to another aspect of the invention, a surgical lighting system, includes a central shaft; a surgical light head; a display monitor; a first extension arm having a first hub at a proximal end thereof mounted to the central shaft for pivotable movement about the central shaft, and a first articulating assembly at a distal end thereof for supporting the surgical light head; a second extension arm having a second hub at a proximal end thereof mounted to the central shaft for pivotable movement about the central shaft, and a second articulating assembly at a distal end thereof for supporting the display monitor; wherein the surgical light head includes a plurality of light emitting elements that are arranged to emit light downward to a region of interest and an optical signal generating component configured to capture data associated with the region of interest and generate an optical signal based on the captured data; wherein the optical signal is configured to drive the display monitor; and, one or more optical fiber cables and one or more rotatable joints configured to transmit the optical signal associated with the captured data from the surgical light head to one or more of the first articulating assembly, the first extension arm, the central shaft, the second extension arm, the second articulating assembly, and the display monitor.

Embodiments of the invention may include one or more of the following additional features separately or in combination.

The optical signal may include a bidirectional optical signal.

According to another aspect of the invention, a surgical lighting system includes a central shaft; a surgical light head; a video processing device; an extension arm having a hub at a proximal end thereof mounted to the central shaft for pivotable movement about the central shaft, and an articulating assembly at a distal end thereof for supporting the surgical light head; wherein the surgical light head includes a plurality of light emitting elements that are arranged to emit light downward to a region of interest and an optical signal generating component configured to capture data associated with the region of interest and generate an optical signal based on the captured data; wherein the optical signal is configured to drive the video processing device; wherein the video processing device is located separate from the central shaft, the extension arm, and the articulating assembly; and one or more optical fiber cables and one or more rotatable joints configured to transmit the optical signal associated with the captured data from the surgical light head to one or more of the articulating assembly, the extension arm, the central shaft, and the video processing device.

Embodiments of the invention may include one or more of the following additional features separately or in combination.

The surgical lighting system may further include a ceiling plate connected to the central shaft, wherein the one or more optical fiber cables extends through the central shaft and through the ceiling plate to the video processing device.

The surgical lighting system may further include a video hub that converts the optical signal from the optical signal generating component into a video signal having video protocols compatible with the video processing device.

The optical signal generating device may include a camera and the video processing device may include a display monitor.

These and further features will be apparent with reference to the following description and attached drawings which set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings. The invention includes all changes, modifications and equivalents coming within the spirit and terms of the claims appended hereto.

Features that are described and/or illustrated with respect to one embodiment may be used in the same way or in a similar way in one or more other embodiments and/or in combination with or instead of the features of the other embodiments.

BRIEF DESCRIPTION OF THE DRAWINGS

The annexed drawings, which are not necessarily to scale, show various aspects of the present disclosure.

FIG. 11 is a front elevation view of the bracket of FIG. 9.

FIG. 12 is a rear elevation view of the bracket of FIG. 9.

FIG. 22 is a front elevation view of the bracket of FIG. 20.

FIG. 23 is a rear elevation view of the bracket of FIG. 20.

FIG. 38 is a top perspective view of a handle in accordance with another embodiment of the present disclosure having a handle housing including a grip portion.

FIG. 39 is a bottom perspective view of the FIG. 38 handle.

FIG. 40 is a front elevation view of the FIG. 38 handle, as viewed from the front of FIG. 38 and showing buttons in the plane of the paper.

FIG. 41 is a side elevation view of the FIG. 38 handle, as viewed from the left of FIG. 39.

FIG. 42 is a side elevation view of the FIG. 38 handle, as viewed from the front of FIG. 39.

FIG. 43 is a side elevation view of the FIG. 38 handle, as viewed from the right of FIG. 39.

FIG. 48 is similar to FIG. 41 except exploded to show a cap of the handle removed.

FIG. 49 is similar to FIG. 42 except exploded to show a cap of the handle removed.

FIG. 50 is similar to FIG. 43 except exploded to show a cap of the handle removed.

FIG. 51 is an exploded perspective view of parts of the handle of FIG. 38 with the handle housing removed.

FIG. 52 is a cross section view of the handle of FIG. 38.

DETAILED DESCRIPTION

Figure 1:
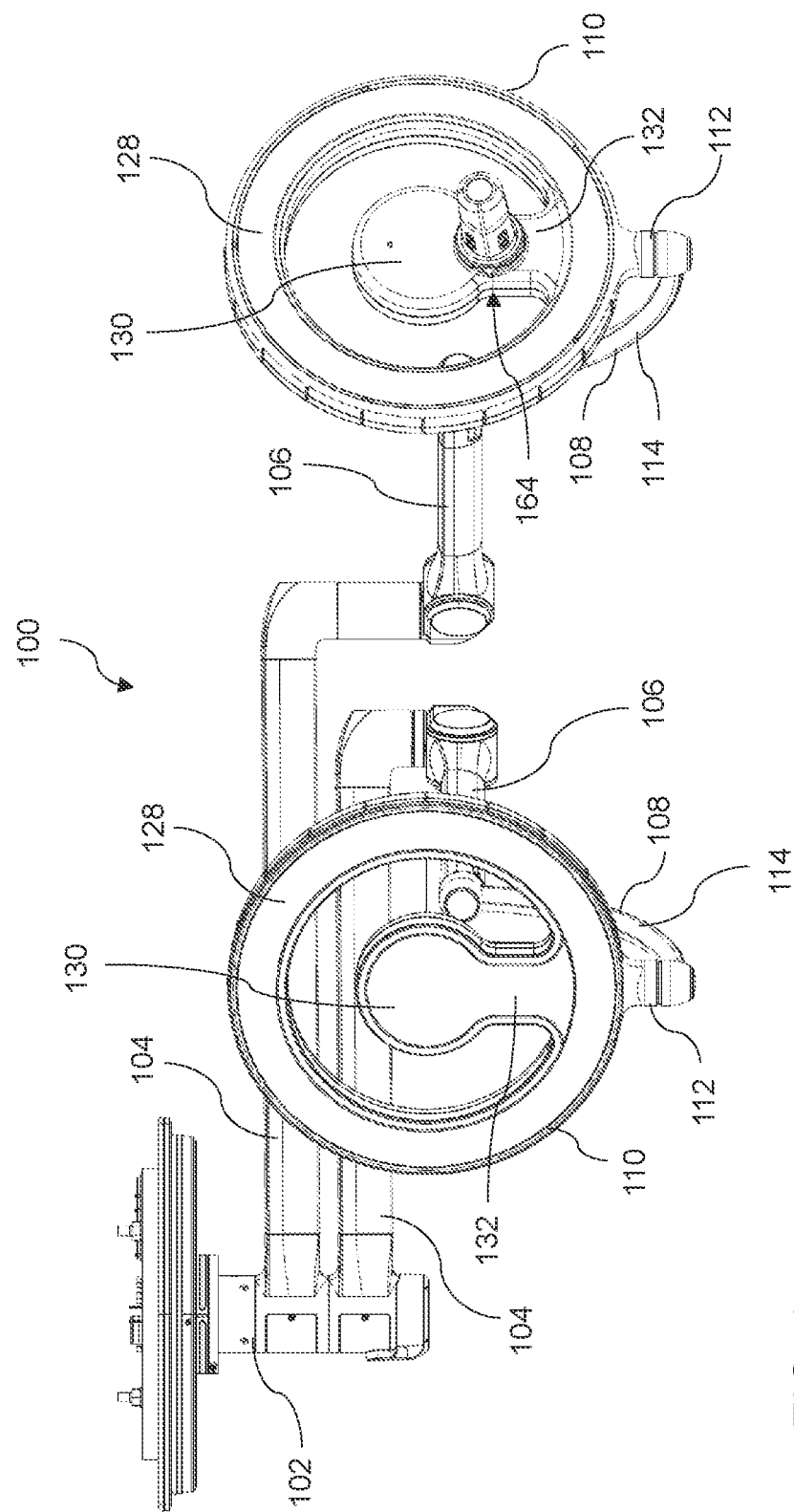
FIG. 1 is a side elevation view of an overall configuration of a medical device support system in accordance with an embodiment of the present disclosure, showing a top of a left positioned light head and a bottom of a right positioned light head.

For the purpose of promoting an understanding of the principles of the present disclosure, reference will now be made to the embodiments illustrated in the drawings and specific language will be used to describe the same. It will nevertheless be understood that no limitation of the scope of the present disclosure is thereby intended. The figures are not necessarily to scale. Features that are described and/or illustrated with respect to one embodiment may be used in the same way or in a similar way in one or more other embodiments and/or in combination with or instead of the features of the other embodiments. Any alterations and further modifications of the described embodiments, and any further applications of the principles of the present disclosure as described herein, are contemplated as would normally occur to one skilled in the art to which the present disclosure relates.

With reference to FIG. 1, an exemplary medical device support system is shown at 100. The medical device support system 100 includes a central shaft or support column 102 that is suspended from the ceiling, and two generally horizontal extension arms 104 mounted to the shaft 102 for rotational movement about the central shaft 102. In other implementations, the central shaft 102 could be mounted to a wall or stand rather than the ceiling. Two load balancing arms 106 are pivotably mounted to the distal ends of the respective extension arms 104. Yoke assemblies 108 are mounted to the distal ends of the respective load balancing arms 106. The yoke assemblies 108, in turn, support respective light heads 110 for multi-axis movement relative to the load balancing arms 106. Each light head 110 includes a bushing or other coupling member 112 that rotatably connects the light head 110 to the distal end of an arm 114 of a respective yoke assembly 108, as shown. The load balancing arms 106 and yoke assemblies 108 enable positioning of the light heads 110 to a desired orientation relative to, for example, a patient operating table and healthcare professionals in the operating room.

The exemplary medical device support system shown in FIG. 1 includes two light heads 110, each mounted to a respective extension arm 104, load balancing arm 106, and yoke assembly 108. It will be appreciated that in other embodiments, the medical device support system may include more or fewer light heads. It will also be appreciated that the medical device support system may include other accessories mounted to the central shaft 102.

Figure 2:
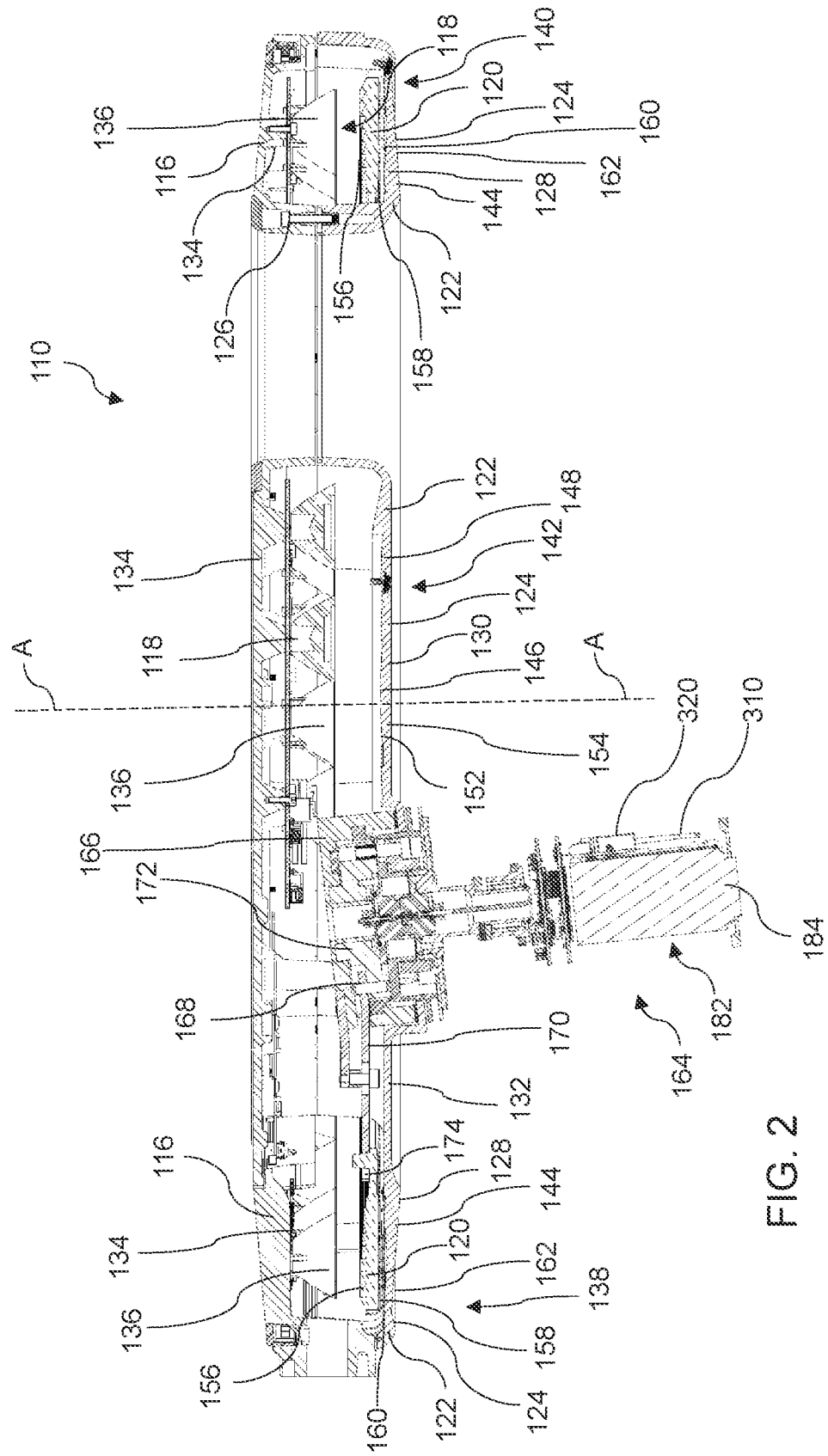
FIG. 2 is a side cross section view of a light head in accordance with an embodiment of the present disclosure, showing a housing base, a housing cover, and internal components of the light head and handle.

With additional reference to FIG. 2, each light head 110 of the system 100 includes a housing base 116, a plurality of light emitting elements 118, an annular shape lens 120, and a housing cover 122 including a housing lens 124. The housing base 116 and the housing cover 122 are connected by fasteners 126. The annular shape lens 120 and the housing lens 124 are in a light emitting path of the plurality of light emitting elements 118.

As shown in FIGS. 1 and 2, each light head 110 includes an annular shape outer portion 128, an inner round portion 130, and a radially protruding arm 132 that connects the annular shape outer portion 128 to the inner round portion 130. In the illustrative embodiment, the radially protruding arm 132 arranges the annular shape outer portion 128 and the inner round portion 130 in concentric relation to one another, and in concentric relation to the rotation axis A-A of the annular shape lens 120. The radially protruding arm 132 also houses one or more components for transferring rotational motion from a handle 164 mounted to the light head housing 116, 122 of the light head 110 to the annular shape lens 120 of the light head 110 (described in more detail below). It will be appreciated that the annular shape outer portion 128 and the inner round portion 130 need not be in concentric relation to one another and instead can be arranged by the protruding arm in eccentric relation to one another. It will further be appreciated that in an alternate embodiment the inner round portion 130 of the light head 110 may be omitted; and in such form, only the annular shape outer portion 128 emits light to the region of interest (e.g., surgical treatment site or other medical site) below or proximate the light head.

As shown in FIG. 2, an inside surface 134 of the housing base 116 supports the plurality of light emitting elements 118. The light emitting elements 118 may in some embodiments include one or more solid-state light emitters. Exemplary solid-state light emitters include such devices as light emitting diodes (LEDs), laser diodes, and organic LEDs (OLEDs). The LEDs may be broad spectrum LEDs (e.g., white light emitters) or LEDs that emit light of a desired color or spectrum (e.g., red light, green light, blue light, or ultraviolet light). In other embodiments, the LEDs may be a mixture of broad-spectrum LEDs and LEDs that emit narrow-band light of a desired color, or a mixture of LEDs that emit different respective colors or spectrum. In some embodiments, the solid-state light emitters constituting the light emitting elements 118 all generate light having the same nominal spectrum. In other embodiments, at least some of the solid-state light emitters constituting the light emitting elements 118 generate light that differs in spectrum from the light generated by the remaining solid-state light emitters. In other embodiments, the light emitting elements 118 may include one or more other types of light sources. Non-limiting examples of light sources include halogen, fluorescent, compact fluorescent, incandescent, and the like. In still other embodiments, the light emitting elements 118 may include a combination of solid-state light emitters and one or more of the above other types of light sources.

Figure 8:
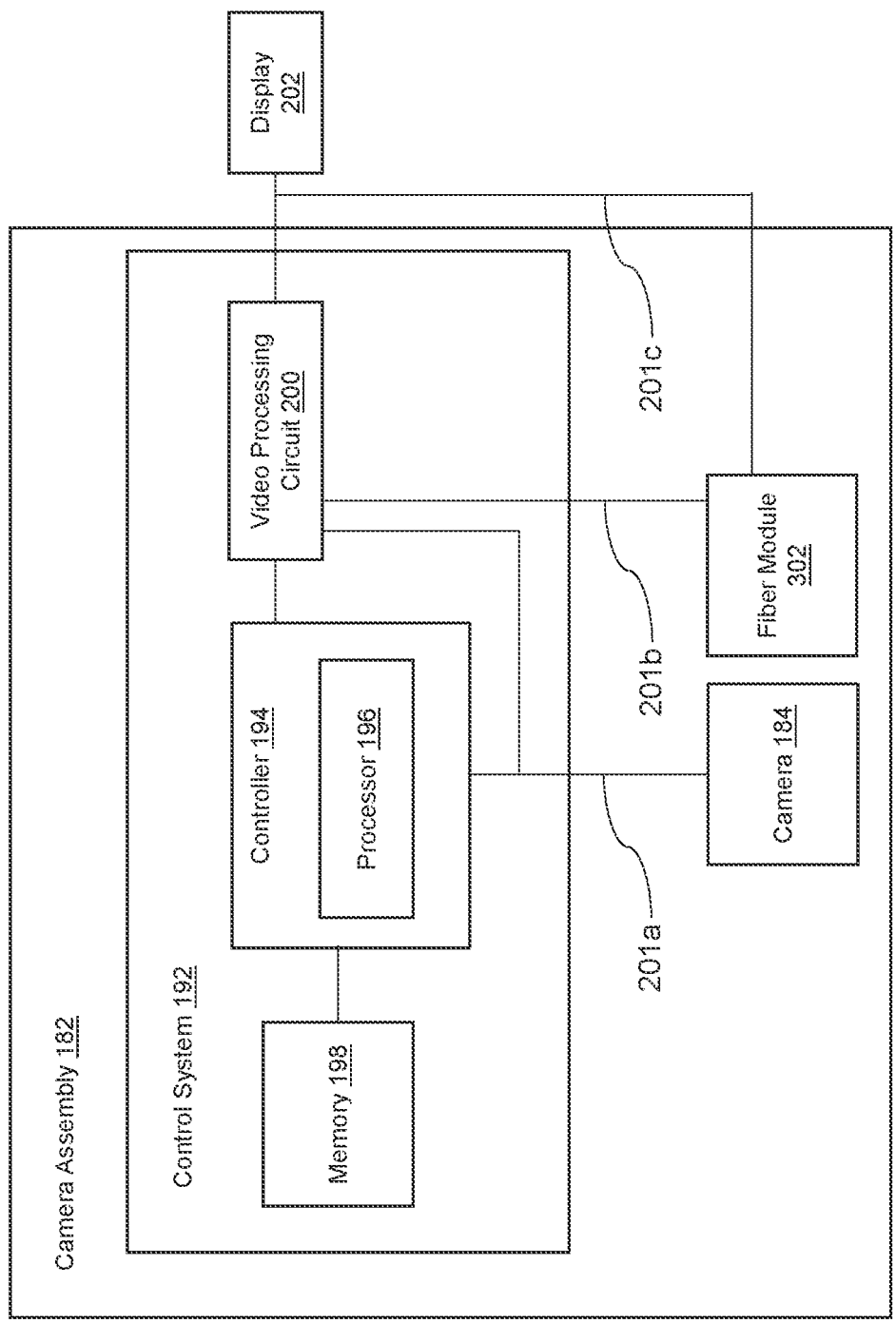
FIG. 8 is a schematic view of exemplary control system and display coupled to the camera assembly.
Figure 9:
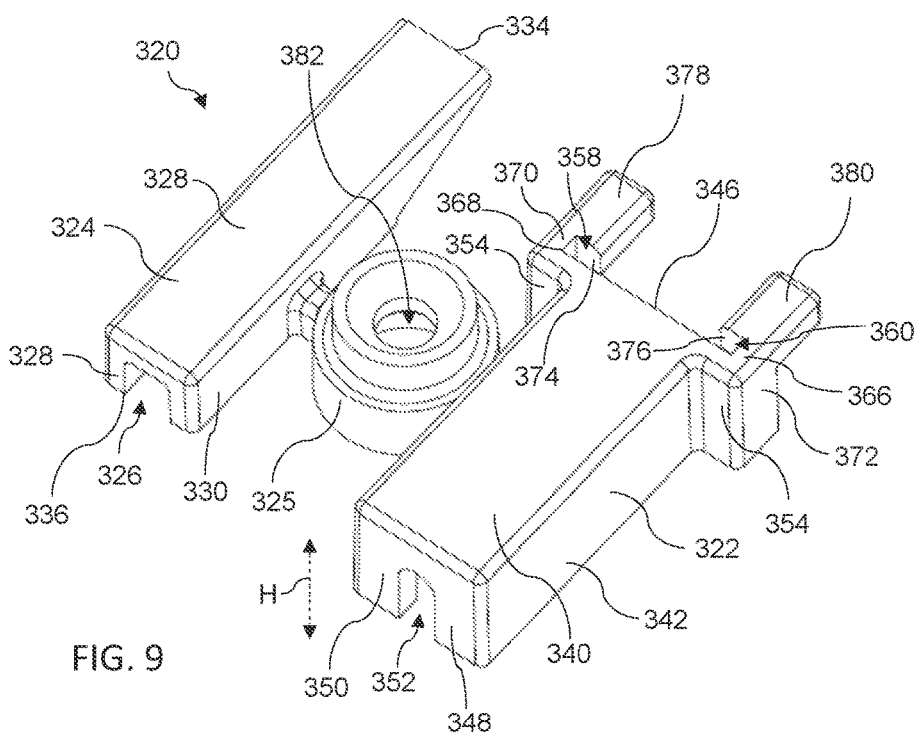
FIG. 9 is a front perspective view of a bracket in accordance with an embodiment of the present disclosure.
Figure 10:
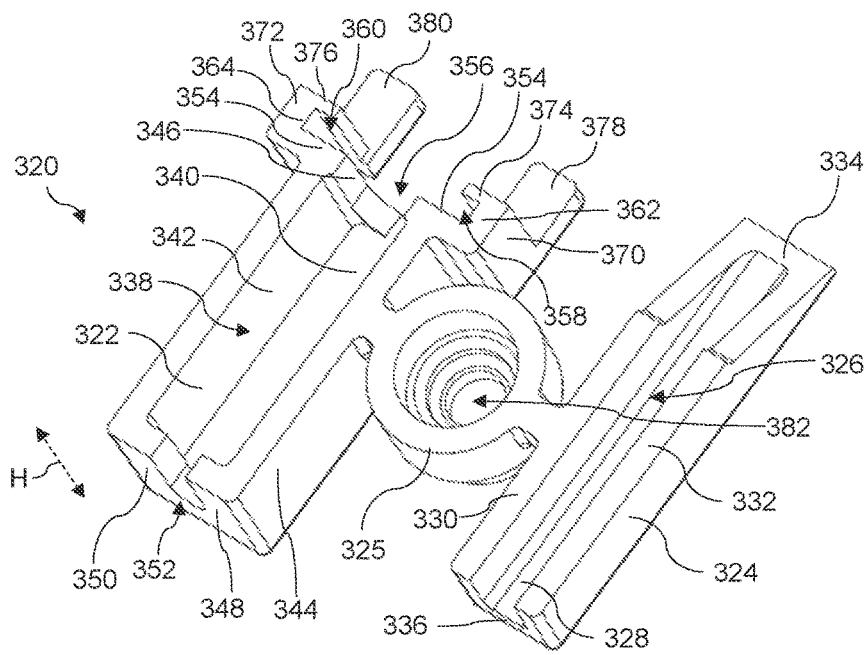
FIG. 10 is a rear perspective view of the bracket of FIG. 9.

A controller controls the light emitting elements 118 of the annular shape outer portion 128 and the inner round portion 130 to emit light to a region of interest (e.g., surgical treatment site or other medical site) below or proximate the light head 110. For example, a controller may control the light sources 118 of the annular shape outer portion 128 and the inner portion 130 to emit light to a region of interest below the light head 100. Control of the respective light sources 118 may be performed, for example, collectively, individually, in groups, by section, or in any other suitable manner. In some embodiments, the controller may be provided as part of the light head 110 such as shown in FIG. 8 where the controller is part of a camera assembly 182 within the handle 164 of the light head 110. In other embodiments, the controller may be implemented elsewhere in the medical device support system 100 external to the camera assembly 182, for example elsewhere in the light head 110 or external to the light head 110, or the controller may be implement external to the medical device support system 100.

With continued reference to FIG. 2, a plurality of collimators 136 are mounted to the inside surface 134 of the housing base 116 and in the light emitting paths of the respective plurality of light emitting elements 118. Each collimator may be associated with a respective light emitting element 118 and may be arranged such that at least a portion of the light emitted from the associated light emitting element 118 is incident a surface of the collimator. The collimators 136 collect and direct, and/or collimate, the light emitted from the associated light emitting element 118 into a narrowed beam. In one form, the collimators 136 may comprise total internal reflection (TIR) lenses. In some embodiments, the collimators 136 and associated light emitting elements 118 may be grouped together in modules 138, 140 mounted to the inside surface of the annular shape outer base 128, and one round module 142 mounted to the inside surface of the inner round base 130.

The housing cover 122 also includes the housing lens 124, which in the illustrative embodiment includes an annular shape outer cover 144 and an inner round cover 146. Both the annular shape outer cover 144 and an inner round cover 146 may be shaped to redirect light emitted from the light emitting elements and passing therethrough. In an alternate form, the housing cover 122 is configured such that one or both of the annular shape outer cover 144 and an inner round cover 146 are formed of a transparent non-lens material, i.e. a non-light bending material. In embodiments where both the annular shape outer cover 144 and an inner round cover 146 are formed of a transparent non-lens material, the housing lens 124 may be considered to be omitted from the light head 110.

FIG. 2 shows an axial arrangement of the light emitting elements 118, the collimators 136, the annular shape lens 120, and the housing lens 124, where axial refers to the direction of emission of light from the light head 110, or downward in FIG. 2. The annular shape outer cover 144 and the inner round cover 146 are in the light emitting paths of respective ones of the plurality of light emitting elements 118. The annular shape lens 120 is in the respective light emitting paths of respective ones of the plurality of light emitting elements 118, positioned between the light emitting elements 118 and the annular shape outer cover 144. Each collimator 136 is also arranged in the light emitting path of a respective light emitting element of the plurality of light emitting elements 118 in the annular shape outer portion 128 of the light head 110 positioned between the light emitting element 118 and the annular shape lens 120; or is arranged in the light emitting path of a respective light emitting element of the plurality of light emitting elements 118 in the inner round portion 130 of the light head 110 positioned between the light emitting elements 118 and the inner round cover 146.

The annular shape lens 120, the housing lens 124, and the collimators 136, if provided, can take on any form for spreading and/or bending the light emitted by the light emitting elements 118. As shown for example in FIG. 2, the inner round cover 146 of the housing lens 124 has a top face 152 formed as a stepped surface, for example a plurality of Fresnel wedges, that bends individual portions of the light beams, and a bottom face 154 formed as a generally planar surface. The annular shape lens 120 has a top face 156 formed as a stepped surface, for example a plurality of Fresnel wedges, that bends individual portions of the light beams, and a bottom face 158 formed as a wavy or curved surface that bends individual portions of the light beams. The annular shape outer lens 144 of the housing lens 124, has a top face 160 formed as a wavy or curved surface and a bottom face 162 formed as a generally planar wedge-shaped surface, where a generally planar wedge-shaped surface refers to a generally planar surface that is not perpendicular to the direction of travel of the light beam emitted by the light emitting elements 118 and collimators 136, for example.

With continued reference to FIGS. 1 and 2, the light head 110 includes a handle 164. In the exemplary embodiment, the handle 164 is rotatably mounted coaxially to a hub 166 of the light head 110. A lever 170 is provided for transferring rotational motion from the handle 164 to the annular shape lens 120. A first end 168 of the lever 170 is movably coupled to a bushing 172 of the handle 164 and a second end 174 of the lever 170 is movably coupled to the annular shape lens 120. The lever 170 is configured to transfer rotational motion of the handle 164 at the first end 168 of the lever 170 into rotational motion of the annular shape lens 120 at the second end 174 of the lever 170. It will be appreciated that in other embodiments, the handle 164 may be mounted in a stationary manner, although components within the handle 164, for example a camera assembly 182 described below, may be configured to rotate therein. Further details of an exemplary surgical light system suitable for the present application are described in U.S. application Ser. No. 17/151,760 filed Jan. 19, 2021, and titled "Lighthead with Rotating Lens Assembly and Method of Operating Same," which is incorporated by reference for all purposes as if fully set forth herein.

Figure 3:
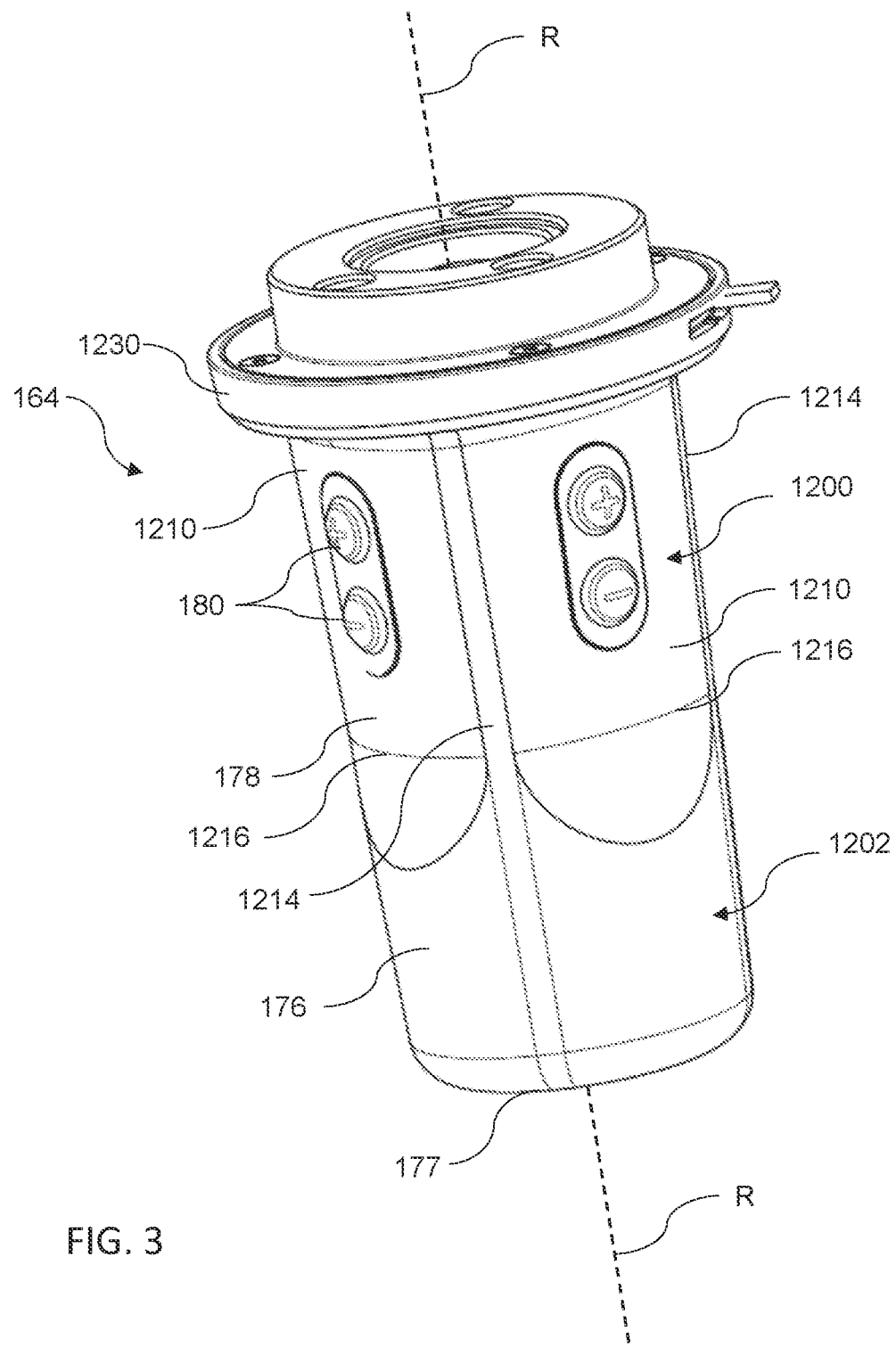
FIG. 3 is a perspective side view of a handle in accordance with an embodiment of the present disclosure having a handle housing including a grip portion.

FIGS. 3-6 show further details of the handle 164. FIG. 3 shows the handle 164 having the grip portion 178 of the handle housing 176 having buttons 180 that provide a user interface for the handle 164 for controlling attributes of the emitted light from the light head 110. In other embodiments, the handle 164 may be provided with buttons that interface with a drive motor to rotate the afore mentioned camera assembly 182 within the handle housing 176. The handle housing 176, including the grip portion 178 thereof, has a sufficient size to be gripped by a human hand meaning that the outermost diameter or perimeter of the handle housing 176 is selected to enable a human hand to be comfortably wrapped around the handle housing 176. The handle housing 176 may be cylindrical in shape and elongated along a rotation axis R. Other shapes may be suitable for the handle housing 176 as will be described in greater detail below.

Figure 4:
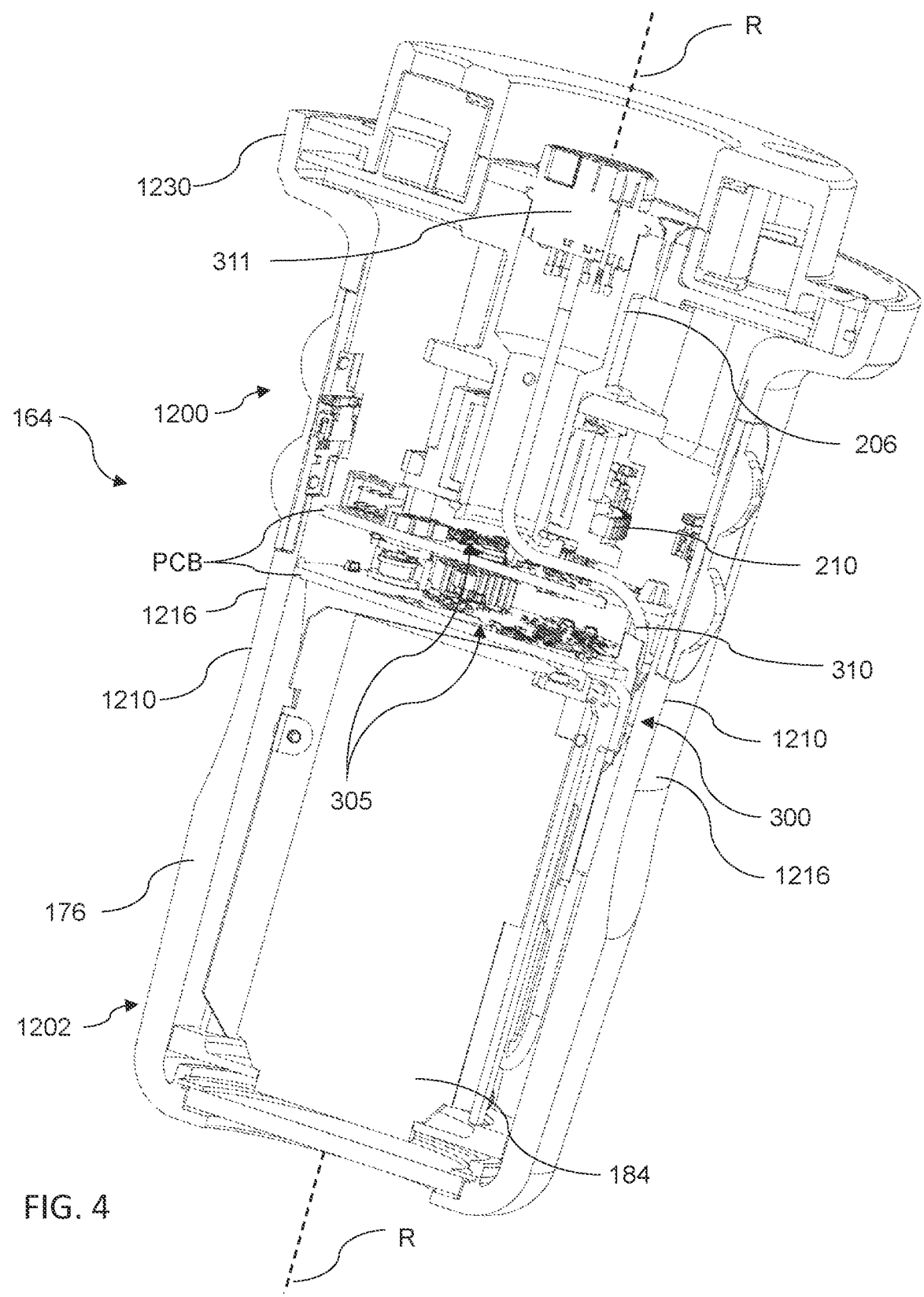
FIG. 4 is a perspective cross section view of the handle of FIG. 3.

FIG. 4 shows a perspective cross section view of the handle 164 and FIG. shows a perspective cross section view of the handle 164 with the handle housing 176 removed. The handle 164 includes a camera assembly 182 within the handle housing 176. The camera assembly 182 includes a camera 184 configured to capture images and/or video of a field of view 186, which may include a target. The target may constitute a region of interest.

Figure 7:
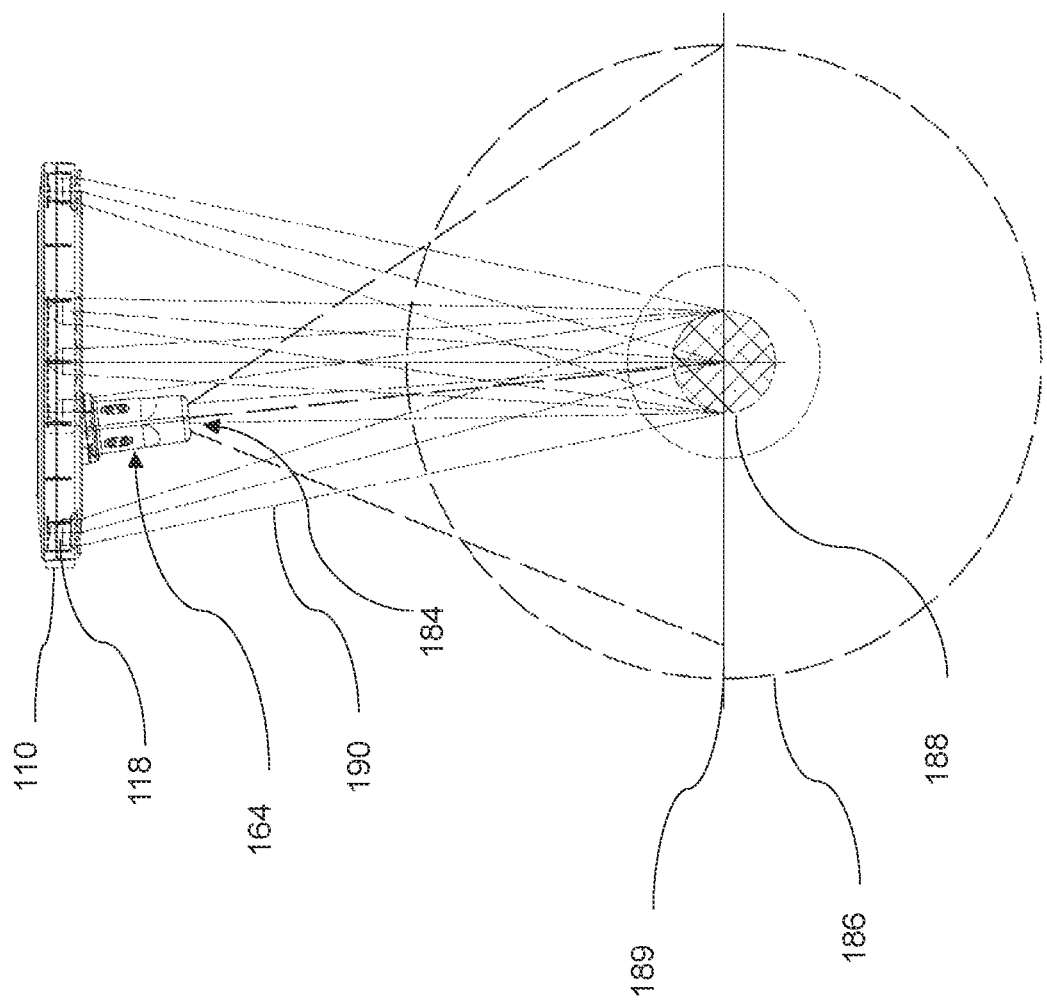
FIG. 7 shows a region of interest illuminated by a light head and a field of view of a camera in the handle of the light head.

As shown in FIG. 7, the region of interest 188 may at least partially be illuminated by light emitted by the plurality of light emitting elements 118. The region of interest 188 may include a specific target, such as a patient on a surgical table 189. A target may be defined as an area which the user intends to illuminate by aiming the light 190 produced by the surgical light. The region of interest 188 may in some embodiments be defined as the area that is illuminated by the light head 110. The region of interest 188 may be formed by the light emitting elements 118 that emit light and collimators and/or lenses that aim, redirect, spread, converge, and or focus the light. The light head may be arranged such that it is a predetermined distance from the region of interest. Adjustment of the light head relative to the region of interest may be performed using the extension arm 104, load balancing arm 106, and/or yoke assembly 108. In an example, the light head may be adjusted such that it is a distance of about one meter from the region of interest. "Target", "region of interest," "target region", and "target region of interest," etc. may be used with reference to the same area.

The camera 184 may include any suitable optical camera including a sensor and being configured to capture images within the region of interest 188. For example, the camera 184 may include a complementary metal oxide semiconductor (CMOS) sensor. Other sensors may be suitable. In an exemplary embodiment, a CMOS sensor having approximately a 2,000,000 pixel resolution, for example an HD camera, may be suitable. It will be appreciated that higher resolution cameras are also contemplated, for example, a 4K camera having for example approximately 9,000,000 pixel resolution, and still further an 8K camera having an even greater pixel resolution. The camera 184 may have any suitable focal distance range, such as between 10 and 1500 millimeters. In one embodiment, an 800 millimeter range may be suitable, for example, for full optical zoom. The camera 184 may have any suitable signal-to-noise ratio. The signal-to-noise ratio may exceed 50 decibels to provide clear images. As will be described in greater detail below, the optical video signal associated with video data captured by the camera 184 and output by the camera assembly 182 utilizes an optical fiber cable 310 that enables a high bandwidth data link so that advantageously the optical video signal is uncompressed, thereby mitigating for example issues such as visual compression artifacts, noise, and video latency. In another exemplary embodiment, the camera 184 may include a surgical display having a resolution that is approximately 4096 by 2160, an aspect ratio of 1.9 to 1, and a viewing angle that is approximately 178 degrees. The camera 184 may also include one or more lenses (not shown) to provide zooming and focusing functionality, as well as any other components to allow for operation of the camera 184. Many other cameras may be suitable.

Figure 5:
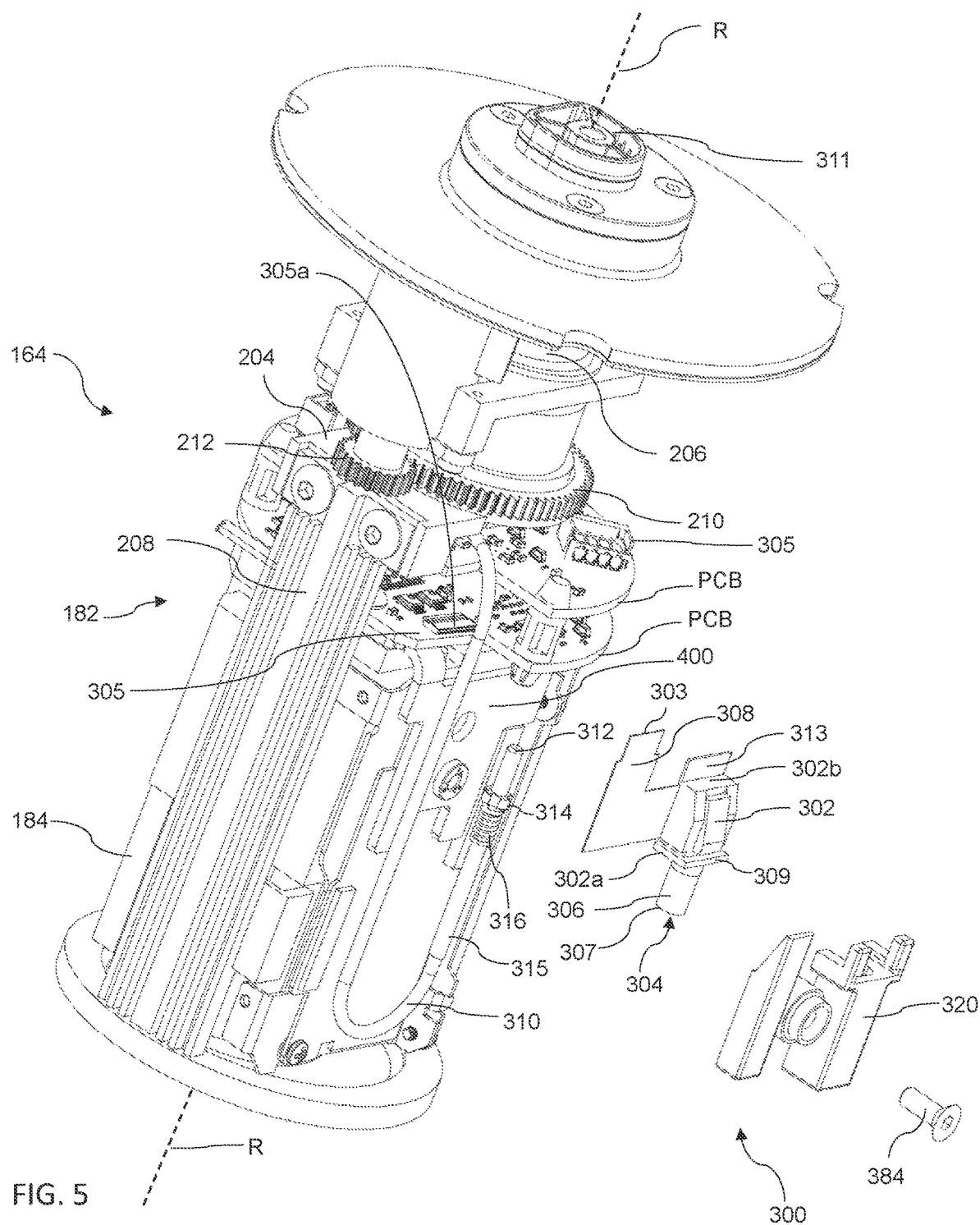
FIG. 5 is an exploded perspective view of parts of the handle of FIG. 3 with the handle housing removed.

Referring to FIG. 8, the camera assembly 182 is configured to output an optical video signal pertaining to images and/or video captured by the camera 184 within the field of view 186 and the region of interest 188. The optical video signal may be output from the camera assembly 182 to elsewhere in the medical device support system 100. As will be described in greater detail below, the camera assembly 182 may include a control system 192 that processes image data captured from the camera 184. The control system 192 may be located in the handle housing 176, for example as part of the camera assembly 182 as shown in FIGS. 5 and 8, or in the light head housing 116, 122 of the light head 110, or outside of the light head housing 116, 122, or even outside of the medical device support system 100, or may be located in a combination of two or more of the handle housing 176, the light head housing 116, 122, outside of the light head housing 116, 122, and outside of the medical device support system 100. In the illustrative embodiment, and as will be described in greater detail below, the control system 192 components, i.e. controller 194, processor 196, memory 198, and video processing circuit 200, are part of control electronics 305 of the camera assembly 182. As will also be described below, the control system 192 may be configured to control other components, such as a video display monitor, of the medical device support system 100 in addition to the camera assembly 182.

The control system 192 may include a controller 194 that is configured to carry out overall control of the functions and operations of the control system 192. The controller 194 may include a processor 196, such as a central processing unit (CPU), microcontroller, or microprocessor. The processor 196 executes code stored in a memory (not shown) within the controller 194 and/or in a separate memory, such as the memory 198, in order to carry out operation of the control system 192.

The controller 194 may be coupled to a video processing circuit 200. The video processing circuit 200 may process communications (COMM), power, and a low voltage differential signaling (LVDS) video signal 201*a* from the camera 184 to create a High-Definition Multimedia Interface (HDMI) format electrical video signal 201*b*, which electrical video signal may then be processed by a fiber module 302 into an optical video signal 201*c* used to drive a display 202, for example a display monitor. The fiber module 302 may constitute part of the camera assembly 182 as shown in block diagram in FIG. 8, or may be mounted to the camera assembly 182 as described in greater detail below.

The video processing circuit 200 may also be configured to convert image and/or video data to an image and/or video signal used to drive the display 202. The video processing circuit 200 may include any appropriate buffers, decoders, video data processors and so forth. The optical video signal of the camera assembly 182 may be processed by the controller 194 and/or converted by the video processing circuit 200 and may be displayed on the display 202. The optical video signal of the camera assembly 182 may also or alternatively be stored on a memory, such as the memory 198. The stored image(s) and/or video may be displayed on the display at a later time.

The display 202 may be used to present images and/or video to a user (e.g., healthcare professional or other individual), as well as any other graphics or information to the user. The display may be a lighted display. In some embodiments, the display 202 is a backlit liquid-crystal display (LCD). The LCD may be backlit using one or more suitable light sources (e.g., a light emitting diode (LED), cold cathode fluorescent (CCFL), etc.). In other embodiments, the display 202 is an organic light-emitting diode (OLED) display.

With continued reference to FIGS. 2 and 4-6, the camera assembly 182 may be configured for rotation about the rotation axis R in both a clockwise direction and in a counterclockwise direction. The camera assembly 182 includes a bracket 204, a spindle 206, and an axially extending bracket 208. The spindle 206 is fixed relative to the handle housing 176 of the handle 164. The bracket 204 is rotatably mounted to the spindle 206 and is fixed to the axially extending bracket 208. In the illustrative embodiment, the brackets 204, 208 together form a rotatable bracket 204, 208 having an inverted L shape. The rotatable bracket 204, 208 provides for rotation of the camera 184 within the handle housing 176 (e.g., rotation about the rotation axis R). A gear 210 is fixed to the bracket 204 and a pinion 212 is in meshing engagement with the gear 210 for driving the gear 210 and thus the rotatable bracket 204, 208 to rotate the camera 184. The camera assembly 182 may in some embodiments be configured for rotation that is greater than 360 degrees about the rotation axis R in both a clockwise direction and in a counterclockwise direction. Further details of an exemplary means of providing rotational capability of the camera assembly 182 within the handle housing 176 is described in U.S. Provisional Application No. 63/000,655 filed Mar. 27, 2020, titled "360 Degrees Plus Rotation Module for Surgical Light Head Handle," which is incorporated by reference for all purposes as if fully set forth herein. Many other rotation assemblies, if included, may be suitable.

The camera assembly 182 of the present disclosure may include a fiber optic assembly 300 that provides fiber optic capability integrated into the light head handle 164 for transmission of the optical video signal associated with video data captured by the camera 184 from a location within the handle 164 to the light head housing 116, 122. In some embodiments, the optical video signal may also be transmitted from the light head housing 116, 122 to elsewhere in the medical device support system 100.

Figure 6:
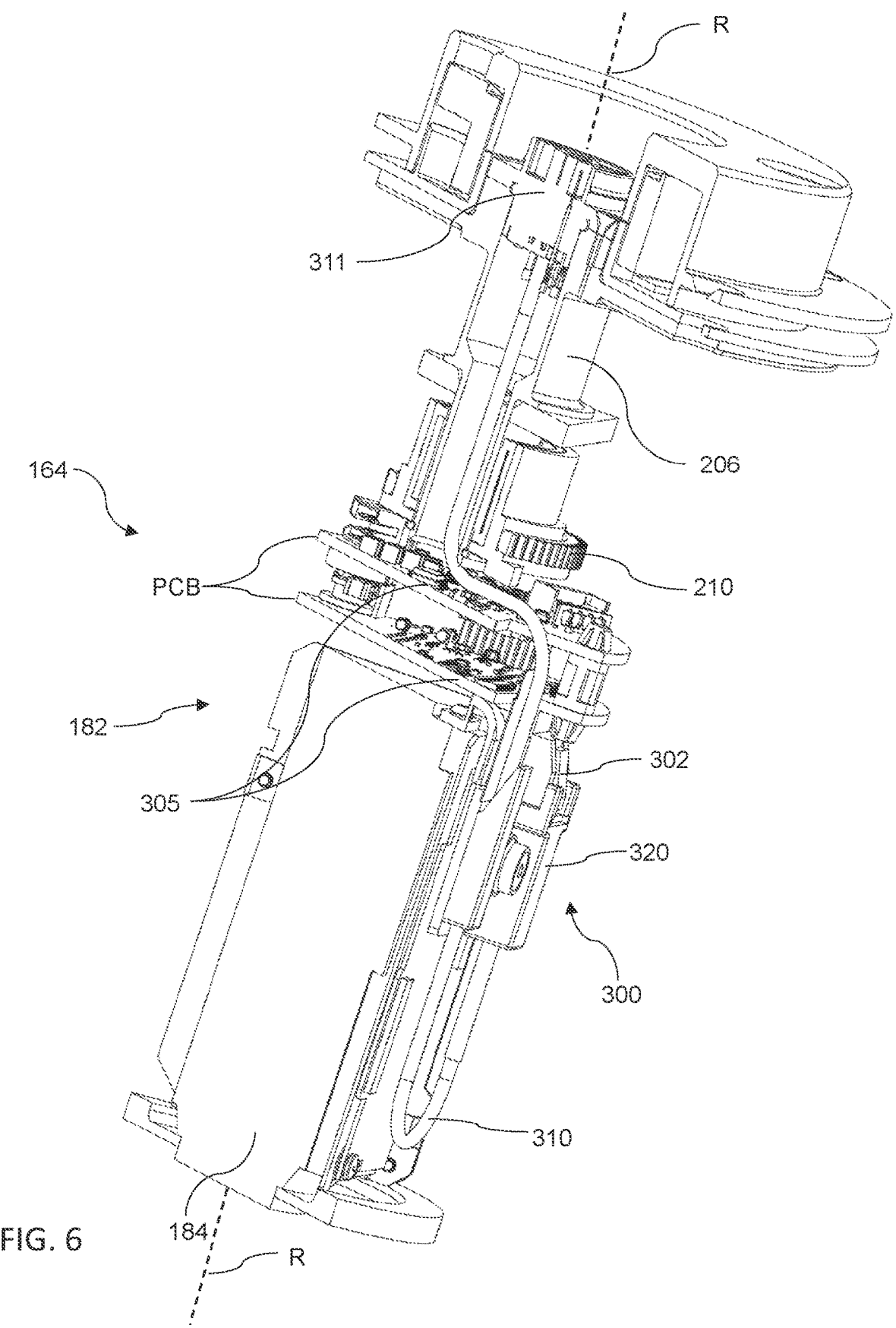
FIG. 6 is a perspective cross section view of parts of the handle of FIG. 3 with the handle housing removed.

With reference to FIGS. 5 and 6, the fiber optic assembly 300 includes a fiber module 302 located within the handle housing 176 and coupled to the camera assembly 182, for example, coupled to a heat transfer plate 400 thereof, as will be described in greater detail below. The fiber module 302 is configured to convert electrical video signals of video data captured by the camera 184 into optical video signals. The fiber module 302 includes an optical video signal transmission port 304. A tubular interface member 306 is coupled to the optical video signal transmission port 304 and is configured to mate with an optical fiber cable 310.

In the illustrated embodiment, a flexible ribbon cable 308 is coupled to the fiber module 302. An opposite end 303 of the flexible ribbon cable 308 (that is, the end 303 opposite to where the flexible ribbon cable 308 is coupled to the fiber module 302) may be connected to the camera assembly 182, for example, control electronics 305 such as a printed circuit board (PCB) of the camera assembly 182. For example, the opposite end 303 of the flexible ribbon cable 308 can be plugged into a connector 305a of the control electronics 305. In the illustrative embodiment, the control electronics 305 are positioned axially between the camera 184 and the gear/pinion arrangement 210, 212 of the camera assembly 182. In some embodiments, the control electronics 305 may be positioned axially between the camera 184 and the accessory port connector 311 in a position axially above the gear/pinion arrangement 210, 212. In the illustrative embodiment, the control electronics 305 include the components of the control system 192, i.e. the controller 194, processor 196, memory 198, and video processing circuit 200. The camera 184 may be configured to transmit communications (COMM), power, and a low voltage differential signaling (LVDS) video signal for example 201a in FIG. 8 to the control electronics 305. The control electronics 305, for example the video processing circuit 200 of the control system 192 of the control electronics 305, may process the video signal to create a High-Definition Multimedia Interface (HDMI) format electrical video signal for example 201b in FIG. 8 that is transmitted via for example the connector 305a to the flexible ribbon cable 308. The fiber module 302 then converts the HDMI electrical video signal to an HDMI optical video signal for example 201c in FIG. 8.

Referring to FIG. 6, any heat radiated by the fiber module 302 may be transferred to and dissipated by the heat transfer plate 400, as will be described in greater detail below. As shown in FIG. 5, and FIGS. 13-15 to be described in greater detail below, a heat transfer pad 313 may be sandwiched between the fiber module 302 and the heat transfer plate 400 the length of the fiber module 302, that is, to axially opposite ends 302a, 302b of the fiber module 302, and slightly beyond the end 302b. The heat transfer pad 313 may be made of any suitable compressible material, for example, a silicone polymer material, or other conformable, thermally conductive material for filling air gaps, including gap fillers, thermal pads, form-in-place pads, sil pads, among others. The fiber module 302 may be mounted to the heat transfer plate 400 by a clamping force of the bracket 320, with the heat transfer pad 313 (if provided) compressed therebetween.

The fiber optic assembly 300 further includes an optical fiber cable 310. The optical fiber cable 310 may transmit optical images and/or video signals, for example the afore described HDMI optical video signal 201c, associated with image and/or video data captured by the camera 184. In the illustrative embodiment, the optical fiber cable 310 transmits the optical video signals from the fiber module 302 to elsewhere in the medical device support system 100. The optical fiber cable 310 provides a high bandwidth data link suitable for the optical video signal output associated with the afore mentioned camera 184, whether an HD camera, 4K camera or even 8K camera. In an exemplary embodiment, the optical fiber cable 310 provides a high bandwidth capability for the optical video signal to be uncompressed, thereby mitigating for example issues such as visual compression artifacts, noise, and video latency. With reference to FIG. 8, in some embodiments, the optical fiber cable 310 may be configured to provide a bidirectional control signal or data/COMM link that links the control electronics 305 (in the illustrative embodiment the control system 192) to for example intelligent display devices. Thus, the optical fiber cable 310 may provide a unidirectional control signal in that the optical fiber cable 310 provides an optical video signal to drive for example display 202. The optical fiber cable 310 may provide a bidirectional control signal in that the optical fiber cable 310 provides receive/transmit control signals between the display 202 and the control electronics 305.

The optical fiber cable 310 extends from a location within the handle housing 176, in the illustrative embodiment the location at which the optical fiber cable 310 is attached to the fiber module 302, to the light head housing 116, 122. From the light head housing 116, 122, the optical fiber cable 310 may extend to additional components within the light head housing 116, 122 and/or to, for example, the coupling member 112, the yoke assembly 108, the load balancing arm 106, the extension arm 104, the support column 102, or elsewhere in the medical device support system 100. Additionally, or alternately, and with reference to FIGS. 4-6, 14 and 15, the optical fiber cable 310 may be coupled to a suitable handle-to-light head housing accessory port connector 311 in the light head housing 116, 122, for example at the location where the handle 164 is rotatably mounted coaxially to the hub 166 of the light head 110, and another optical fiber cable may extend from such accessory port connector 311 to additional components within the light head housing 116, 122 and/or to, for example, the coupling member 112, the yoke assembly 108, the load balancing arm 106, the extension arm 104, the support column 102, or elsewhere in the medical device support system 100. In the illustrative embodiment, the accessory port connector 311 integrates an electrical cable connection with the optical fiber cable 310 connection so that electrical signals, for example electrical power and/or electrical data signals, may be transmitted from the light head housing 116, 122, or from elsewhere in the medical device support system 100, to the handle 164 and the camera assembly 182 therein, or vice versa. Other embodiments are also contemplated.

The optical video signal is transmitted via the optical fiber cable 310 and/or any additional or alternate cables, to elsewhere in the medical device support system 100, for example, the display 202. As noted above, the control system 192 for controlling components such as the display 202 may be located in the handle housing 176, for example as part of the camera assembly 182 as shown in FIGS. 5 and 8, or in the light head housing 116, 122 of the light head 110, or outside of the light head housing 116, 122, or even outside of the medical device support system 100, or may be located in a combination of two or more of the handle housing 176, the light head housing 116, 122, outside of the light head housing 116, 122, and outside of the medical device support system 100. Accordingly, the optical fiber cable 310 and/or additional or alternate cables may extend through other components of the medical device support system 100, for example, through the yoke assembly 108, load balancing arm 106, extension arm 104, and support column 102.

In an assembled state, the distal end 312 of the optical fiber cable 310 is optically coupled to the fiber module 302. Optical image and/or video signals from the fiber module 302 are input from the optical video signal transmission port 304 to the distal end 312 of the optical fiber cable 310. The optical fiber cable 310 includes a ferrule 314 and a biasing member 316 proximate the distal end 312 of the optical fiber cable 310. As described below, the ferrule 314 and a biasing member 316 may assist in aligning and retaining the distal end 312 of the optical fiber cable 310 with the optical video signal transmission port 304 in a predetermined arrangement.

The fiber optic assembly 300 further includes a bracket 320. The bracket 320 is mounted to one or more components of the camera assembly 182 within the handle housing 176. In the illustrative embodiment, the bracket 320 is mounted to the heat transfer plate 400 of the camera assembly 182. The bracket 320 may alternatively or additionally be mounted to the control electronics 305 such as the printed circuit board (PCB) of the camera assembly 182. Referring again to FIG. 5, the fiber module 302 may be sandwiched between the bracket 320 and the heat transfer plate 400, with the heat transfer pad 313, if present, sandwiched between the fiber module 302 and heat transfer plate 400. The heat transfer plate 400 may then be attached to the rotatable bracket 204, 208; that is, the heat transfer plate 400 may be attached to the bracket 204 and/or the bracket 208. In the illustrative embodiment, the fiber module 302 is positioned along the body of the camera 184, that is, disposed laterally to the side of and in spaced relationship relative the camera 184 radially outward from the rotation axis R of the camera 184, and between the camera 184 and the inner perimeter of the handle housing 176. Further, in the illustrative embodiment, the fiber module 302 is not connected to the camera 184 itself but rather to one or more brackets 204, 208 to which the camera 184 also is connected. In some embodiments, the fiber module 302 may be co-located with the control electronics 305 of the camera assembly 182 and/or positioned axially above the camera 184.

The bracket 320 retains the fiber module 302 in a fixed position relative to the camera 184. In the embodiment shown, the bracket 320 retains the fiber module 302 in an orientation such that the optical video signal transmission port 304 is arranged toward the distal end 177 of the handle 176. The bracket 320 also retains the distal end 312 of the optical fiber cable 310 in a fixed position relative to the camera 184 and relative to the fiber module 302 and optical video signal transmission port 304.

With additional reference to FIGS. 9-12, the bracket 320 includes an interface retention portion 322 and a cable retention portion 324. A fastening member 325 is located between and connects or bridges the interface retention portion 322 and the cable retention portion 324.

The cable retention portion 324 of the bracket 320 is configured as a channel 326 including a bottom wall 328 and side walls 330, 332. The channel 326 extends between a proximal end 334 and a distal end 336 along a direction C. The side walls 330, 332 extend in a height direction H from the bottom wall 332. The fastening member 325 is connected to one of the side walls 330 of the channel 326. In the exemplary embodiment shown, the side walls 330, 332 at the proximal end 334 are tapered. In other embodiments, the side walls 330, 332 have a constant height between the proximal end 334 and the distal end 336. The cable retention portion 324 may also be referred to as a guide channel in that it guides the optical fiber cable 310 within the handle housing 176 and toward the light head housing 116, 122.

The interface retention portion 322 of the bracket 320 includes an interface channel 338 including a bottom wall 340 and side walls 342, 344. The interface channel 338 extends between a proximal end 346 and a distal end 348 along a direction B. The side walls 342, 344 extend in a height direction H from the bottom wall 340. A distal wall 350 is located at the distal end 348 of the interface channel 338 and extends between the side walls 342, 344 and in the height direction H. The distal wall 350 is arranged orthogonal to the side walls 342, 344 of the interface channel 338. A slot 352 is provided in the distal wall 350 that provides for fluid communication through the distal wall and into the interface channel 338.

A proximal wall 354 is located at the proximal end 346 of the interface channel 338 and extends between the side walls 342, 344 and in the height direction H. The proximal wall 354 is arranged orthogonal to the side walls 342, 344 of the interface channel 338. A slot 356 is provided in the proximal wall 354 that provides for fluid communication through the proximal wall 354 and into the interface channel 338.

At each end of the proximal wall 354 a fiber module retention channel 358, 360 extends along the height direction H between a proximal end 362, 364 and a distal end 366, 368. Each fiber module retention channel 358, 360 includes a bottom wall 370, 372 and side walls 354, 374, 376, wherein a portion of the distal wall 354 forms a side wall of each of the fiber module retention channels 358, 360.

Retention walls 378, 380 extend from the side walls 374, 376 of each fiber module retention channel 358, 360. The retention walls 378, 380 extend from the side wall 374, 376 at the distal ends 366, 368 of the fiber module retention channels 358, 360. In the illustrative embodiment, each retention wall 378, 380 is oriented parallel to the bottom wall 340 of the interface channel 338.

The fastening member 325 includes an orifice 382 (e.g., a bolt hole) through which a fastener 384 (e.g., screw, rivet, etc.) may be inserted for securing the bracket 320 to another member, such as the heat transfer plate 400 or other component of the camera assembly 182. It will be appreciated that the fastening member 325 may include any suitable coupling mechanism and arrangement to fix the bracket 320 to the camera assembly 182. For example, in some embodiments, the fastening member 325 may include a bolt hole pattern through which fasteners (e.g., screws, rivets, etc.) may be respectively inserted for securing the bracket 320. In other embodiments, the fastening member 325 may have an arrangement of one or more tabs configured to mate with one or more orifices on the camera 184 or other component(s) of the camera assembly 182. In other embodiments, the fastening member 325 may have a surface that may be adhered to a surface of a component of the camera assembly 182 by an adhesive.

In the illustrative embodiment, the interface retention portion 322 and cable retention portion 324 are arranged such that the channel 326 of the cable retention portion 324 and the interface channel 338 of the interface retention portion 322 are parallel to one another in a direction orthogonal to the height direction H. In other embodiments, the interface retention portion 322 and cable retention portion 324 are arranged such that the channel 326 of the cable retention portion 324 and the interface channel 338 of the interface retention portion 322 are arranged non-parallel to one another in a direction orthogonal to the height direction H.

As shown in FIGS. 5 and 6, the bracket 320 may be secured to the camera assembly 182 and may retain the fiber module 302 in optical communication with the distal end 312 of the optical fiber cable 310. With additional reference to FIGS. 13-15, the distal end of the optical fiber cable 310 may be inserted into the tubular member 306 of the fiber module 302. The distal end 312 of the optical fiber cable 310 may be set at a predetermined distance from the output (e.g., lens) of the optical video signal transmission port 304. This distance may be set based on the length of the tubular member 306 and the position of the ferrule 314 on the optical fiber cable 310 relative to the distal end 312 of the optical fiber cable 310. The outer diameter of the ferrule 314 may be larger than the inner diameter of the tubular member 306 such that ferrule 314 contacts the distal end 307 of the tubular member 306 and prevents the optical fiber cable 310 from being inserted any further into the tubular member 306. In some embodiments, the position of the ferrule 314 is on the optical fiber cable 310 is adjustable. The predetermined distance between the distal end 312 of the inserted optical fiber cable 310 and the output (e.g., lens) of the optical video signal transmission port 304 may be any suitable distance. In some embodiments, the distance ranges from 0.1 mm to 1 cm. In other embodiments, the distance is less than 0.1 mm. It will also be appreciated that in some embodiments, the distal end 312 of the inserted optical fiber cable 310 may be in contact with the output of the optical video signal transmission port 304 such that the distance is zero mm.

The tubular member 306 defines an aperture at which the ferrule 314 seats to align the distal end 312 of the optical fiber cable 310 with an optical video signal transmission port 304 of the fiber module 302. In some embodiments, the ferrule 314 seats at the distal end 307 of the tubular member 306 to laterally align the optical fiber cable 310 with an axis of the optical video signal transmission port 304 of the fiber module 302. In other embodiments, the ferrule 314 seats at the tubular member 306 to angularly align the optical fiber cable 310 with an axis of the optical video signal transmission port 304 of the fiber module 302.

The fiber module 302 includes a flange 309 that slidably fits into the fiber module retention channels 358, 360. With the flange 309 inserted in the fiber module retention channels 358, 360, the fiber module 302 is restricted in movement in a direction along the direction B of the interface channel. The flange 309 of the fiber module 302 is inserted into the fiber module retention channels 358, 360 from a direction proximate the open top surface of the channel, and the retention walls 378, 380 prevent the fiber module 302 from extending past a predetermined position along the height direction H.

A biasing member 316 is provided on the optical fiber cable 310 at a side of the ferrule 314 opposite the distal end 312 of the optical fiber cable 310. In the exemplary embodiment shown, the biasing member 316 is a spring 316. In other exemplary embodiments, the biasing member 316 is a compressible, resilient material such as a rubber, foam, and the like. When the fiber module 302 and optical fiber cable 310 are inserted into the interface retention portion 322 of the bracket 320, one end of the biasing member 316 is in contact with the ferrule 314 and the other end of the biasing member 316 is in contact with the distal wall 350. The biasing member 316 provides a continuous biasing force against the ferrule 314 to retain the ferrule 314 against the distal end 317 of the tubular member 306, thereby retaining the distal end 312 of the optical fiber cable 310 in the predetermined position relative to the output (e.g., lens) of the optical video signal transmission port 304 of the fiber module 302.

In some embodiments, a sheath 315 may be provided around the optical fiber cable 310 proximate the distal end 312 of the optical fiber cable 310. In the embodiment shown, the ferrule 314 and biasing member 316 are disposed between the distal end 312 of the optical fiber cable 310 and the sheath 315. The sheath 315 may also pass through the slot 352 in the distal wall 350. The sheath 350 may provide a stiffness that inhibits or prevents the optical fiber cable 310 from bending or increases the optical fiber cable's resistance to bending proximate the distal wall 350.

When secured to the camera assembly 182, the retention walls 378, 380 hold the fiber module 302 against the camera assembly 182; and the distal wall 350, proximal wall 354, and/or bottom surface 340 of the interface channel and bottom surface of the interface channel hold the distal end 312 of the optical fiber cable 310 against the camera assembly 182.

Figure 13:
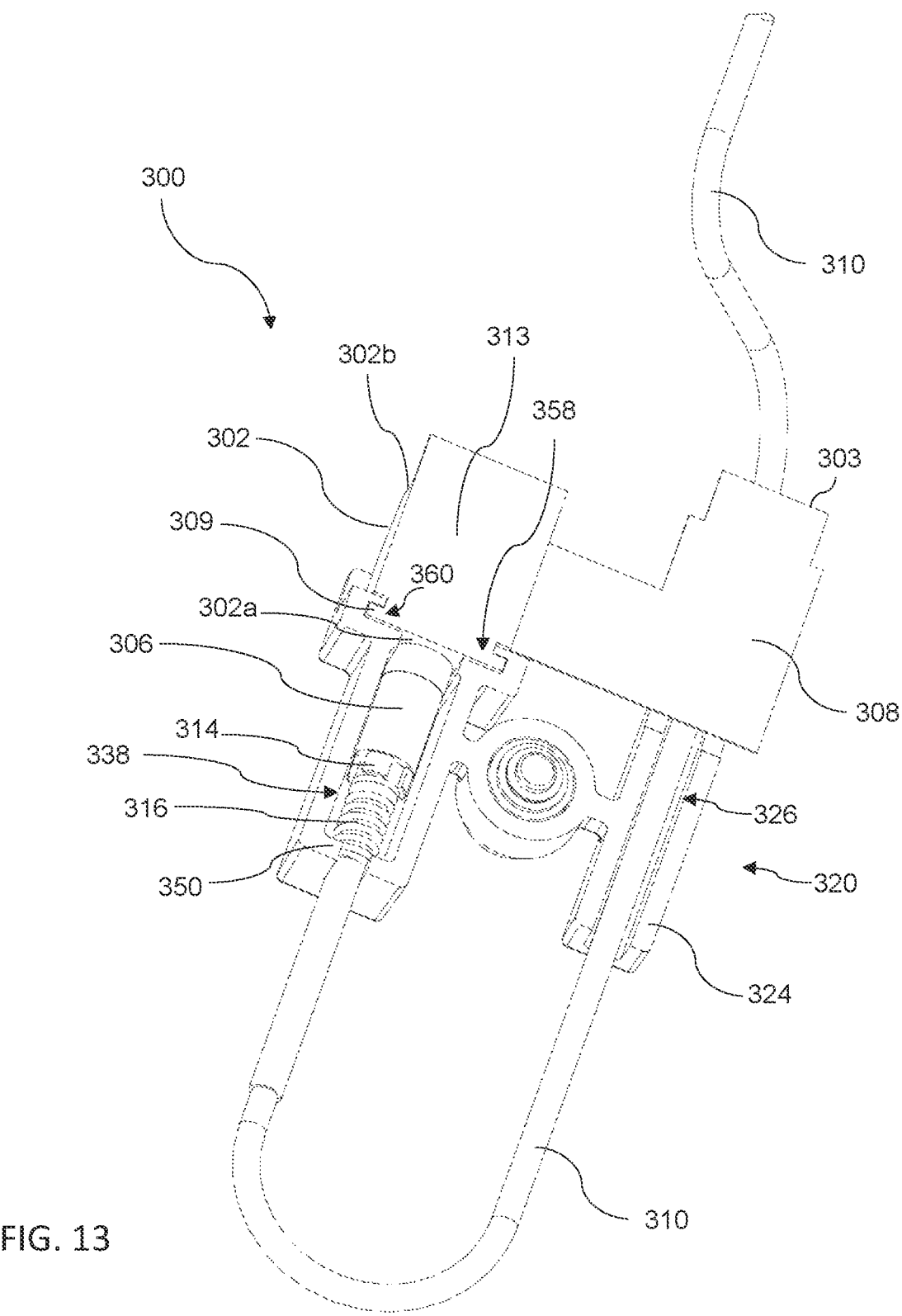
FIG. 13 is a rear perspective view showing the bracket of FIG. 9 and parts of a fiber optic assembly.
Figure 14:
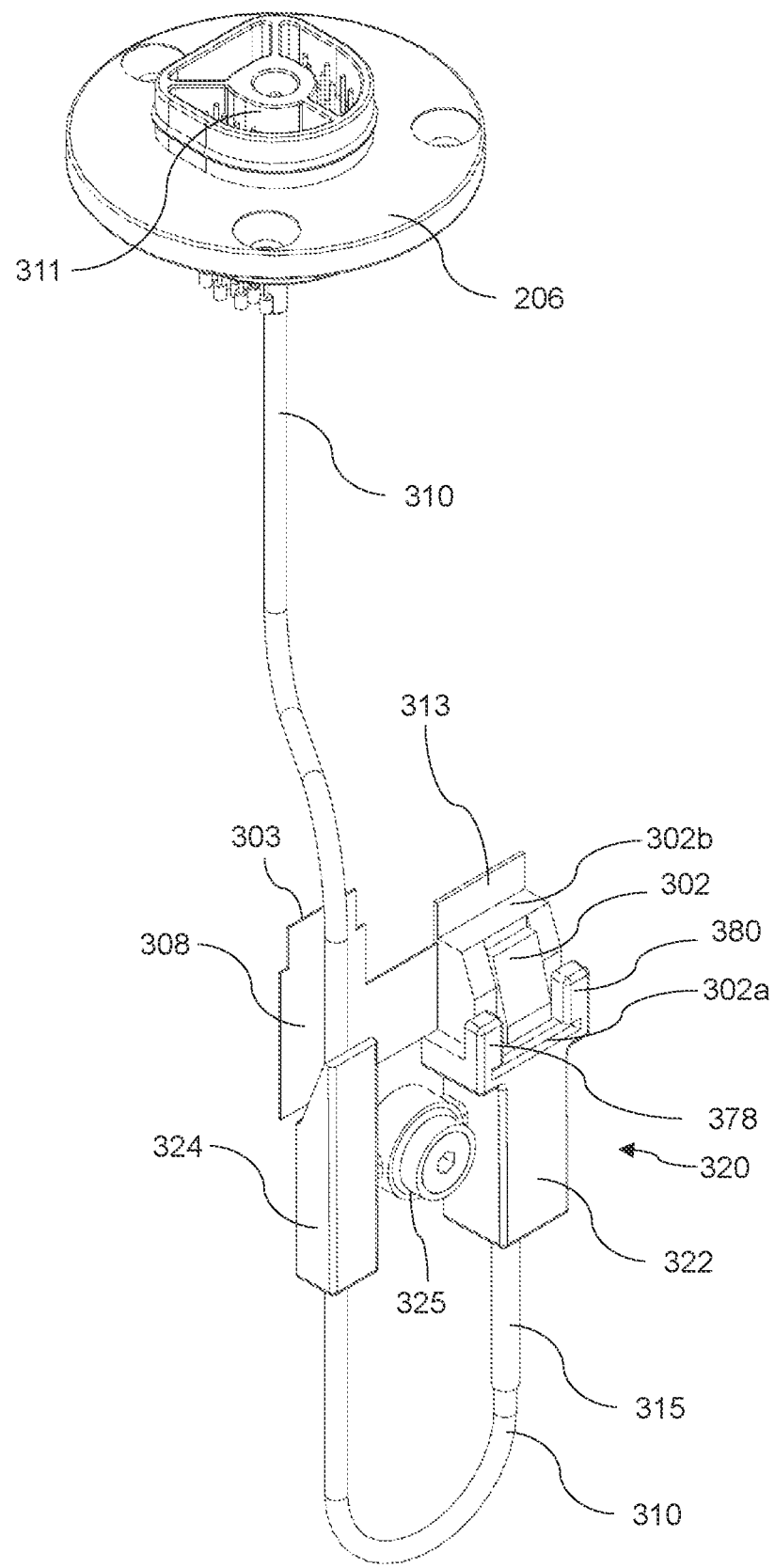
FIG. 14 is a front perspective view showing the bracket of FIG. 9 and parts of a fiber optic assembly and handle.
Figure 15:
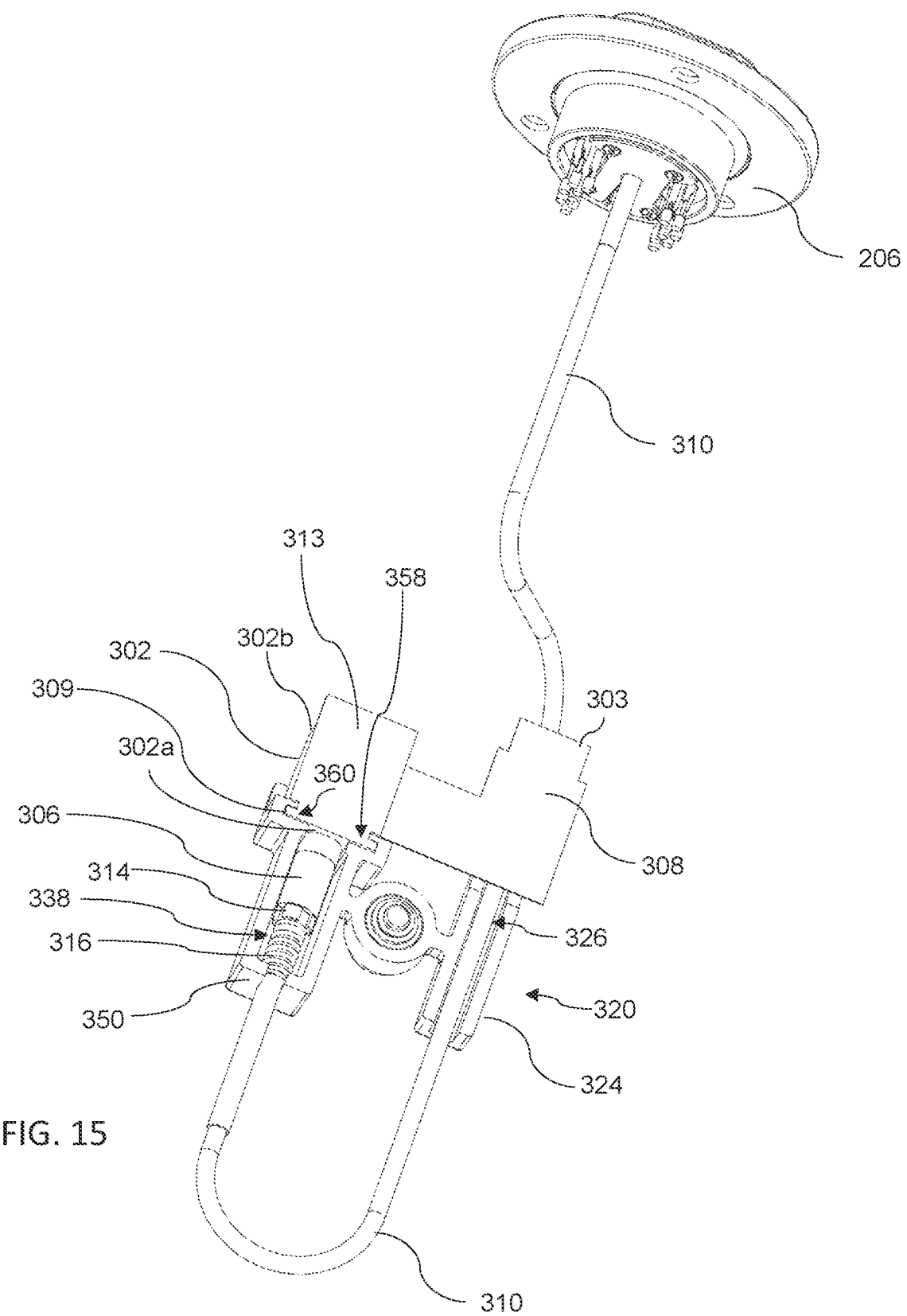
FIG. 15 is a rear perspective view showing the bracket and parts of the fiber optic assembly and handle.
Figure 16:
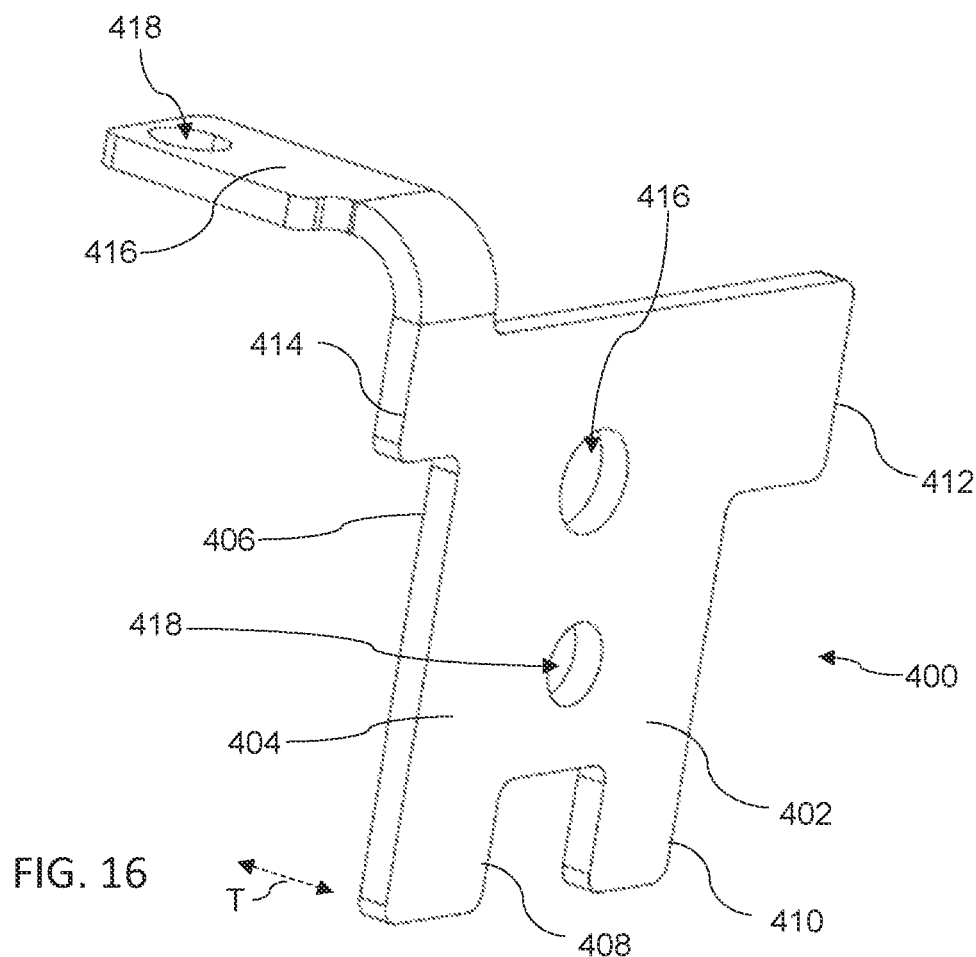
FIG. 16 is a front perspective view of a heat transfer plate in accordance with an embodiment of the present disclosure.
Figure 17:
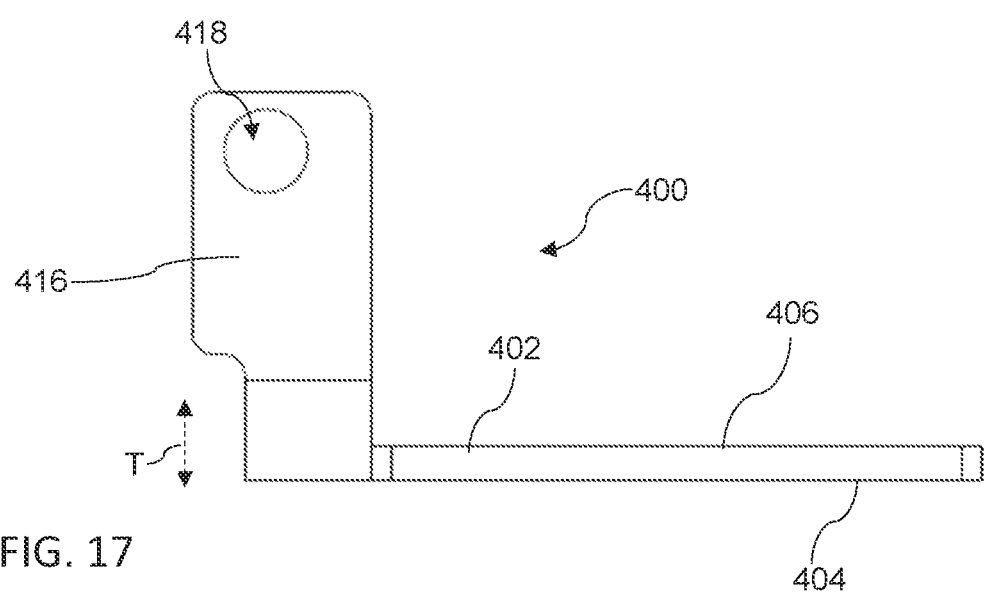
FIG. 17 is a top view of the heat transfer plate of FIG. 16.
Figure 18:
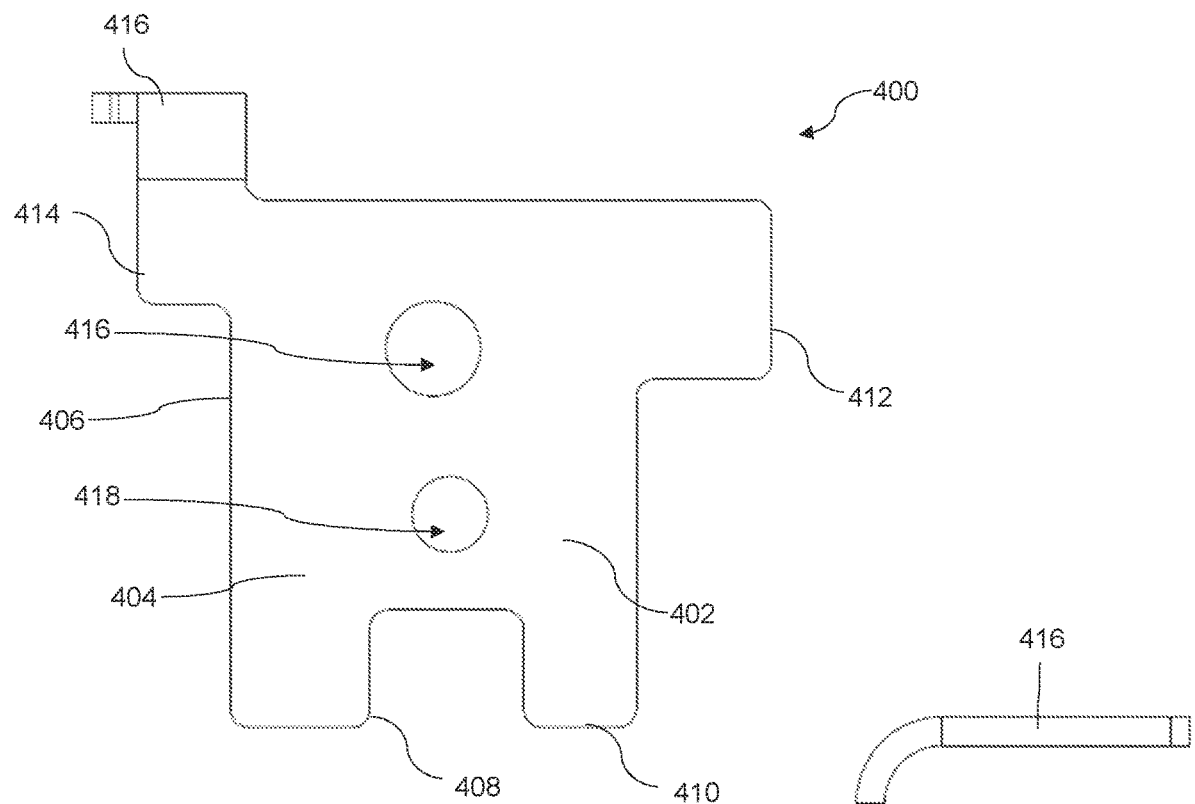
FIG. 18 is a front elevation view of the heat transfer plate of FIG. 16.
Figure 19:
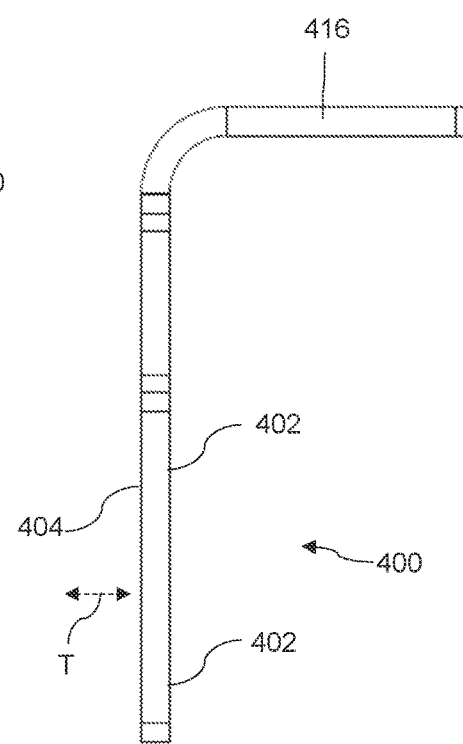
FIG. 19 is a side elevation view of the heat transfer plate of FIG. 16.
Figure 20:
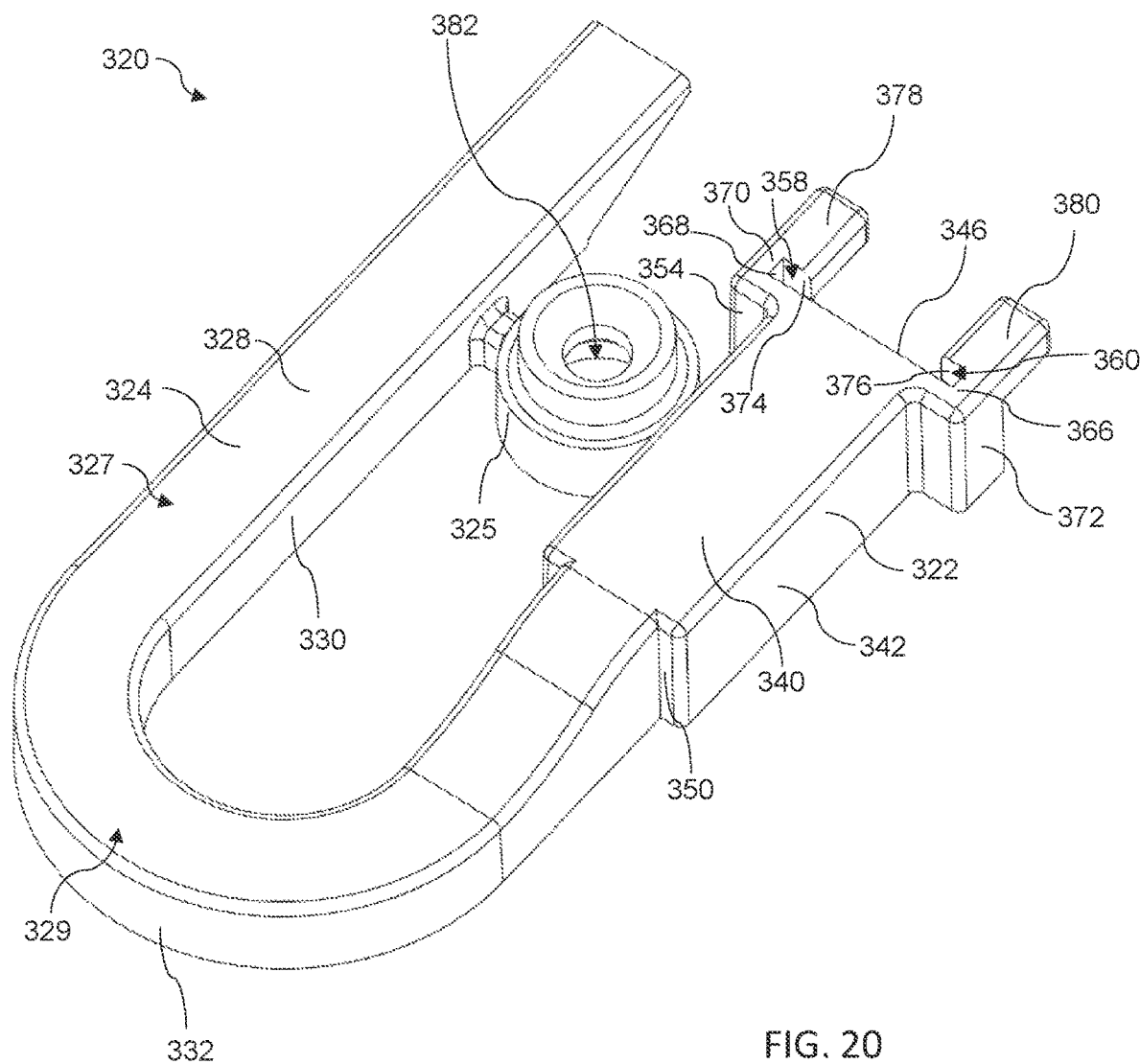
FIG. 20 is a front perspective view of a bracket in accordance with another embodiment of the present disclosure.
Figure 21:
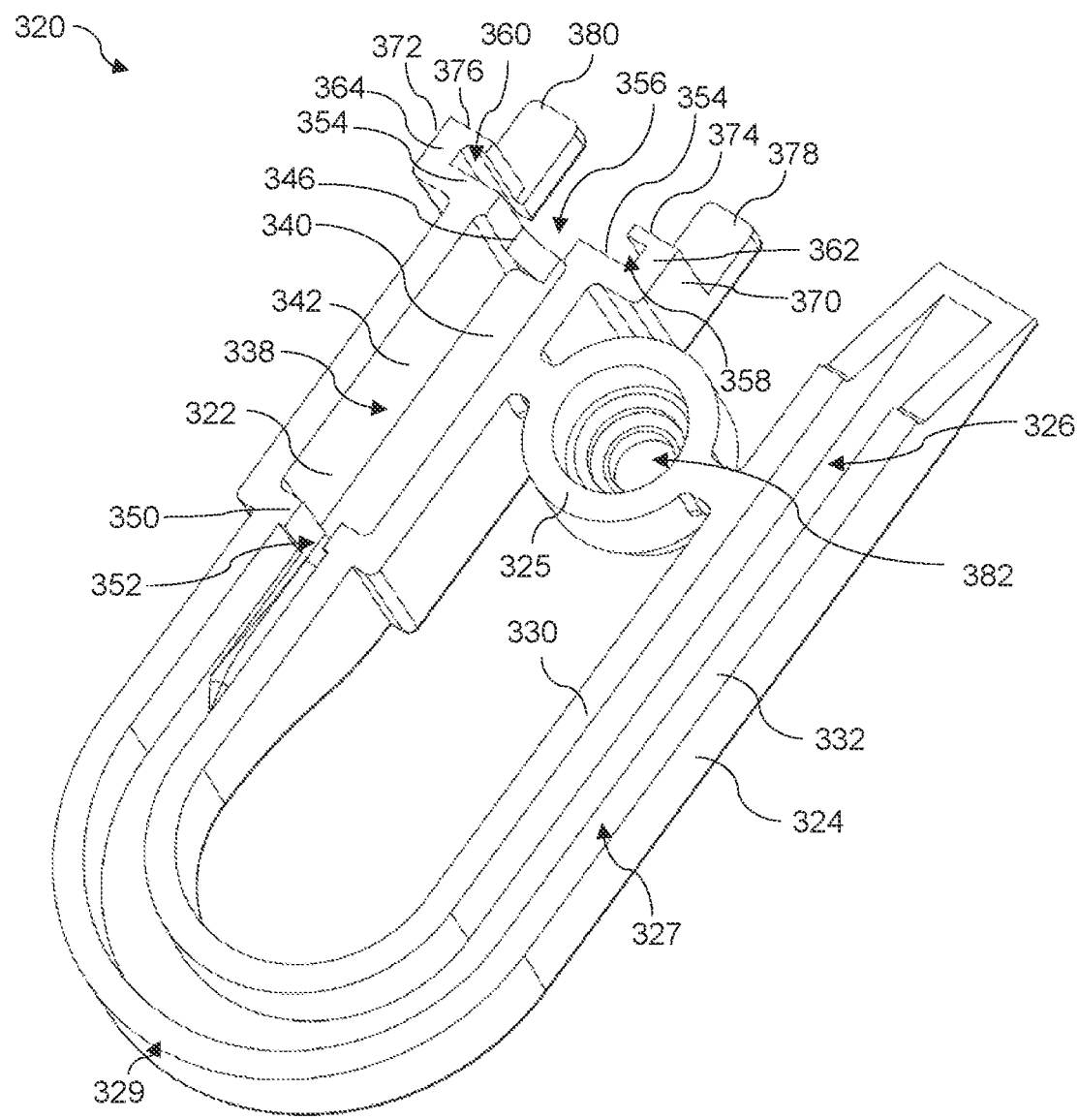
FIG. 21 is a rear perspective view of the bracket of FIG. 20.

With continued reference to FIGS. 13-15, the optical fiber cable 310 is routed through the distal wall of the interface retention portion, is curved, and is routed through the cable retention portion 324 of the bracket 320. The curvature of the optical fiber cable 310 has a radius of curvature (bend radius) that allows for the optical signal to propagate in the optical fiber without or with an acceptable minimum loss of the signal. In some embodiments, the radius of curvature is 1 cm to 4 cm. A suitable optical fiber cable 310 may be, for example, a multimode (MM) 50 micron OM4 bend insensitive fiber. In some embodiments, the optical fiber cable 310 may be a single mode (SM) fiber, or a multimode (MM) fiber of 62.5 micron diameter. In still other embodiments, it is contemplated that the optical fiber cable 310 may comprise an OM5 or OM6 designated fiber.

The cable retention portion 324 and the interface retention portion 322 are separated from one another by a predetermined distance so as to set a radius of curvature of the optical fiber cable 310 that allows for transmission of the optical video signal. In some embodiments, the distance between the channel 326 of the cable retention portion 324 and the channel 338 of the interface retention portion 322 is 2 cm to 8 cm. In some embodiments, the optical fiber cable 310 is fixed in the channel 326 of the cable retention portion 324. The diameter of the optical fiber cable 310 relative to the channel 326 may be such that the optical fiber cable 310 is prevented from freely moving through the channel 326 due to frictional forces between the optical fiber cable 310 and the channel 326. In other embodiments, the optical fiber cable 310 is freely movable within the channel 326.

The optical fiber cable 310 is routed through the cable retention portion 324 of the bracket 320 and to the light head housing 116, 122. The optical fiber cable 310 may be routed in any suitable manner between the bracket 320 and the light head housing 116, 122, so long as an acceptable bend radius of the optical fiber cable 310 is maintained. In the exemplary embodiment shown the cable retention portion 324 of the bracket 320 retains the optical fiber cable 310 while also allowing slack in the optical fiber cable 310 between the cable retention portion 324 and the light head housing 116, 122. In some embodiments, the slack in the optical fiber cable 310 may allow for flexibility in the optical fiber cable 310 during rotation of the camera assembly 182 so that, for example, the optical fiber cable 310 merely bends and flexes as needed between the cable retention portion 324 and for example the accessory port connector 311 in the light head housing 116, 122, as shown in FIGS. 4-6, 14 and 15. The optical fiber cable 310 is curved with a suitable bend radius and routed through the spindle 206 and to the light head housing 116, 122. The optical fiber cable 310 and/or any additional or alternate cables may be routed in any suitable manner through the components of the medical device support system 100 to reach for example the display 202 or other components of the system 100.

Thus, the distal end 312 of the optical fiber cable 310 includes the ferrule 314 and the bracket 320 includes the interface channel 338 within which the ferrule 314 seats to align the distal end 312 of the optical fiber cable 310 with the optical video signal transmission port 304 of the fiber module 302. Further, the bracket 320 includes the biasing member 316 that exerts a continuous force against the ferrule 314 to compress the distal end 312 of the optical fiber cable 310 against the optical video signal transmission port 304 of the fiber module 302. The interface channel 338 has at its opposite ends the distal wall 350 and the fiber module 302 respectively, and, as shown in FIG. 13, the biasing member 316 has a first end that exerts the continuous force against the ferrule 314 and a second end that abuts the distal wall 350. The bracket 320 includes the guide channel 326 that guides the optical fiber cable 310 within the handle housing 176 and to the light head housing 116, 122. The optical fiber cable 310 has a bend radius as it passes between the distal wall 350 and the light head housing 116, 122.

With continued reference to FIG. 5, and with additional reference to FIGS. 16-19, the camera assembly 182 may include a heat transfer plate 400. In the example shown, the bracket 320 may be fixed to the camera assembly 182 such that the bracket 320 and the fiber module 302 are in contact with the heat transfer plate 400. The heat transfer plate 400 may be made from metal or any other suitable heat transfer material. The heat transfer plate 400 is in heat transmissive contact with the fiber module 302 to draw heat away from the fiber module 302.

FIGS. 16-19 show that the heat transfer plate 400 includes a main body 402 having major surfaces 404, 406 spaced apart from one another in a thickness direction T. The main body 402 is shown as having planar major surfaces 404, 406, although it will be appreciated that in other embodiments, the main body 402 (and the major surfaces thereof) may be curved in one or more directions. The perimeter of the main body 402 (viewed in a direction normal to the major surfaces, such as that shown in FIG. 18) may have any suitable shape. In the illustrated embodiment, the main body 402 has a perimeter including protrusions 408, 410, 412, 414 such that the profile of the major surfaces allow for the bracket 320 to at least partially correspond to the perimeter of the bracket 320, as well as the fiber module 302 when mounted to the bracket 320. This may allow for increased contact between the bracket 320 and the heat transfer plate 400, as well as the fiber module 302 and the heat transfer plate 400. The main body 402 of the heat transfer plate 400 includes one or more orifices 418, which may allow for the heat transfer plate 400 to be mounted (e.g., via a fastener such as a screw, rivet, etc.) to the camera assembly 182 and/or may allow for the bracket 320 to be mounted (e.g., via a fastener such as a screw, rivet, etc.) to the heat transfer plate 400.

In some embodiments, the heat transfer plate 400 may be coupled to a heat sink to provide further dissipation of heat from the fiber module 302. In the embodiment shown, the heat transfer plate 400 includes a tab 416 that is arranged orthogonal to the main body 402 of the heat transfer plate 400. The tab 416 includes an orifice 418 through which the tab 416 may be secured (e.g., via a fastener such as a screw, rivet, etc.) to a separate heat sink in the camera assembly 182.

FIGS. 20-23 show another exemplary embodiment of the bracket 320. In this embodiment, the interface retention portion 322 and the fastening portion 325 are similar to that described above with respect to the bracket 320 shown in FIGS. 9-15, and the features thereof will not be repeated for the sake of brevity. However, the cable retention portion 324 includes a channel 326 that is in contact with the distal wall 348 of the interface retention portion 322. As shown, the channel 326 includes a bottom wall 328 and side walls 330, 332, and the channel 326 includes a linear portion 327 and a curved portion 329. The curved portion of the channel has a predetermined radius of curvature (bend radius) and serves a guide for setting and maintaining the radius of curvature of the optical fiber cable 310. It will be appreciated that the bracket shown in FIGS. 20-23 may be implemented in any of the embodiments of the handle shown and described in the present disclosure.

FIGS. 24-33 show an exemplary medical device support system 500 according to another embodiment of the invention. The medical device support system 500 is in many respects similar to the afore described medical device support system 100, and consequently the same reference numerals are used to denote structures corresponding to similar structures in the medical device support system 100. In addition, the foregoing description of the medical device support system 100 is equally applicable to the medical device support system 500 in addition to or except as noted below. Moreover, it will be appreciated upon reading and understanding the specification that aspects of the medical device support systems 100, 500 may be substituted for one another or used in conjunction with one another where applicable.

Turning then to FIGS. 24-28, the medical device support system 500 includes the light head 110, the display 202, and a camera arm 504 having a camera 506 mounted at its distal end. The light head 110 is coupled to the corresponding extension arm 104 by an articulating assembly 520 which in the illustrative embodiment includes the yoke assembly 108 and corresponding load balancing arm 106. The corresponding extension arm 104 includes a hub 522 at a proximal end thereof mounted to the central shaft 102 to enable pivotable movement of the extension arm 104 about the central shaft 102. The articulating assembly 520 is coupled to a distal end of the extension arm 104, as shown. Similarly, the display 202 is coupled to the corresponding extension arm 104 by an articulating assembly 530 which in the illustrative embodiment includes the corresponding load balancing arm 106. The corresponding extension arm 104 includes a hub 532 at a proximal end thereof mounted to the central shaft 102 to enable pivotable movement of the extension arm 104 about the central shaft 102. The articulating assembly 530 is coupled to a distal end of the extension arm 104, as shown. The camera arm 504 is connected to a distal end of the corresponding extension arm 104. The corresponding extension arm 104 includes a hub 542 at a proximal end thereof mounted to an auxiliary shaft 544 of the medical device support system 500 to enable pivotable movement of the corresponding extension arm 104 about the auxiliary shaft 544.

Figure 26:
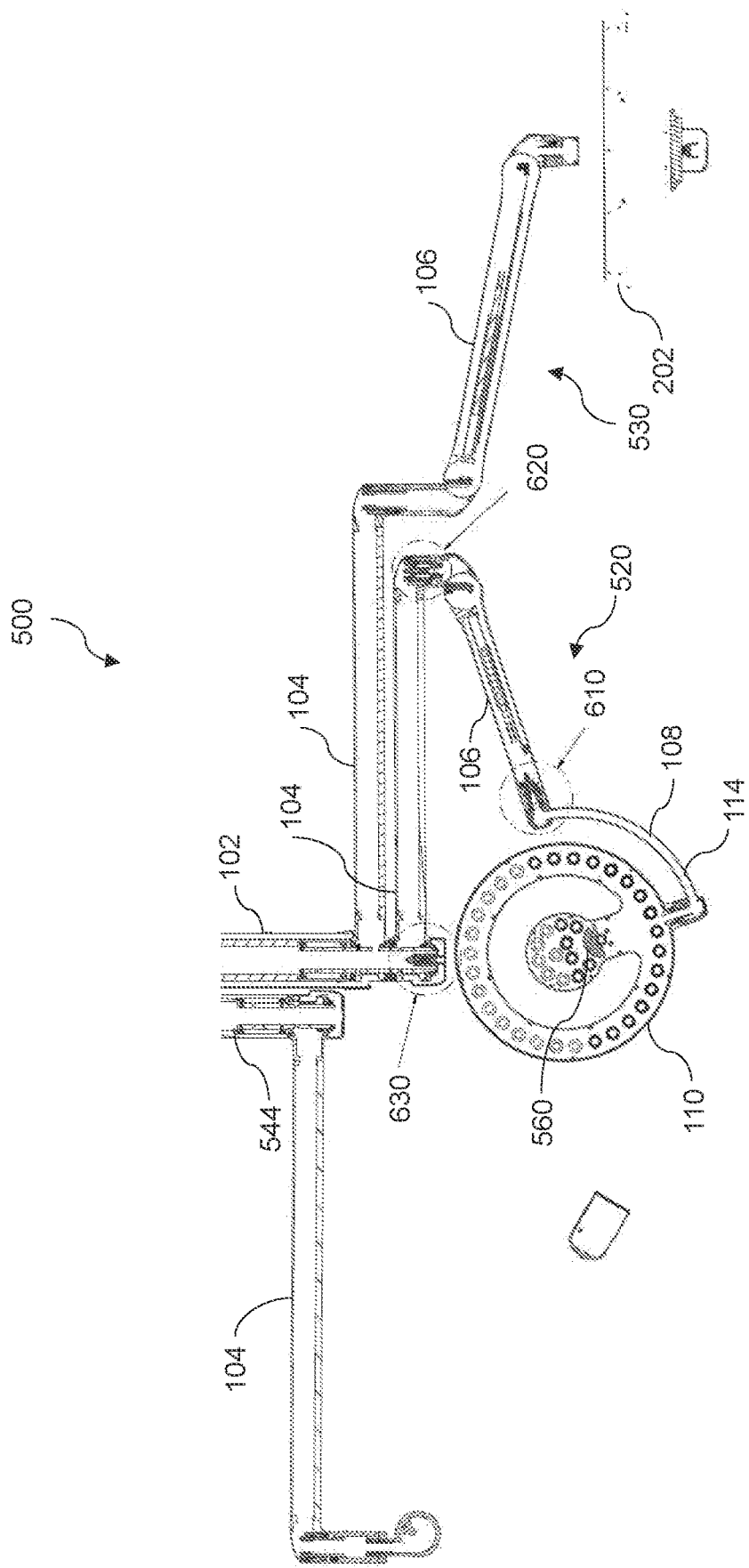
FIG. 26 is a cutaway view of the FIG. 24 medical device support system, shown with rotatable joints.
Figure 27:
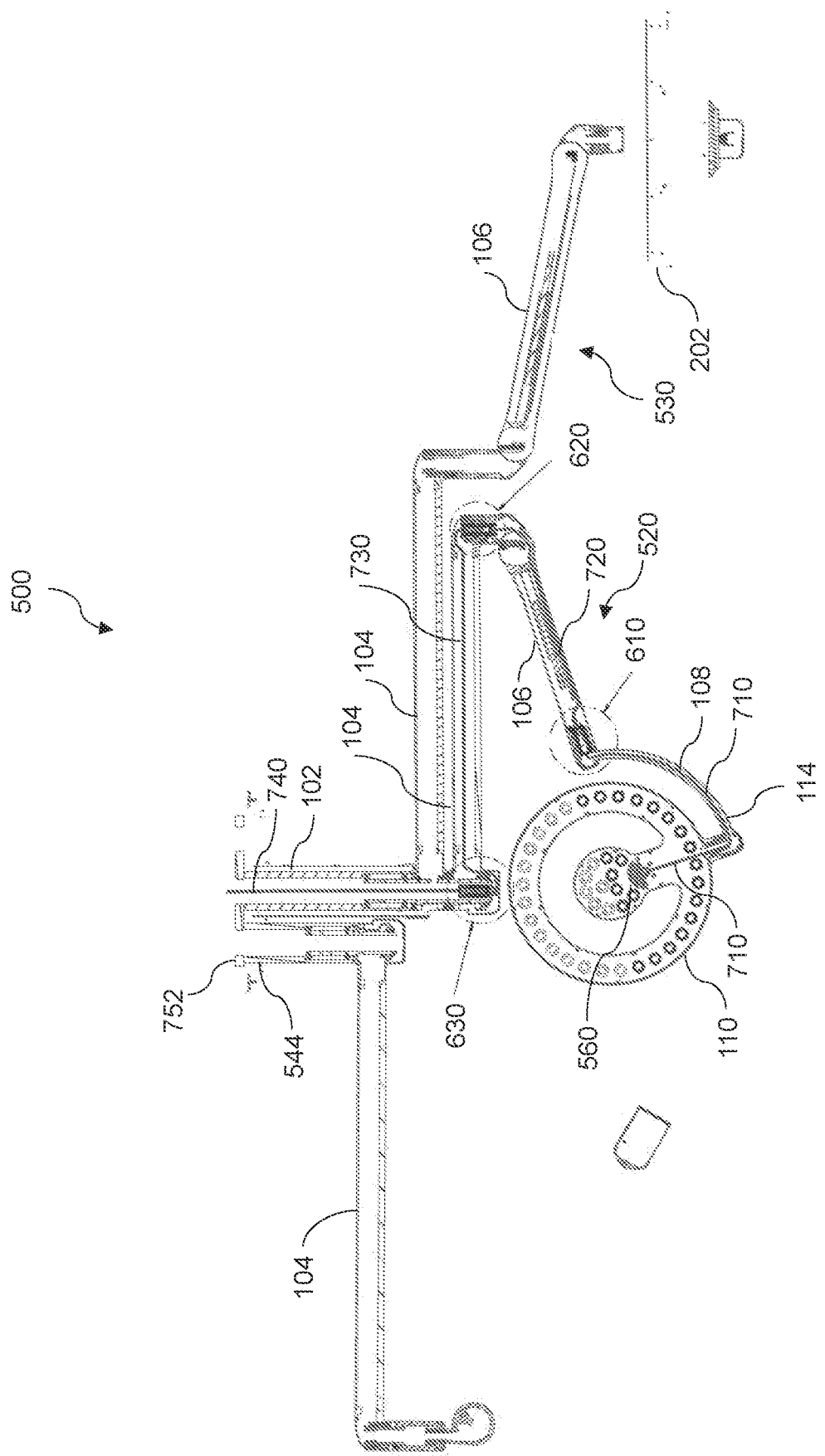
FIG. 27 is a cutaway view of the FIG. 24 medical device support system, shown with rotatable joints and optical fiber cables.
Figure 28:
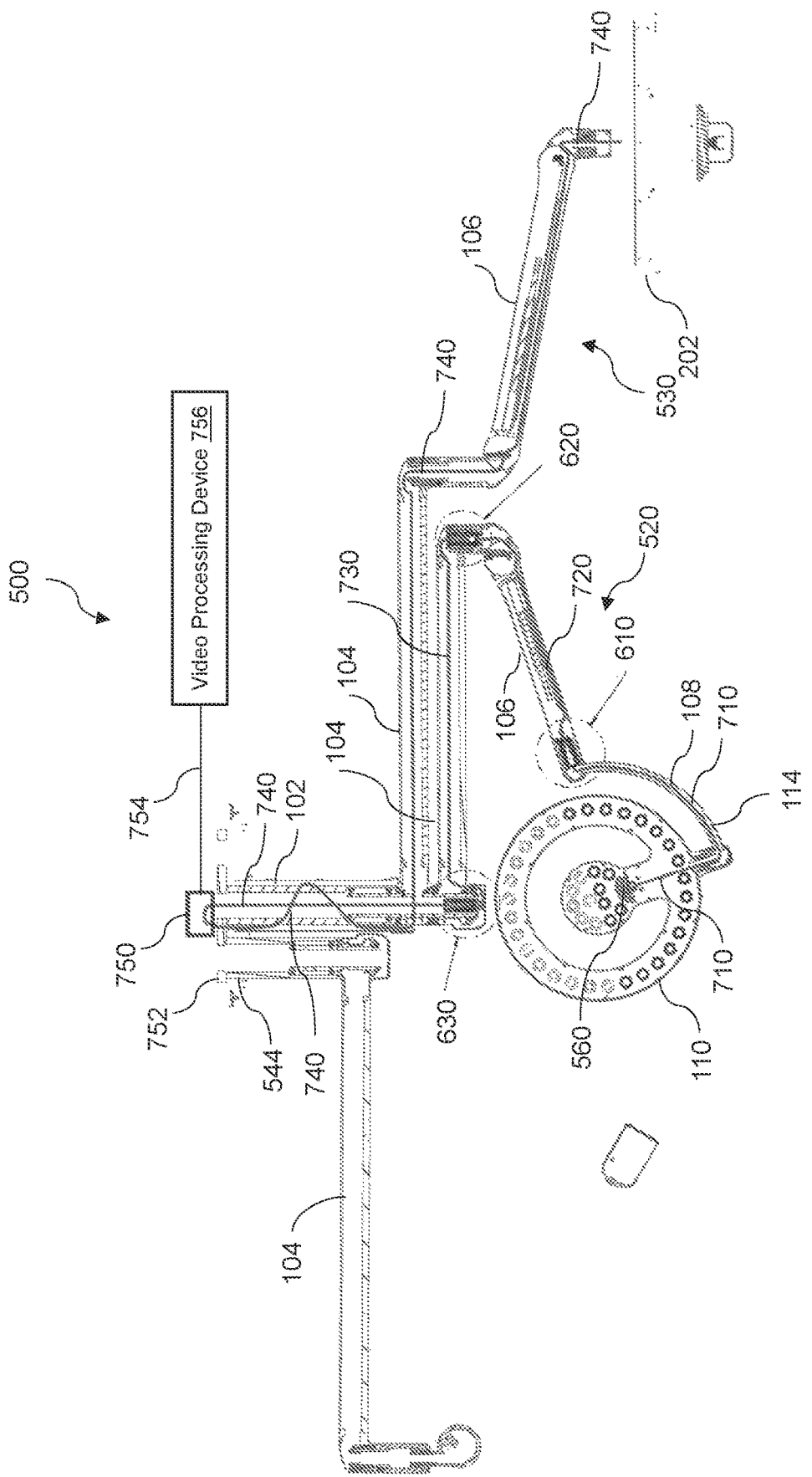
FIG. 28 is a cutaway view of a variant of the FIG. 24 medical device support system, showing rotatable joints and optical fiber cables.

FIGS. 26-28 show greater detail of a means for propagating an optical signal originating from the light head 110 to the central shaft 102 and/or from the central shaft 102 to the display 202. The light head 110 may include an optical signal generating component 560 such as the afore described camera 184 of the camera assembly 182 or any other suitable optical signal generating component. The optical signal generating component 560 may be configured to capture data associated with for example the afore described region of interest 188 (see FIG. 7) or any other suitable region of interest. The optical signal generating component 560 may be configured to generate an optical signal based on the captured data. In some embodiments, the camera 184 may have a field of view that encompasses at least a portion of the region of interest 188, and the optical signal may include optical video signals associated with video data captured by the camera 184. The optical signal may include a unidirectional optical video signal. In some embodiments, the optical signal may include a bidirectional control signal.

The light head 110 may take on any suitable configuration for originating the optical single therein. With reference again to FIGS. 2-6, for example, the light head 110 may include a light head housing 116, 122 and a handle 164 mounted to the light head housing 116, 122 and protruding downward from the light head housing 116, 122, where the optical signal generating component 560 includes for example camera 184 mounted within the handle 164. In this regard, the optical signal generating component 560 may be rotatable within the handle 164 in a manner similar to that described above for the camera 184. Other embodiments are also contemplated. For example, with reference to FIGS. 1 and 2, the optical signal generating component 560 may be located in the light head 110 in a location other than the handle 164, for example in the annular shape outer portion 128, the inner round portion 130, and/or the radially protruding arm 132 of the light head 110.

With reference again to FIGS. 4-6, 14 and 15, where the optical signal generating component 560 is mounted within the handle 164, the handle 164 may include a first mating connector such as the afore described accessory port connector 311, and the light head housing 116, 122 may include a hub such as the afore described hub 166 that has a second mating connector. In this way, the handle 164 may be selectively attachable to and detachable from the hub 166 wherein, in the attached state, the mated first and second mating connectors connect to transmit the optical signal from one optical fiber cable inside the handle 164, for example optical fiber cable 310 in FIGS. 4-6 and 13-15 in handle 164, to another optical fiber cable inside the light head housing 116, 122, for example optical fiber cable 710 to be described in greater detail below. In some embodiments, the handle 164 may not be attachable to and detachable from the light head 110, and the optical fiber cable 310 inside the handle 164 may pass directly from the handle 164 to the interior of the light head housing 116, 122 without passing through an accessory port connector.

Reference is now made to FIGS. 26 and 27, which shows multiple rotatable joints 610, 620, 630 and multiple optical fiber cables 710, 720, 730, 740 configured to transmit the optical signal from the light head 110 to, for example, the yoke assembly 108, the load balancing arm 106, the extension arm 104, and the central shaft 102. For ease of illustration, FIG. 26 is a cutaway view of the FIG. 24 medical device support system 500 shown only with the rotatable joints 610, 620, 630, whereas FIG. 27 is a cutaway view of the FIG. 24 medical device support system 500 shown with both the rotatable joints 610, 620, 630 and the optical fiber cables 710, 720, 730, 740. Thus, starting from the light head 110, for example, the rotatable joints 610, 620, 630 and the optical fiber cables 710, 720, 730, 740 may be configured to transmit the optical signal associated with the captured data from the light head 110 through the yoke assembly 108, through the load balancing arm 106, through the extension arm 104, and to the central shaft 102.

The yoke assembly 108 may be pivotably rotatable about the distal end of the corresponding load balancing arm 106 via a first rotatable joint 610. The first rotatable joint 610 may be configured to transmit the optical signal from a first optical fiber cable 710 in the yoke assembly 108 to a second optical fiber cable 720 in the corresponding load balancing arm 106. As will be described in greater detail below, the first rotatable joint 610 may include any suitable configuration; in the illustrative embodiment, the first rotatable joint 610 is in the form of a continuously rotatable joint. The corresponding load balancing arm 106 may, in turn, be pivotably rotatable about the distal end of the corresponding extension arm 104 via a second rotatable joint 620. The second rotatable joint may be configured to transmit the optical signal from the second optical fiber cable 720 in the load balancing arm 106 to a third optical fiber cable 730 in the corresponding extension arm 104. The second rotatable joint 620 may also include any suitable configuration; in the illustrative embodiment, the second rotatable joint 620 includes a continuously rotatable joint.

The extension arm 104, as earlier described, has a hub 522 at a proximal end thereof mounted to the central shaft 102 for pivotable movement about the central shaft 102. The extension arm 104 may be pivotably rotatable about the central shaft 102 via a third rotatable joint 630, which may include for example the hub 522. The third rotatable joint 630 may be configured to transmit the optical signal from the third optical fiber cable 730 in the extension arm 104 to a fourth optical fiber cable 740 in the central shaft 102. As with the first and second rotatable joints 610, 620, the third rotatable joint 630 may also include any suitable configuration. In the illustrative embodiment, the third rotatable joint 630 includes a continuously rotatable joint.

Figure 24:
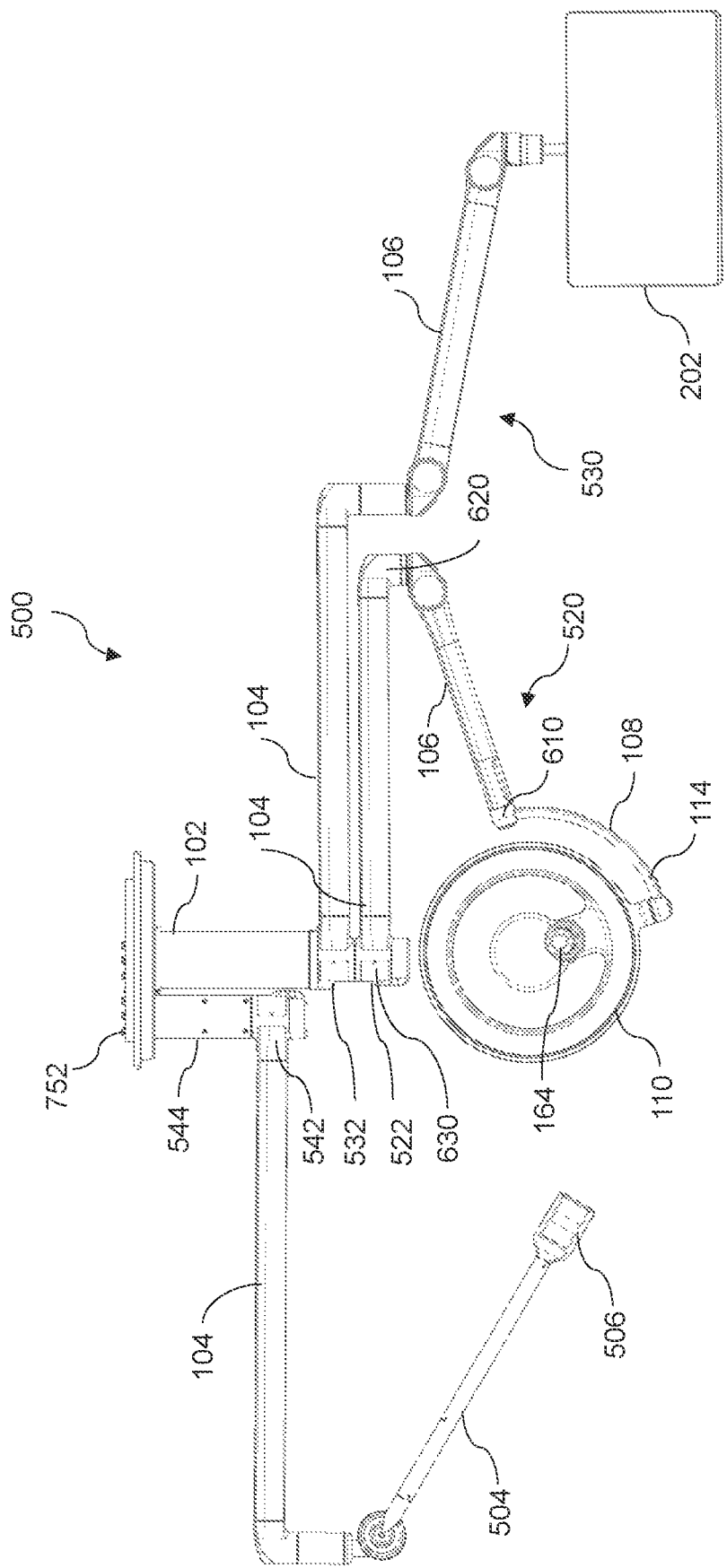
FIG. 24 is a side elevation view of an overall configuration of a medical device support system in accordance with another embodiment of the present disclosure, showing a left positioned camera arm and camera, a center positioned surgical light head, and right positioned display.
Figure 25:
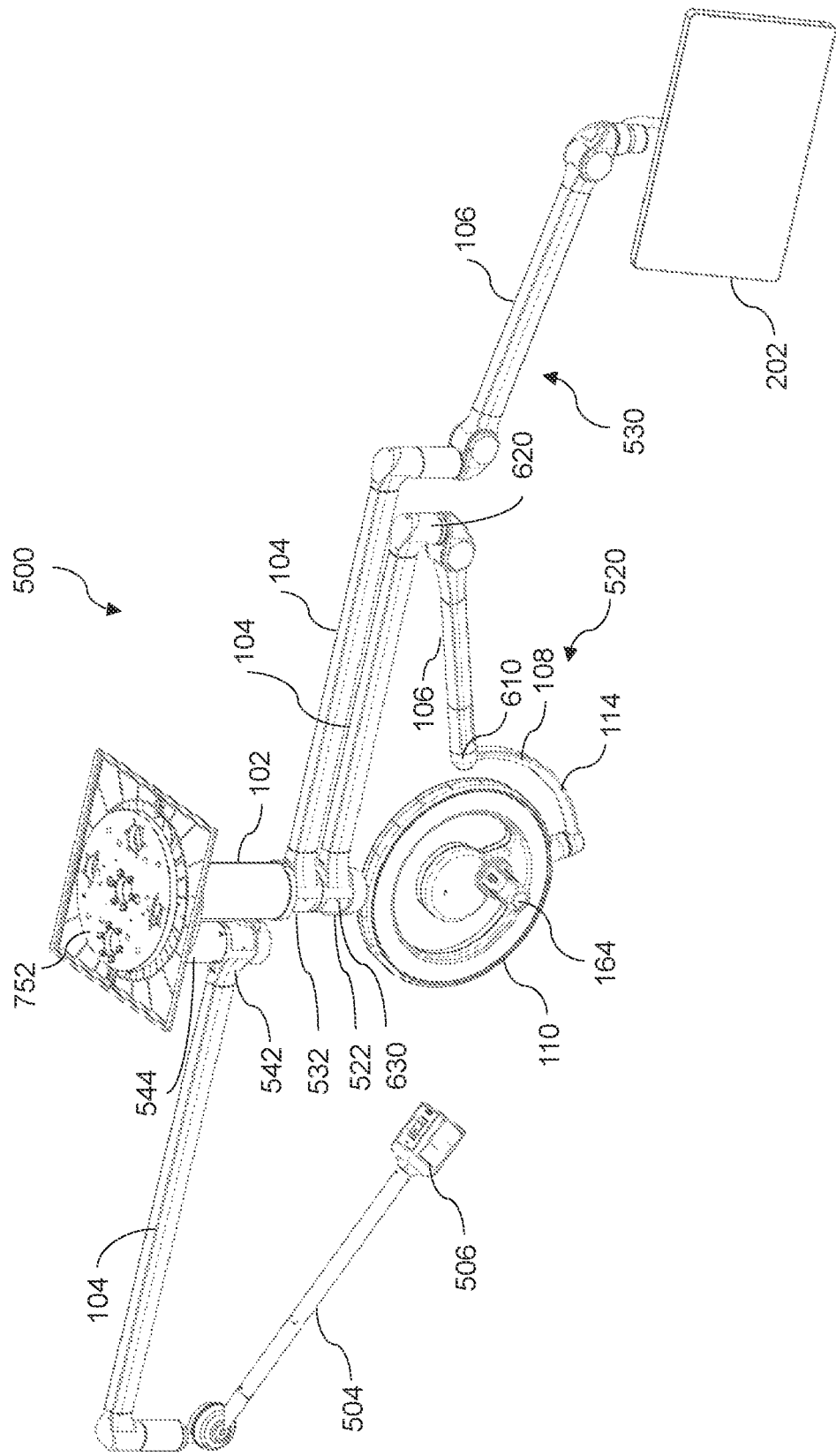
FIG. 25 is a top perspective view of the FIG. 24 medical device support system.

FIG. 28 is a cutaway view of a variant of the FIG. 24 medical device support system 500, showing rotatable joints 610, 620, 630 and optical fiber cables 710, 720, 730, 740. The FIG. 28 medical device support system 500 includes a video hub 750 for converting video signals. The optional video hub 750 may be used, for example, to clean up and amplify the optical video signal, or to convert the optical video signal to other video protocols or transmission media (e.g. copper) compatible with what it is interfacing to. The video hub 750 may be mounted to a ceiling plate 752 of the medical device support system 500, for example, above the central shaft 102. The video hub 750 also could be a remotely located integration system. The fourth optical fiber cable 740 can be routed to the video hub 750 where conversion of the video signal takes place prior to the signal being transmitted elsewhere in the medical device support system 500, or transmitted to a location separate from the medical device support system 500. For example, the optical signal may be transmitted by another optical fiber cable 754 to a location separate from the central shaft 102, the extension arms 104, and the articulating assemblies 520, 530, for example, to a video processing device 756 located in a room separate from the operating room within which the medical device support system 500 is located. Alternately, the optical fiber cable 740 may be routed directly to a fiber-ready monitor such as the display 202 via, for example, the central shaft 102, the corresponding extension arm 104, and the articulating assembly 530 mounted at the distal end of the extension arm 104. In some embodiments, the optical fiber cable 740 may comprise a continuous cable run from the rotatable joint 630 to the display 202 that transmits the optical signal from the central shaft 102 to the extension arm 104, the load balancing arm 106, and the display 202, without passing through or being processed by the video hub 750.

Figure 30:
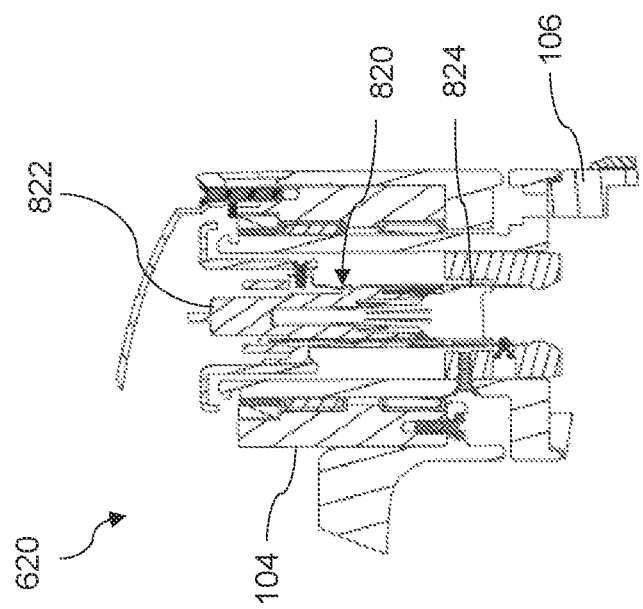
FIG. 30 is a cross section view of a second fiber optic rotary joint of the FIG. 24 medical device support system.
Figure 29:
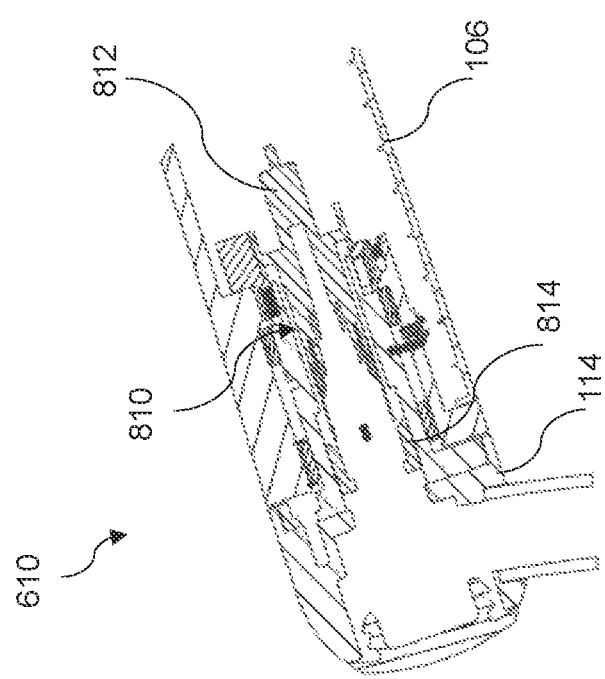
FIG. 29 is a cross section view of a first fiber optic rotary joint of the FIG. 24 medical device support system.
Figure 31:
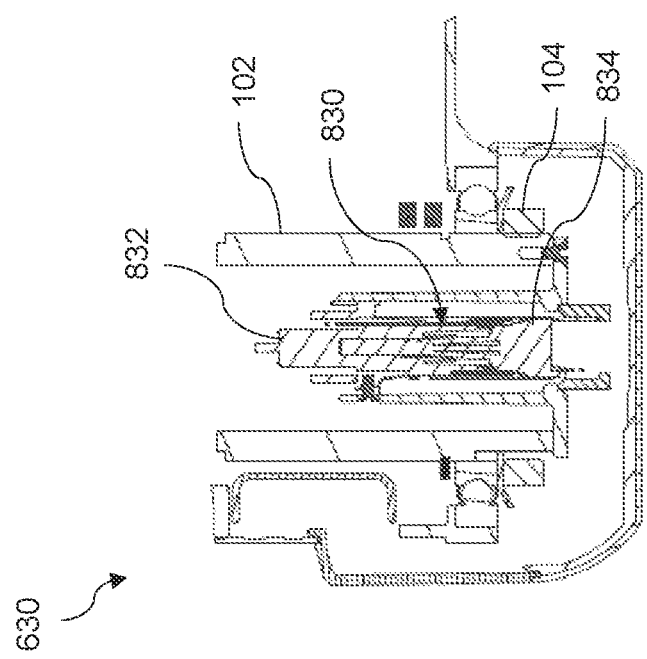
FIG. 31 is a cross section view of a third fiber optic rotary joint of the FIG. 24 medical device support system.

FIGS. 29-31 show the respective first, second, and third rotatable joints 610, 620, 630 in greater detail. The rotatable joints 610, 620, 630 may include any type of joint that enables transmission of the optical signal from one side of the joint to the opposite side of the joint. In some embodiments, the rotatable joint may also be configured to enable transmission of power and electrical signals from one side of the joint to the opposite side of the joint. For example, a slip ring, electrical rotary joint, swivel, rotary electrical interface, or other rotating electrical connector may be integrated into any one of the rotatable joints 610, 620, 630.

In the embodiments of FIGS. 29-31, each rotatable joint 610, 620, 630 includes a respective fiber optic rotary joint 810, 820, 830, also referred to as an FORJ. As shown in FIG. 29, the fiber optic rotary joint 810 includes a stationary component 812 that is fixed relative to the distal end of the load balancing arm 106 and a rotational component 814 that is fixed relative to a proximal end of the arm 114 of the yoke assembly 108. The fiber optic rotary joint 810 is configured to transmit the optical signal from the optical fiber cable 710 in the yoke assembly arm 114 to the optical fiber cable 720 in the load balancing arm 106, and vice versa where the optical signal is bidirectional, during rotation of the arm 114 relative to the distal end of the load balancing arm 106 via relative rotation between the rotational component 814 and the stationary component 812. In FIG. 30, the fiber optic rotary joint 820 includes a stationary component 822 that is fixed relative to the distal end of the extension arm 104 and a rotational component 824 that is fixed relative to the proximal end of the load balancing arm 106. The fiber optic rotary joint 820 is configured to transmit the optical signal from the optical fiber cable 720 in the load balancing arm 106 to the optical fiber cable 730 in the extension arm 104, and vice versa where the optical signal is bidirectional, during rotation of the load balancing arm 106 relative to the distal end of the extension arm 104 via relative rotation between the rotational component 824 and the stationary component 822. As shown in FIG. 31, the fiber optic rotary joint 830 includes a stationary component 832 that is fixed relative to the central shaft 102 and a rotational component 834 that is fixed relative to the proximal end of the extension arm 104. The fiber optic rotary joint 830 is configured to transmit the optical signal from the optical fiber cable 730 in the extension arm 104 to the optical fiber cable 740 in the central shaft 102, and vice versa where the optical signal is bidirectional, during rotation of the extension arm 104 about the central shaft 102 via relative rotation between the rotational component 834 and the stationary component 832.

Figure 32:
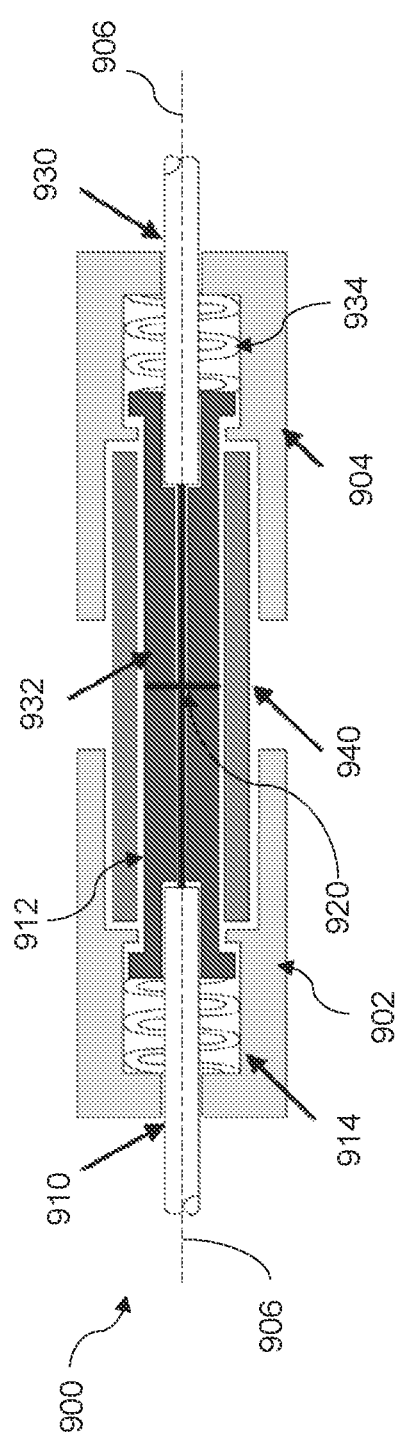
FIG. 32 is a cross section view showing a physical contact type fiber optic rotary joint.

The fiber optic rotary joints 810, 820, 830 of the rotatable joints 610, 620, 630 may have any suitable configuration to transmit the optical signal. FIG. 32, for example, shows a physical contact fiber optic rotary joint 900 and FIG. 33 shows an expanded beam fiber optic rotary joint 1000, either of which may be used as the fiber optic rotary joint 810, 820, 830 of the rotatable joints 610, 620, 630.

The physical contact fiber optic rotary joint 900 shown in FIG. 32 includes a stationary component 902 and a rotational component 904 that is rotatable relative to the stationary component 902 about a rotation axis 906. The stationary component 902 houses an optical fiber cable 910. An end of the optical fiber cable 910 is captured in a ferrule 912. The ferrule 912, in turn, is biased via an axial spring 914 toward a physical contact location 920. Similarly, the rotational component 904 houses an opposing optical fiber cable 930. An end of the optical fiber cable 930 is captured in a ferrule 932. The ferrule 932, in turn, is biased via an axial spring 934 toward the physical contact location 920. At the physical contact location 920, the ends of the respective optical fiber cables 910, 930 are maintained in physical contact by the biasing forces of the axial springs 914, 934. An alignment sleeve 940 may be provided to maintain alignment of the ferrules 912, 932, and thus the alignment of the ends of the optical fiber cables 910, 930, relative to one another. The physical contact between the ends of the respective optical fiber cables 910, 930 maintains transmission of the optical signal during rotation of the rotational component 904 relative to the stationary component 902. Any of the afore described stationary components 812, 822, 832 may take the form of the stationary component 902, and any of the afore described rotational components 814, 824, 834 may take the form of the rotational component 904.

Figure 33:
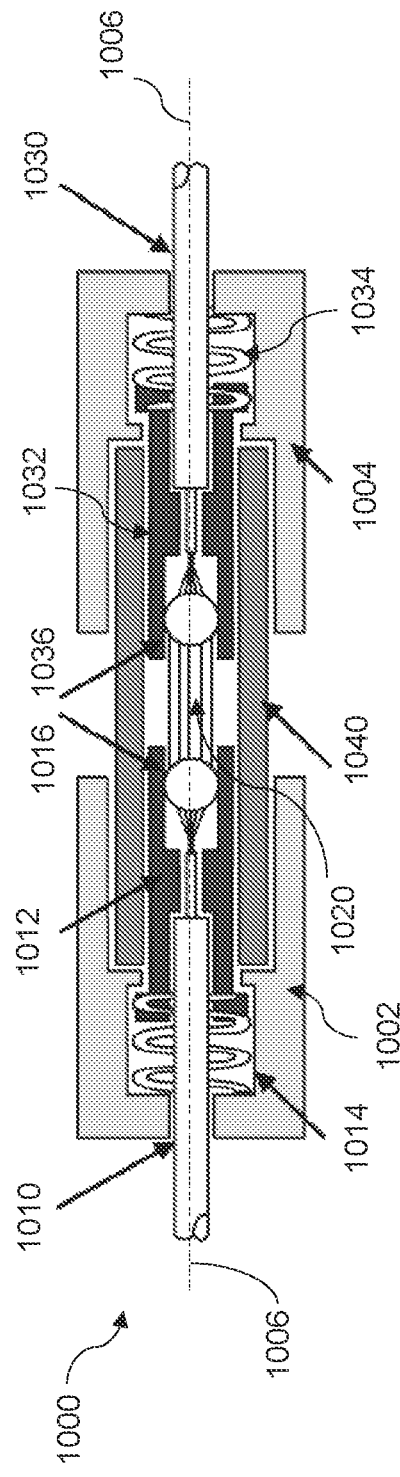
FIG. 33 is a cross section view showing an expanded beam type fiber optic rotary joint.
Figure 34:
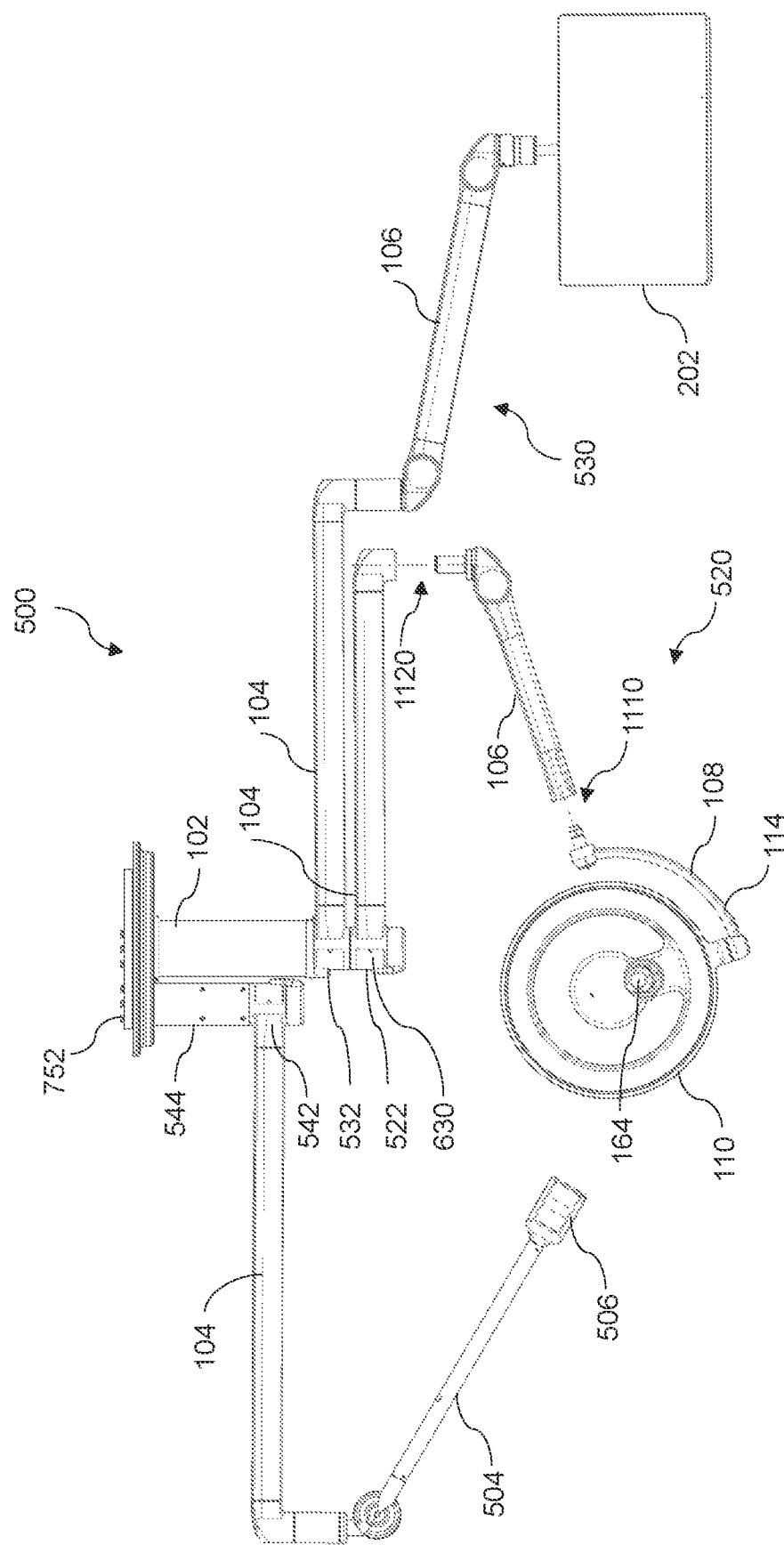
FIG. 34 is a side elevation view of an overall configuration of a medical device support system in accordance with another embodiment of the present disclosure, similar to the FIG. 24 system except showing detachable rotatable joints.
Figure 35:
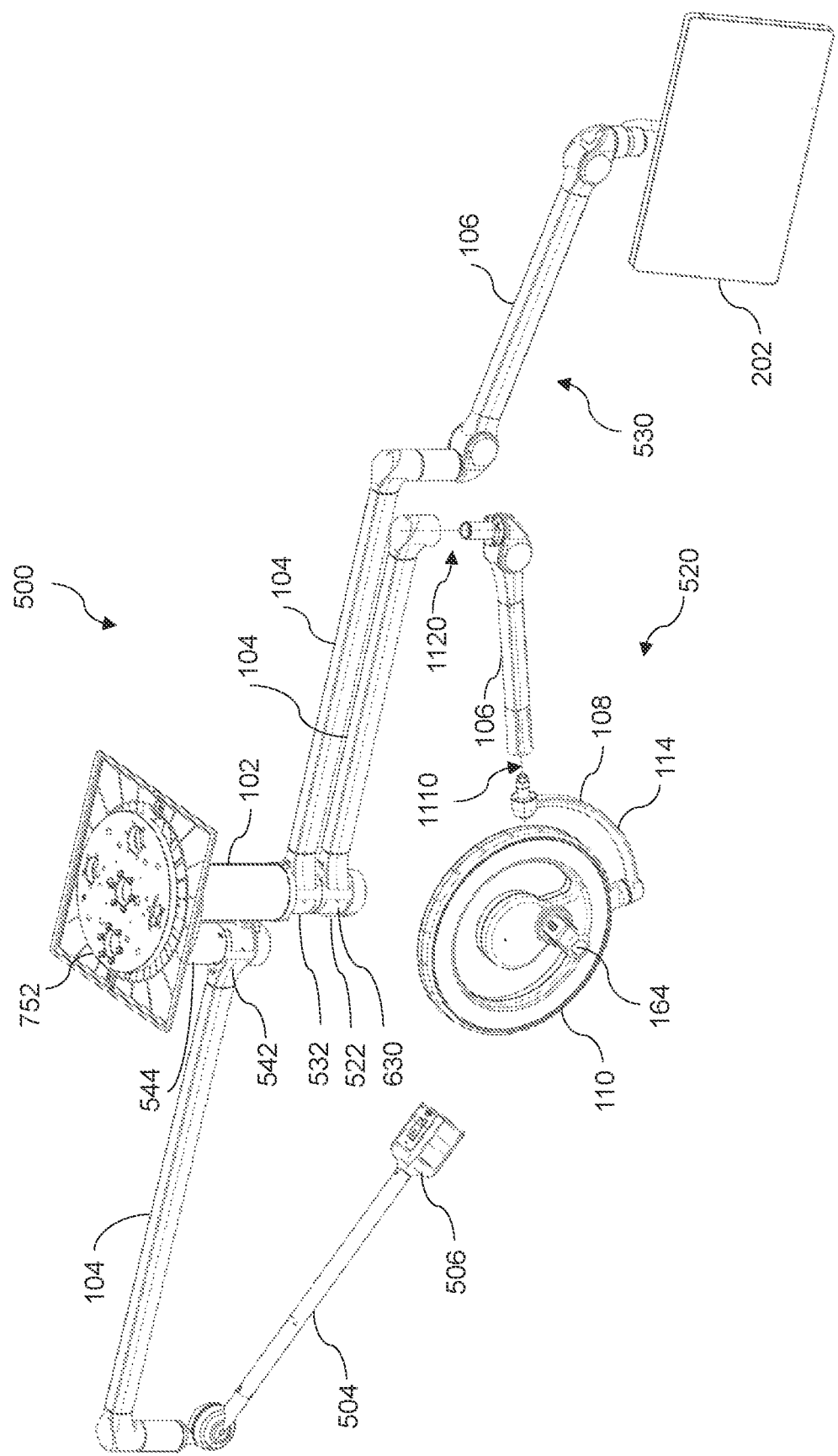
FIG. 35 is a top perspective view of the FIG. 34 medical device support system.

The expanded beam fiber optic rotary joint 1000 shown in FIG. 33 includes a stationary component 1002 and a rotational component 1004 that is rotatable relative to the stationary component 1002 about a rotation axis 1006. The stationary component 1002 houses an optical fiber cable 1010. An end of the optical fiber cable 1010 is captured in a ferrule 1012. The ferrule 1012, in turn, is biased via an axial spring 1014 toward an optical transfer/receive location 1020. A lens 1016 is captured in an opposite end of the ferrule 1012, the lens 1016 being configured to expand and collimate the light from the optical fiber cable 1010 to the optical transfer/receive location 1020. The lens 1016 may be for example a ball type lens, as shown, or a rod type lens. Similarly, the rotational component 1004 houses an opposing optical fiber cable 1030. An end of the optical fiber cable 1030 is captured in a ferrule 1032. The ferrule 1032, in turn, is biased via an axial spring 1034 toward the optical transfer/receive location 1020. A lens 1036 is captured in an opposite end of the ferrule 1032, the lens 1036 being configured to receive the collimated light from the optical transfer/receive location 1020 and refocus the light to the optical fiber cable 1030. The lens 1036 may be for example a ball type lens, as shown, or a rod type lens. At the optical transfer/receive location 1020, communication is maintained between the ends of the respective optical fiber cables 1010, 1030 by optical transmission from one lens 1016 to the other lens 1036. An alignment sleeve 1040 may be provided to maintain alignment of the ferrules 1012, 1032, and thus the alignment of the ends of the optical fiber cables 1010, 1030, relative to one another. The two lenses 1016, 1036 maintain optical transfer of the optical signal between the ends of the respective optical fiber cables 1010, 1030 during rotation of the rotational component 1004 relative to the stationary component 1002. Any of the afore described stationary components 812, 822, 832 may take the form of the stationary component 1002, and any of the afore described rotational components 814, 824, 834 may take the form of the rotational component 1004.

FIGS. 34-37 show a medical device support system 1100 in accordance with another embodiment of the present disclosure, similar to the FIG. 24 system except that two of the rotatable joints are configured as detachable rotatable joints 1110, 1120. The medical device support system 1100 is in many respects similar to the afore described medical device support systems 100, 500 and consequently the same reference numerals are used to denote structures corresponding to similar structures in the medical device support systems 100, 500. In addition, the foregoing description of the medical device support systems 100, 500 is equally applicable to the medical device support system 1100 in addition to or except as noted below. Moreover, it will be appreciated upon reading and understanding the specification that aspects of the medical device support systems 100, 500, 1100 may be substituted for one another or used in conjunction with one another where applicable.

Figure 36:
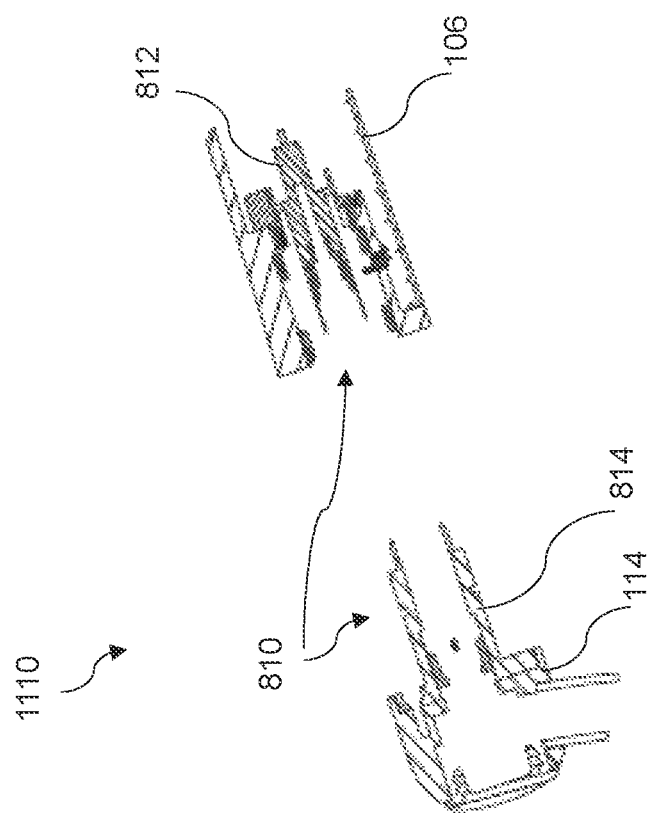
FIG. 36 is a cross section view of a first fiber optic rotary joint of the FIG. 34 medical device support system, shown in a detached state.
Figure 45:
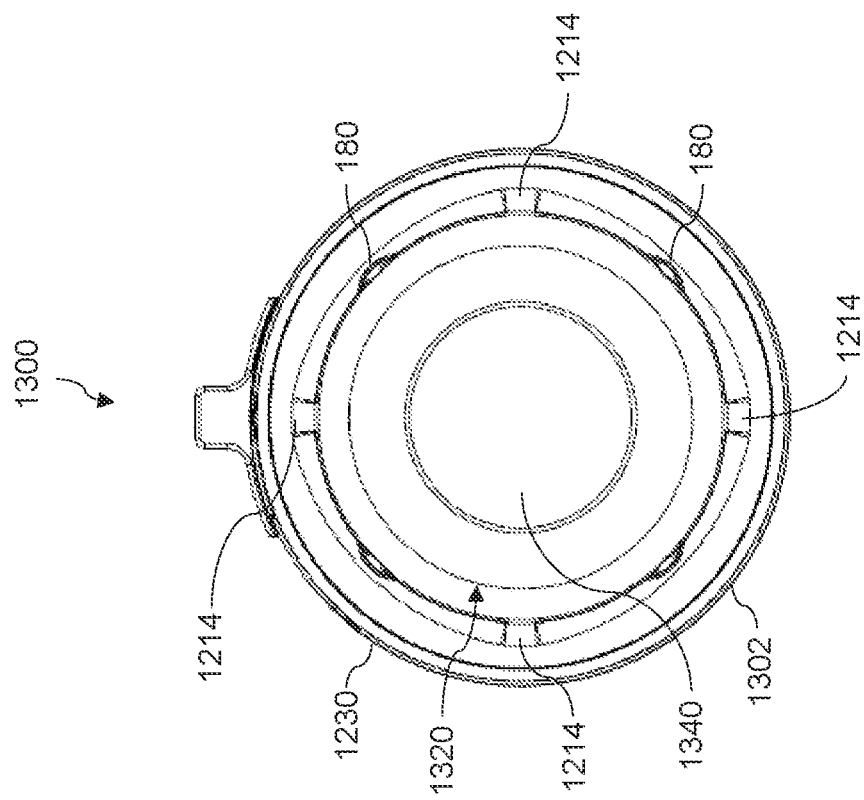
FIG. 45 is a bottom plan view of the FIG. 38 handle.
Figure 44:
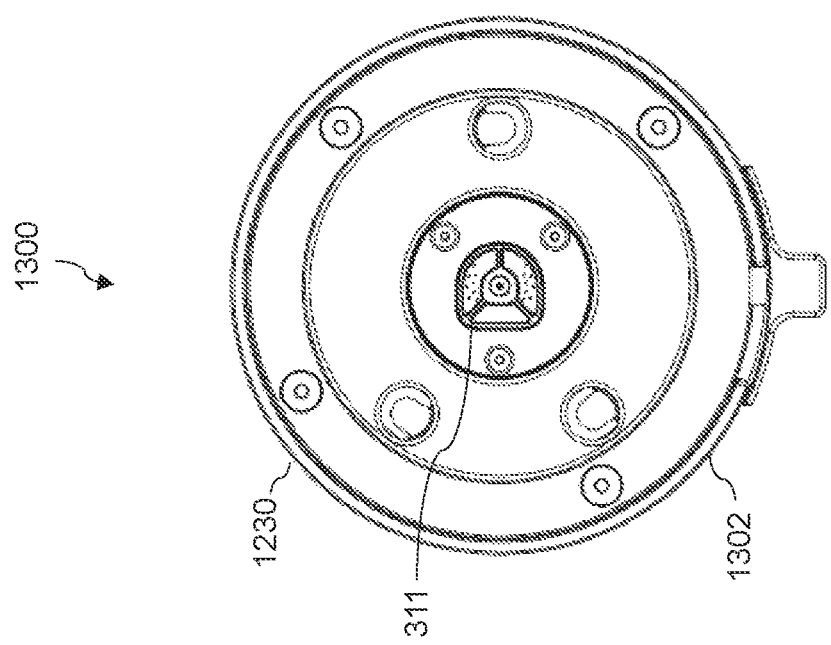
FIG. 44 is a top plan view of the FIG. 38 handle.
Figure 47:
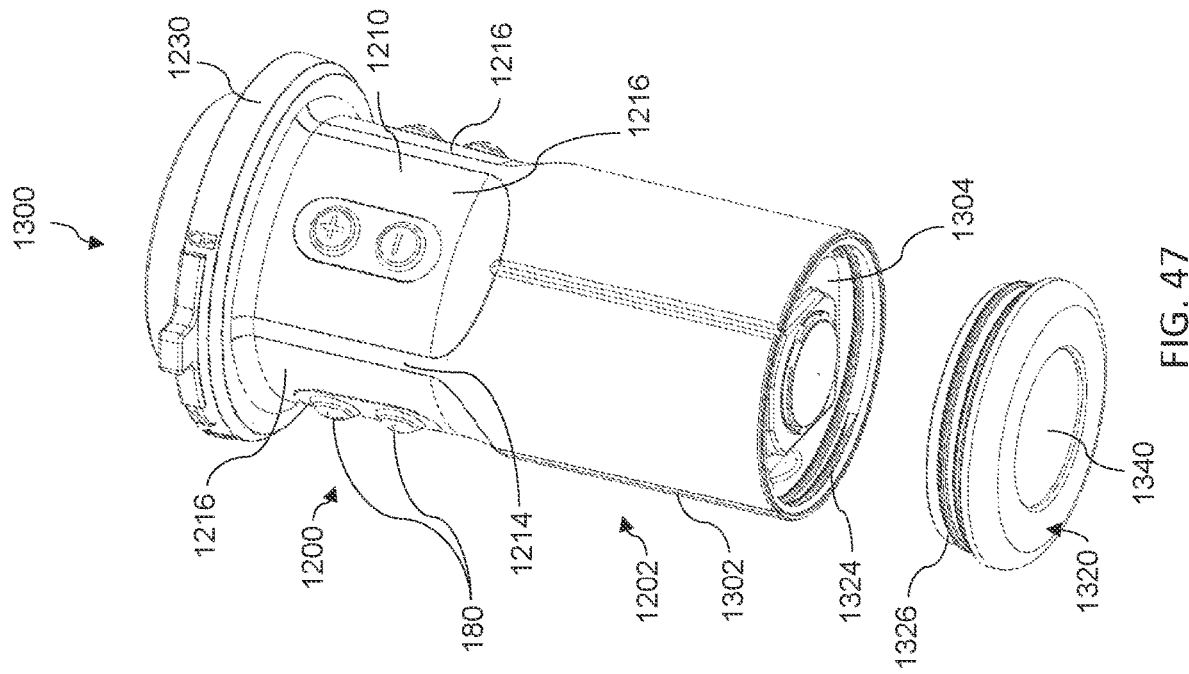
FIG. 47 is similar to FIG. 46 except exploded to show a cap of the handle removed.
Figure 46:
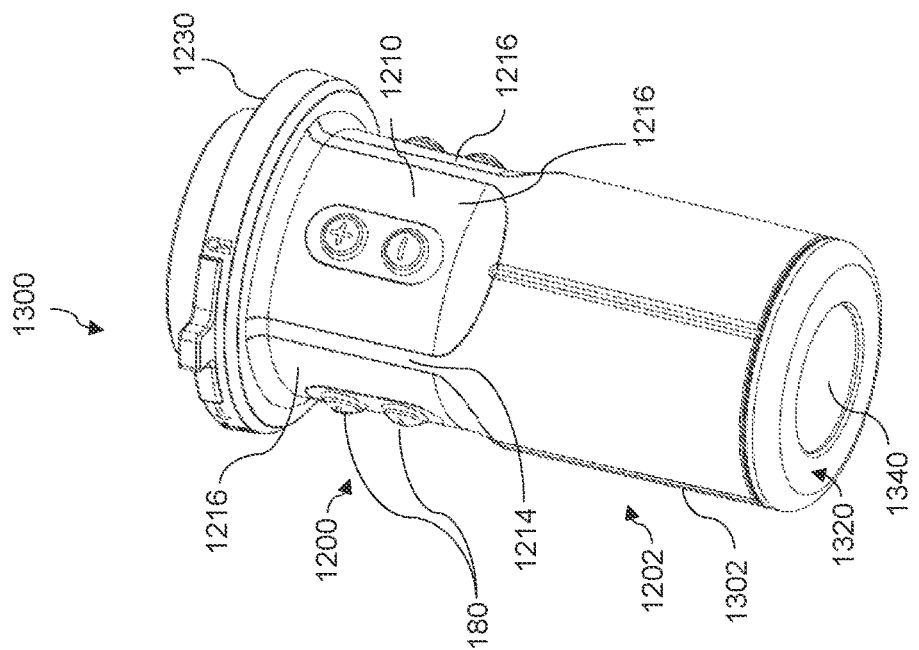
FIG. 46 is a bottom perspective view of the FIG. 38 handle.

As shown in FIG. 36, the rotatable joint 1110 is configured so that the rotational component 814 in the arm 114 of the yoke assembly 108 is selectively attachable to and detachable from the stationary component 812 in the distal end of the load balancing arm 106. As part of this configuration, the rotational component 814 of the fiber optic rotary joint 810 is configured as a first mating connector and the stationary component 812 of the fiber optic rotary joint 810 is configured as a second mating connector such that, when the arm 114 is attached to the distal end of the load balancing arm 106, the mated first and second mating connectors connect to transmit the optical signal from the first fiber optic cable 710 in the yoke assembly 108 to the second fiber optic cable 720 in the load balancing arm 106. The first and second mating connectors may be any suitable type of mating connector including, for example, a plug and socket type connector, a plug and jack type connector, among others. The mating rotatable joint 1110 with mating connector type fiber optic rotary joint 810 is advantageous in that different yoke assemblies 108 and light heads 110 may be attached to and removed from the distal end of the load balancing arm 106 such that when a different yoke assembly 108 is attached to the load balancing arm 106, the fiber optic rotary joint 810 maintains the contact optically between the first fiber optic cable 710 in the yoke assembly 108 and the second fiber optic cable 720 in the load balancing arm 106.

Figure 37:
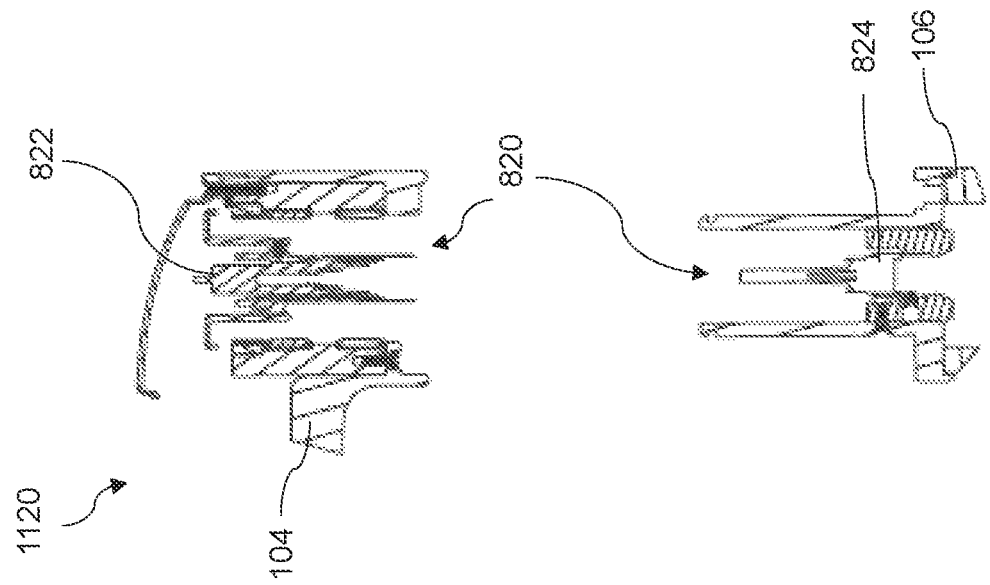
FIG. 37 is a cross section view of a second fiber optic rotary joint of the FIG. 34 medical device support system, shown in a detached state.

As shown in FIG. 37, the rotatable joint 1120 is configured so that the rotational component 824 in the proximal end of the load balancing arm 106 is selectively attachable to and detachable from the stationary component 822 in the distal end of the extension arm 104. As part of this configuration, the rotational component 824 of the fiber optic rotary joint 820 is configured as a first mating connector and the stationary component 822 of the fiber optic rotary joint 820 is configured as a second mating connector such that, when the load balancing arm 106 is attached to the distal end of the extension arm 104, the mated first and second mating connectors connect to transmit the optical signal from the second fiber optic cable 720 in the load balancing arm 106 to the third fiber optic cable 730 in the extension arm 104. The first and second mating connectors may be any suitable type of mating connector including, for example, a plug and socket type connector, a plug and jack type connector, among others. The mating rotatable joint 1120 with mating connector type fiber optic rotary joint 820 is advantageous in that different load balancing arms 106 may be attached to and removed from the distal end of the extension arm 104 such that when a different load balancing arm 106 is attached to the distal end of the extension arm 104, the fiber optic rotary joint 820 maintains the contact optically between the second fiber optic cable 720 in the load balancing arm 106 and the third fiber optic cable 730 in the extension arm 104.

Referring again to FIGS. 3 and 4, the handle 164 of the light head 110 will now be described in greater detail. The handle 164 includes a handle housing 176 that has an upper generally tubular section 1200 mounted to the light head housing 116, 122 and a lower generally tubular section 1202 extending downward from a bottom of the upper generally tubular section 1200. As shown in FIGS. 3 and 4, the outer perimeter of the lower generally tubular section 1202 is relatively wider in axial cross section than the outer perimeter of the upper generally tubular section 1200 over a portion, for example a plurality of recesses 1210, of the upper generally tubular section 1200. With particular reference to FIG. 4, the width at the axial cross section is perpendicularly across the center axis of the handle housing 176, which in the illustrative embodiment coincides with the afore described rotation axis R. As shown in FIG. 4, the width in axial cross section of the lower generally tubular section 1202 is greater than the width in axial cross section of the upper generally tubular section 1200 over the portion where the plurality of recesses 1210 are provided in the upper generally tubular section 1200.

The lower generally tubular section 1202 may be cylindrical in shape, as shown, or non-cylindrical in shape. The upper generally tubular section 1200 may be generally square tubular in shape, as shown, or non-generally square tubular in shape. The generally square tubular shape of the upper generally tubular section 1200 includes the four curved recesses 1210 forming the four sides of the square shape and four relatively smaller size curved corners 1214 disposed between respective adjacent recesses 1210. In other words, the upper generally tubular section 1200 has recesses 1210 and curved corners 1214 disposed in alternate fashion around the outer perimeter of the upper generally tubular section 1200, that is, disposed about the center axis (rotation axis R) of the handle housing 176. As will be appreciated, the shape of the upper generally tubular section 1200 need not be limited to a generally square shape and the quantity of recesses 1210 need not be limited to four. Other embodiments are contemplated. The upper generally tubular section 1200 may have any polygonal shape in axial cross section, for example three, five, or six recesses 1210, in which case, the upper generally tubular section 1200 would have, respectively, a generally triangular tubular shape, a generally pentagonal tubular shape, or a generally hexagonal tubular shape.

The upper generally tubular section 1200 and lower generally tubular section 1202 may be made of a single monolithic structure, as shown, or a multi-piece construction. The single monolithic structure may be formed by a net shape manufacturing technique or near net shape manufacturing technique, and may include, for example, an injection molded structure or a 3D printed structure. The upper generally tubular section 1200 may include a flange 1230 that protrudes radially outwardly relative to the recesses 1210 and curved corners 1214. The flange 1230 may cover, for example, mounting structure of the handle 164 and/or mounting structure of the light head housing 116, 122 to which the handle 164 is mounted. In the illustrated embodiment, the width in axial cross section of the lower generally tubular section 1202 where the lower generally tubular section 1202 transitions to the upper generally tubular section 1200 is equal to the width in axial cross section of the upper generally tubular section 1200 at the curved corners 1214.

As shown in FIG. 3, each recess 1210 includes a surface 1216 recessed radially inwardly relative to the outer perimeter of the lower generally tubular section 1202 and recessed radially inwardly relative to the curved corners 1214 of the upper generally tubular section 1200. The surfaces 1216 may be curved, as shown, or planar (the secant of a circle defined at the radius of the curved corners 1214), it being understood that a curved recess generally will provide more capacity inside the handle housing 176 than a planar recess.

The outer perimeter of the handle housing 176 tapers downwardly from the upper most portion of the upper generally tubular section 1200 to the lower most portion of the lower generally tubular section 1202. In some embodiments, the upper generally tubular section 1200 may taper downwardly without the lower generally tubular section 1202 doing so, or the lower generally tubular section 1202 may taper downwardly without the upper generally tubular section 1200 doing so. In still other embodiments, the outer perimeter of the handle housing 176 may not include a taper.

The upper generally tubular section 1200 includes the afore described buttons 180. As described above, the buttons 180 may be configured to control attributes of the emitted light from the light head 110, or to interface with a drive motor to rotate the afore mentioned camera assembly 182 within the handle housing 176. The buttons 180 are positioned in the recesses 1210 of the upper generally tubular section 1200 and, as shown in FIG. 4, protrude radially outwardly from the surfaces 1216 of the recesses 1210. The amount of protrusion from the surfaces 1216 is such that the tops or radially outermost portions of the buttons 180 extend radially outwardly relative to the radial extent in axial cross section of the outer perimeter of the lower generally tubular section 1202, or alternately extend radially outwardly approximately to the same radial extent as the outer perimeter of the lower generally tubular section 1202. This provides an ergonomic reach to the buttons 180, for example by the thumb of the user's hand, while enabling the user to maintain a grip on the lower generally tubular section 1202 by the other digits and palm of the user's hand.

As will be appreciated, the handle 164 allows the camera 184 and other components of the camera assembly 182 to be integrated within the handle 164 while maintaining an ergonomic grip and ergonomic button 180 operation. The inventors have found that commonly available cameras, for example HD, 4K or 8K block cameras, may be so large in size that incorporating such cameras into a surgical light head handle creates incompatibilities with maintaining the handle's ergonomics. The handle 164 including the upper generally tubular section 1200 where the buttons 180 are positioned, and the relatively wider lower generally tubular section 1202 within which the camera 184 is disposed, solves this problem by enabling incorporation of such a camera while maintaining the handle 164 ergonomic grip and ergonomic button 180 operation. The handle 164 advantageously provides an ergonomic shape and ergonomic size handle housing 176 while incorporating a suitable camera 184 within the handle housing 176.

Referring now to FIGS. 38-52 there is shown a handle 1300 in accordance with another embodiment of the invention. The handle 1300 is in many respects similar to the above-referenced handle 164 shown in FIGS. 3 and 4, and consequently the same reference numerals are used in FIGS. 38-52 to denote structures corresponding to similar structures in the handle 164. In addition, the foregoing description of the handle 164 is equally applicable to the handle 1300 and the following description of the handle 1300 is equally applicable to the handle 164, except where differences are noted herein. Moreover, it will be appreciated upon reading and understanding the specification that aspects of the handles 164, 600 may be substituted for one another or used in conjunction with one another where applicable.

As shown in FIGS. 37-50 and 38, the bottom of the lower generally tubular section 1202 is open downward. A camera 1304 is sized for insertion through the open bottom of the lower generally tubular section 1202 to within a handle housing 1302 of the handle 1300 and axially above the open bottom of the lower generally tubular section 1202. The handle housing 1302 of the FIGS. 38-52 embodiment differs from the handle housing 176 of the FIGS. 3 and 4 embodiment in that, as shown in FIG. 52, the inner perimeter of the lower generally tubular section 1202 is relatively wider in axial cross section than the inner perimeter of the upper generally tubular section 1200 whereas in the FIGS. 3 and 4 embodiment the inner perimeter of the lower generally tubular section 1202 has approximately the same width in axial cross section as the inner perimeter of the upper generally tubular section 1200, assuming a negligible effect in the taper of the handle housing 176 and handle housing 1302. This is accomplished in the illustrative embodiment by a shoulder 1306 that transitions radially outwardly from the inner perimeter of the upper generally tubular section 1200 to the inner perimeter of the lower generally tubular section 1202.

As will be appreciated, the relatively wider inner perimeter of the lower generally tubular section 1202 of the handle housing 1302 enables the handle housing 1302 to accommodate a wider camera 1304, that is, a camera 1304 that is relatively wider in axial cross section than the width of the inner perimeter of the upper generally tubular section 1200 yet relatively narrower in axial cross section than the width of the inner perimeter of the lower generally tubular section 1202. As shown in FIG. 52, the camera 1304 is relatively wider in axial cross section than the width of the inner perimeter of the upper generally tubular section 1200 yet still fits within the inner perimeter of the lower generally tubular section 1202. Thus, the camera 1304 is configured to be inserted into and contained within the inner perimeter of the lower generally tubular section 1202 but not into or within the inner perimeter of the upper generally tubular section 1200. This is regardless of the position of the camera 1304 about the center axis of the handle housing 1302. At least one axial cross section across the width of the camera 1304, that is perpendicularly across the center axis of the handle housing 1302, is relatively wider than any width in axial cross section across the width of the inner perimeter of the upper generally tubular section 1200, that is perpendicularly across the center axis of the handle housing 1302.

A cap 1320 is removably mounted to the bottom of the lower generally tubular section 1202 to close the open bottom in the lower generally tubular section 1202. As shown in FIGS. 47-50, the bottom of the lower generally tubular section 1202 includes a cylindrical shape threaded region 1324 and the cap 1320 includes a round shape mating threaded region 1326. The cap 1320 is removably mounted to the bottom of the lower generally tubular section 1202 by engagement between the round shape mating threaded region 1326 of the cap 1320 and the cylindrical shape threaded region 1324 of the bottom of the lower generally tubular section 1202.

As will be appreciated, the threaded connection of the detachable cap 1320 allows for easy removal and installation of the cap 1320 without any additional hardware, components, or tools such as fasteners or a screwdriver. With the cap 1320 mounted to the handle housing 1302, there is no exposed hardware and, consequently, cleanability is improved. Further, the removability of the cap 1320 enables access to the downwardly opening bottom of the handle 1300 and thus easy installation and/or replacement of the camera 1304 or other components of the camera assembly 182 from the bottom of the handle housing 1302 rather than for example removing the handle 1300 from the light head housing 116, 122 and accessing the inside of the handle 1300 through the top of the handle housing 1302. The removability of the cap 1320 also simplifies replacement of a camera glass 1340 that forms part of the cap 1320.

In the illustrated embodiment, the cylindrical shape threaded region 1324 is an external thread and the round shape mating thread 626 is an internal thread. Of course, other types of threaded connections are possible and contemplated. For example, the cylindrical shape threaded region 1324 may be an internal thread and the round shape mating thread 626 may be an external thread.

Referring now to FIGS. 51 and 52, the handle 1300 includes a single printed circuit board (PCB) that is disposed in the handle housing 1302. The handle 1300 differs from the handle 164 of the FIGS. 3-6 embodiment in that the handle 1300 has a single PCB disposed in the handle housing 1302 whereas the handle 164 has two PCBs disposed in the handle housing 176. As described above, the PCB, or PCBs as the case may be, provides control electronics 305 for controlling the camera assembly 182 including the camera 184 in the FIGS. 3-6 embodiment or the camera 1304 in the FIGS. 38-52 embodiment. As will be appreciated, the use of a single PCB instead of two or more PCBs reduces the volumetric footprint required by the PCB. The single PCB is disposed in the upper generally tubular section 1200 of the handle housing 1302, for example, within the inner perimeter of the upper generally tubular section 1200. As shown in FIG. 52, the single PCB is relatively narrower in axial cross section than the width of the inner perimeter of the upper generally tubular section 1200.

Although the invention has been shown and described with respect to certain preferred embodiments, it is understood that equivalents and modifications will occur to others skilled in the art upon the reading and understanding of the specification and the attached drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application. The present invention includes all such equivalents and modifications and is limited only by the scope of the following claims.

What is claimed is:

1. A surgical lighting system, comprising:
    a central shaft;
    a surgical light head;
    an extension arm having a hub at a proximal end thereof mounted to the central shaft for pivotable movement about the central shaft;
    a load balancing arm coupled to a distal end of the extension arm for pivotable movement relative to the extension arm;
    a yoke assembly coupled to a distal end of the load balancing arm for pivotable movement relative to the load balancing arm, wherein the yoke assembly supports the surgical light head for multi-axis movement relative to the load balancing arm;
    wherein the surgical light head includes a plurality of light emitting elements that are arranged to emit light downward to a region of interest and an optical signal generating component configured to capture data associated with the region of interest and generate an optical signal based on the captured data; and
    one or more optical fiber cables and one or more rotatable joints configured to transmit the optical signal associated with the captured data from the surgical light head to one or more of the yoke assembly, the load balancing arm, the extension arm, and the central shaft.

2. The surgical lighting system of claim 1, wherein the optical signal generating component comprises a camera having a field of view that encompasses at least a portion of the region of interest, and the optical signal includes optical video signals associated with video data captured by the camera.

3. The surgical lighting system of claim 1, wherein the optical signal includes a bidirectional control signal.

4. The surgical lighting system of claim 1, wherein the surgical light head includes a light head housing and a handle mounted to the light head housing and protruding downward from the light head housing, and wherein the optical signal generating component is mounted within the handle.

5. The surgical lighting system of claim 4, wherein the optical signal generating component is rotatable within the handle.

6. The surgical lighting system of claim 4, wherein the handle includes a first mating connector and the light head housing includes a hub having a second mating connector, and the handle is selectively attachable to and detachable from the hub wherein, in the attached state, the mated first and second mating connectors connect to transmit the optical signal from a first optical fiber cable inside the handle to a second optical fiber cable inside the light head housing.

7. The surgical lighting system of claim 1, wherein the one or more optical fiber cables are configured to transmit the optical signal associated with the captured data from the surgical light head through the yoke assembly and the load balancing arm to the extension arm.

8. The surgical lighting system of claim 1, wherein the yoke assembly is pivotably rotatable about the distal end of the load balancing arm via a first continuously rotatable joint and wherein the first continuously rotatable joint is configured to transmit the optical signal from a first optical fiber cable in the yoke assembly to a second optical fiber cable in the load balancing arm.

9. The surgical lighting system of claim 1, wherein the load balancing arm is pivotably rotatable about the distal end of the extension arm via a second continuously rotatable joint and wherein the second continuously rotatable joint is configured to transmit the optical signal from a second optical fiber cable in the load balancing arm to a third optical fiber cable in the extension arm.

10. The surgical lighting system of claim 1, wherein the extension arm is pivotably rotatable about the central shaft via a third continuously rotatable joint and wherein the third continuously rotatable joint is configured to transmit the optical signal from a third optical fiber cable in the extension arm to a fourth optical fiber cable in the central shaft.

11. The surgical lighting system of claim 1, wherein the one or more rotatable joints includes at least one fiber optic rotary joint.

12. The surgical lighting system of claim 11, wherein the fiber optic rotary joint includes a physical contact fiber optic rotary joint.

13. The surgical lighting system of claim 11, wherein the fiber optic rotary joint includes an expanded beam fiber optic rotary joint.

14. The surgical lighting system of claim 1, further comprising a second extension arm having a second hub at a proximal end thereof mounted to the central shaft for pivotable movement about the central shaft, a second load balancing arm pivotably mounted to a distal end of the second extension arm, and a display monitor coupled to a distal end of the second load balancing arm, wherein the one or more optical fiber cables includes a continuous cable run configured to transmit the optical signal from the central shaft to the second extension arm, the second load balancing arm, and the display monitor.

15. The surgical lighting system of claim 1, wherein the yoke assembly is pivotably rotatable about the distal end of the load balancing arm via a first rotatable joint, wherein the first rotatable joint includes a rotational component in the yoke assembly structured as a first mating connector and a stationary component in the load balancing arm structured as a second mating connector, and the yoke assembly is selectively attachable to and detachable from the load balancing arm wherein, in the attached state, the mated first and second mating connectors connect to transmit the optical signal from a first optical fiber cable inside the yoke assembly to a second optical fiber cable inside the load balancing arm.

16. The surgical lighting system of claim 1, wherein the load balancing arm is pivotably rotatable about the distal end of the extension arm via a second rotatable joint, wherein the second rotatable joint includes a rotational component in the load balancing arm structured as a first mating connector and a stationary component in the extension arm structured as a second mating connector, and the load balancing arm is selectively attachable to and detachable from the extension arm wherein, in the attached state, the mated first and second mating connectors connect to transmit the optical signal from a second optical fiber cable inside the load balancing arm to a third optical fiber cable inside the extension arm.

17. A surgical lighting system, comprising:
a central shaft;
a surgical light head;
a display monitor;
a first extension arm having a first hub at a proximal end thereof mounted to the central shaft for pivotable movement about the central shaft, and a first articulating assembly at a distal end thereof for supporting the surgical light head;
a second extension arm having a second hub at a proximal end thereof mounted to the central shaft for pivotable movement about the central shaft, and a second articulating assembly at a distal end thereof for supporting the display monitor;
wherein the surgical light head includes a plurality of light emitting elements that are arranged to emit light downward to a region of interest and an optical signal generating component configured to capture data associated with the region of interest and generate an optical signal based on the captured data;
wherein the optical signal is configured to drive the display monitor; and,
one or more optical fiber cables and one or more rotatable joints configured to transmit the optical signal associated with the captured data from the surgical light head to one or more of the first articulating assembly, the first extension arm, the central shaft, the second extension arm, the second articulating assembly, and the display monitor.

18. The surgical lighting system of claim 17, wherein the optical signal includes a bidirectional optical signal.

19. A surgical lighting system, comprising:
a central shaft;
a surgical light head;
a video processing device;
an extension arm having a hub at a proximal end thereof mounted to the central shaft for pivotable movement about the central shaft, and an articulating assembly at a distal end thereof for supporting the surgical light head;
wherein the surgical light head includes a plurality of light emitting elements that are arranged to emit light downward to a region of interest and an optical signal generating component configured to capture data associated with the region of interest and generate an optical signal based on the captured data;
wherein the optical signal is configured to drive the video processing device;
wherein the video processing device is located separate from the central shaft, the extension arm, and the articulating assembly; and,
one or more optical fiber cables and one or more rotatable joints configured to transmit the optical signal associated with the captured data from the surgical light head to one or more of the articulating assembly, the extension arm, the central shaft, and the video processing device.

20. The surgical lighting system of claim 19, further comprising a ceiling plate connected to the central shaft, wherein the one or more optical fiber cables extends through the central shaft and through the ceiling plate to the video processing device.

21. The surgical lighting system of claim 19, further comprising a video hub that converts the optical signal from the optical signal generating component into a video signal having video protocols compatible with the video processing device.

22. The surgical lighting system of claim 19, wherein the optical signal generating component includes a camera and the video processing device includes a display monitor.

* * * * *